United States Patent
Van Ryn et al.

(10) Patent No.: US 8,821,871 B2
(45) Date of Patent: Sep. 2, 2014

(54) ANTICOAGULANT ANTIDOTES COMPRISING ANTIBODIES THAT BIND DABIGATRAN AND/OR RELATED COMPOUNDS AND METHODS OF USE THEREOF

(75) Inventors: Joanne Van Ryn, Warthausen (DE); Keith Canada, Southbury, CT (US); Robert Copenhaver, Portland, OR (US); Norbert Hauel, Schemmerhofen (DE); Tobias Litzenburger, Mittelbiberach (DE); Christopher Ronald Sarko, New Milford, CT (US); Sanjaya Singh, Sandy Hook, CT (US); Alisa K. Waterman, Weston, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/432,296

(22) Filed: Mar. 28, 2012

(65) Prior Publication Data

US 2012/0276123 A1    Nov. 1, 2012

Related U.S. Application Data

(60) Provisional application No. 61/469,207, filed on Mar. 30, 2011.

(51) Int. Cl.
*A61K 39/395* (2006.01)
*C07K 16/44* (2006.01)

(52) U.S. Cl.
CPC ............. *C07K 16/44* (2013.01); *C07K 2317/76* (2013.01); *C07K 2317/24* (2013.01); *C07K 2317/55* (2013.01); *C07K 2317/56* (2013.01); *C07K 2317/565* (2013.01); *A61K 39/395* (2013.01)
USPC .................. 424/133.1; 424/141.1; 424/135.1; 424/139.1; 530/387.3; 530/388.1; 514/13.7; 514/14.7; 514/14.9

(58) Field of Classification Search
None
See application file for complete search history.

(56) References Cited

U.S. PATENT DOCUMENTS

| | | | |
|---|---|---|---|
| 5,693,762 | A | 12/1997 | Queen et al. |
| 5,910,573 | A | 6/1999 | Plückthun et al. |
| 6,440,417 | B1 | 8/2002 | Thibaudeau et al. |
| 6,469,039 | B1 | 10/2002 | Hauel et al. |
| 8,486,398 | B2 * | 7/2013 | Van Ryn et al. ........... 424/133.1 |
| 2004/0097547 | A1 | 5/2004 | Taveras et al. |
| 2009/0098119 | A1 | 4/2009 | Lu et al. |
| 2011/0206656 | A1 | 8/2011 | Van Ryn et al. |
| 2012/0027780 | A1 | 2/2012 | Van Ryn et al. |

FOREIGN PATENT DOCUMENTS

| | | |
|---|---|---|
| CA | 2 277 949 | 8/1998 |
| WO | WO-98 37075 | 8/1998 |
| WO | WO-2011 023653 | 3/2011 |
| WO | WO-2011 089183 | 7/2011 |

OTHER PUBLICATIONS

Harmsen et al., Mol Immunol. Aug. 2000;37(10):579-90.*

(Continued)

*Primary Examiner* — Michael Szperka
(74) *Attorney, Agent, or Firm* — Michael P. Morris; Wendy A. Petka

(57) ABSTRACT

The present invention relates to antibody molecules against anticoagulants, in particular dabigatran, and their use as antidotes of such anticoagulants.

19 Claims, 13 Drawing Sheets

(56) References Cited

OTHER PUBLICATIONS

Janeway et al., Immunobiology, 3rd edition, 1997, Garland Press, pp. 3:1-3:11.*
Rudikoff et al., Proc Natl Acad Sci USA, 1982, 79:1979-1983.*
Portolano et al., J. Immunol., 1993, 150:880-887.*
William E. Paul, M.D. ed., Fundamental Immunology, 3d ed. 1993, p. 242.*
Colburn, W. A. et al., "Specific antibodies and Fab Fragments to Alter the Pharmacokinetics and Reverse the Pharmacologic/ Toxicologic Effects of Drugs," Drug Metabolism Reviews, 1980, vol. 11, No. 2, pp. 223-262.
Eisert, W. G. et al., "Dabigatran: An Oral Novel Potent Reversible Nonpeptide Inhibitor of Thrombin," Arterioscler Thromb Vasc Biol., 2010, vol. 30, pp. 1885-1889.
Hardin, J. S. et al., "Pharmacodynamics of a monoclonal antiphencyclidine Fab with Broad Selectivity for Phencyclidine-Like Drugs," The Journal of Phamacology and Experiemental Therapeutics, 1998, vol. 285, No. 3, pp. 1113-1122.
Herion, P. et al., "Monoclonal Antibodies Against Plasma Protease Inhibitors: Production and Characterization of 15 Monoclonal Antibodies Against Human Antithrombin III. Relation Between Antigenic Determinants and Functional Sites of Antithrombin III." Blood, May 1965, vol. 65, No. 5, pp. 1201-1207.
Hursting, M. J. et al., "Drug-specific Fab Therapy in Drug Overdose," Arch Pathol Lab Med., Aug. 1987, vol. 111, pp. 693-697.
International Search Report for PCT/EP2011/073025 dated Mar. 14, 2012.
International Search Report for PCT/EP2012/055397 dated May 30, 2012.
Lapostolle, F. et al., "Assessment of digoxin antibody use in patients with elevated serum digoxin following chronic or acute exposure," Intensive Care Med., 2008, vol. 34, pp. 1448-1453.
Prescrire Int., 2009, vol. 101, pp. 97-99.
Schlaeppi, J. M. et al., "Preparation of monoclonal antibodies to hirudin and hirudin peptides—A method for studying the hirudin—thrombin interaction," European Journal of Biochemistry, 1990, vol. 188, No. 2, pp. 463-470.
Schulman, S. et al., "Anticoagulants and Their Reversal," Transfusion Medicine Reviews, Jan. 2007, vol. 21, No. 1, pp. 37-48.
Written Opinion for the International Searching Authority for PCT/EP2012/055397 dated May 30, 2012.
Written Opinion of the International Searching Authority for PCT/EP2011/073025 dated Mar. 14, 2012.
Zikria, J. C. et al., "Oral anticoagulation with factor Xa and thrombin inhibitors: on the threshold of change," Current Opinion in Hematology, 2009, vol. 16, No. 5, pp. 347-356.
Van Ryn, J. et al., "Dabigatran etexilate—novel, reversible, oral direct thrombin inhibitor: interpretation of coagulation assays and reversal of anticoagulant activity," Thrombosis and Haemostasis, 2011, vol. 105, No. 3, pp. 570.
Van Ryn, Joanne, et al; Dabigatran Etexilate—A Novel, Reversible, Oral Direct Thrombin Inhitor: Interpretation of Coagulation Assays and Reversal of Anticoagulant Activity; Thrombosis and Haemostasis (2010) pp. 1116-1127.
Van Ryn, Joanne, et al; Dabigatran Anticoagulant Activity is Neutralized by an Antibody Selective to Dabigatran an in vitro an in vivo Models; JACC (2011) vol. 57, No. 14 p. 1.

* cited by examiner

A) Fab 18/15

B) Fab VH5C/VK18

C) Fab VH5C/VK21

SEQUENCE LISTING

<160> NUMBER OF SEQ ID NOS: 101

<210> SEQ ID NO 1
<211> LENGTH: 10
<212> TYPE: PRT
<213> ORGANISM: Mus musculus
<220> FEATURE:
<223> OTHER INFORMATION: VHCDR1 DBG22

<400> SEQUENCE: 1

Gly Phe Ser Leu Thr Ser Tyr Ile Val Asp
1               5                   10

<210> SEQ ID NO 2
<211> LENGTH: 16
<212> TYPE: PRT
<213> ORGANISM: Mus musculus
<220> FEATURE:
<223> OTHER INFORMATION: VHCDR2 DBG22

<400> SEQUENCE: 2

Val Ile Trp Ala Gly Gly Ser Thr Asn Tyr Asn Ser Ala Leu Arg Ser
1               5                   10                  15

<210> SEQ ID NO 3
<211> LENGTH: 14
<212> TYPE: PRT
<213> ORGANISM: Mus musculus
<220> FEATURE:
<223> OTHER INFORMATION: VHCDR3 DBG22

<400> SEQUENCE: 3

Ala Ala Tyr Tyr Ser Tyr Tyr Asn Tyr Asp Gly Phe Ala Tyr
1               5                   10

<210> SEQ ID NO 4
<211> LENGTH: 16
<212> TYPE: PRT
<213> ORGANISM: Mus musculus
<220> FEATURE:
<223> OTHER INFORMATION: VKCDR1 DBG22

<400> SEQUENCE: 4

Lys Ser Ser Gln Ser Leu Leu Tyr Thr Asn Gly Lys Thr Tyr Leu Tyr
1               5                   10                  15

<210> SEQ ID NO 5
<211> LENGTH: 7
<212> TYPE: PRT
<213> ORGANISM: Mus musculus
<220> FEATURE:
<223> OTHER INFORMATION: VKCDR2 DBG22

<400> SEQUENCE: 5

Leu Val Ser Lys Leu Asp Ser
1               5

<210> SEQ ID NO 6
<211> LENGTH: 9
<212> TYPE: PRT
<213> ORGANISM: Mus musculus
<220> FEATURE:
<223> OTHER INFORMATION: VKCDR3 DBG22

<400> SEQUENCE: 6

Leu Gln Ser Thr His Phe Pro His Thr
1               5

```
<210> SEQ ID NO 7
<211> LENGTH: 10
<212> TYPE: PRT
<213> ORGANISM: Mus musculus
<220> FEATURE:
<223> OTHER INFORMATION: VHCDR1 35E6

<400> SEQUENCE: 7

Gly Tyr Thr Phe Thr Asn Tyr Trp Met His
1               5                   10

<210> SEQ ID NO 8
<211> LENGTH: 17
<212> TYPE: PRT
<213> ORGANISM: Mus musculus
<220> FEATURE:
<223> OTHER INFORMATION: VHCDR2 35E6

<400> SEQUENCE: 8

Glu Thr Asn Pro Arg Asn Gly Gly Thr Asn Tyr Asn Glu Lys Phe Lys
1               5                   10                  15

Arg

<210> SEQ ID NO 9
<211> LENGTH: 10
<212> TYPE: PRT
<213> ORGANISM: Mus musculus
<220> FEATURE:
<223> OTHER INFORMATION: VHCDR3 35E6

<400> SEQUENCE: 9

Gly Thr Ser Gly Tyr Asp Tyr Phe Asp Tyr
1               5                   10

<210> SEQ ID NO 10
<211> LENGTH: 16
<212> TYPE: PRT
<213> ORGANISM: Mus musculus
<220> FEATURE:
<223> OTHER INFORMATION: VKCDR1 35E6

<400> SEQUENCE: 10

Arg Ser Ser Gln Thr Ile Val His Ser Asn Gly Asn Thr Tyr Leu Glu
1               5                   10                  15

<210> SEQ ID NO 11
<211> LENGTH: 7
<212> TYPE: PRT
<213> ORGANISM: Mus musculus
<220> FEATURE:
<223> OTHER INFORMATION: VKCDR2 35E6

<400> SEQUENCE: 11

Lys Val Ser Asn Arg Phe Ser
1               5

<210> SEQ ID NO 12
<211> LENGTH: 9
<212> TYPE: PRT
<213> ORGANISM: Mus musculus
<220> FEATURE:
<223> OTHER INFORMATION: VKCDR2 35E6

<400> SEQUENCE: 12

Phe Gln Ala Ser His Phe Pro Tyr Thr
```

```
<210> SEQ ID NO 13
<211> LENGTH: 10
<212> TYPE: PRT
<213> ORGANISM: Mus musculus
<220> FEATURE:
<223> OTHER INFORMATION: VHCDR1 45B9

<400> SEQUENCE: 13

Gly Val Ser Leu Phe Thr Tyr Asp Val Asp
1               5                   10

<210> SEQ ID NO 14
<211> LENGTH: 16
<212> TYPE: PRT
<213> ORGANISM: Mus musculus
<220> FEATURE:
<223> OTHER INFORMATION: VHCDR2 45B9

<400> SEQUENCE: 14

Val Met Trp Ser Gly Gly Thr Thr Asn Tyr Asn Ser Ala Leu Lys Ser
1               5                   10                  15

<210> SEQ ID NO 15
<211> LENGTH: 10
<212> TYPE: PRT
<213> ORGANISM: Mus musculus
<220> FEATURE:
<223> OTHER INFORMATION: VHCDR3 45B9

<400> SEQUENCE: 15

Asp Arg Trp Ser Pro Gly Gly Phe Ala Tyr
1               5                   10

<210> SEQ ID NO 16
<211> LENGTH: 16
<212> TYPE: PRT
<213> ORGANISM: Mus musculus
<220> FEATURE:
<223> OTHER INFORMATION: VKCDR1 45B9

<400> SEQUENCE: 16

Gln Ser Ser Gln Ser Leu Leu Tyr Thr Asn Gly Lys Thr Tyr Leu His
1               5                   10                  15

<210> SEQ ID NO 17
<211> LENGTH: 7
<212> TYPE: PRT
<213> ORGANISM: Mus musculus
<220> FEATURE:
<223> OTHER INFORMATION: VKCDR2 45B9

<400> SEQUENCE: 17

Leu Val Ser Lys Leu Asp Ser
1               5

<210> SEQ ID NO 18
<211> LENGTH: 9
<212> TYPE: PRT
<213> ORGANISM: Mus musculus
<220> FEATURE:
<223> OTHER INFORMATION: VKCDR3 45B9

<400> SEQUENCE: 18

Leu Gln Ser Thr His Phe Pro His Thr
1               5
```

```
<210> SEQ ID NO 19
<211> LENGTH: 10
<212> TYPE: PRT
<213> ORGANISM: Mus musculus
<220> FEATURE:
<223> OTHER INFORMATION: VHCDR1 48E1

<400> SEQUENCE: 19

Gly Phe Ser Leu Thr Ser Tyr Asp Val Asp
1               5                   10

<210> SEQ ID NO 20
<211> LENGTH: 16
<212> TYPE: PRT
<213> ORGANISM: Mus musculus
<220> FEATURE:
<223> OTHER INFORMATION: VHCDR2 48E1

<400> SEQUENCE: 20

Val Ile Trp Ala Gly Gly Ser Thr Asn Tyr Asn Ser Ala Leu Lys Ser
1               5                   10                  15

<210> SEQ ID NO 21
<211> LENGTH: 10
<212> TYPE: PRT
<213> ORGANISM: Mus musculus
<220> FEATURE:
<223> OTHER INFORMATION: VHCDR3 48E1

<400> SEQUENCE: 21

Asp Arg Trp Ser Pro Gly Gly Phe Ala Tyr
1               5                   10

<210> SEQ ID NO 22
<211> LENGTH: 16
<212> TYPE: PRT
<213> ORGANISM: Mus musculus
<220> FEATURE:
<223> OTHER INFORMATION: VKCDR1 48E1

<400> SEQUENCE: 22

Lys Ser Ser Gln Ser Leu Leu Tyr Thr Asn Gly Lys Thr Tyr Leu Ile
1               5                   10                  15

<210> SEQ ID NO 23
<211> LENGTH: 7
<212> TYPE: PRT
<213> ORGANISM: Mus musculus
<220> FEATURE:
<223> OTHER INFORMATION: VKCDR2 48E1

<400> SEQUENCE: 23

Leu Val Ser Lys Leu Asp Ser
1               5

<210> SEQ ID NO 24
<211> LENGTH: 9
<212> TYPE: PRT
<213> ORGANISM: Mus musculus
<220> FEATURE:
<223> OTHER INFORMATION: VKCDR3 48E1

<400> SEQUENCE: 24

Leu Gln Thr Thr His Phe Pro His Thr
1               5
```

```
<210> SEQ ID NO 25
<211> LENGTH: 10
<212> TYPE: PRT
<213> ORGANISM: Mus musculus
<220> FEATURE:
<223> OTHER INFORMATION: VHCDR1 49F8

<400> SEQUENCE: 25

Gly Phe Ser Leu Ser Thr Tyr Gly Val Asp
1               5                   10

<210> SEQ ID NO 26
<211> LENGTH: 16
<212> TYPE: PRT
<213> ORGANISM: Mus musculus
<220> FEATURE:
<223> OTHER INFORMATION: VHCDR2 49F8

<400> SEQUENCE: 26

Leu Ile Trp Ala Gly Gly Ser Thr Thr Tyr Asn Ser Ala Phe Lys Ser
1               5                   10                  15

<210> SEQ ID NO 27
<211> LENGTH: 10
<212> TYPE: PRT
<213> ORGANISM: Mus musculus
<220> FEATURE:
<223> OTHER INFORMATION: VHCDR3 49F8

<400> SEQUENCE: 27

Glu Arg Ser Gly Asp Ser Pro Phe Gly Tyr
1               5                   10

<210> SEQ ID NO 28
<211> LENGTH: 16
<212> TYPE: PRT
<213> ORGANISM: Mus musculus
<220> FEATURE:
<223> OTHER INFORMATION: VKCDR1 49F8

<400> SEQUENCE: 28

Lys Ser Ser Gln Ser Leu Leu Tyr Thr Asn Gly Lys Thr Tyr Leu Asn
1               5                   10                  15

<210> SEQ ID NO 29
<211> LENGTH: 7
<212> TYPE: PRT
<213> ORGANISM: Mus musculus
<220> FEATURE:
<223> OTHER INFORMATION: VKCDR2 49F8

<400> SEQUENCE: 29

Leu Val Ser Lys Leu Asp Ser
1               5

<210> SEQ ID NO 30
<211> LENGTH: 9
<212> TYPE: PRT
<213> ORGANISM: Mus musculus
<220> FEATURE:
<223> OTHER INFORMATION: VKCDR3 49F8

<400> SEQUENCE: 30

Leu Gln Asn Ser His Phe Pro His Thr
1               5
```

```
<210> SEQ ID NO 31
<211> LENGTH: 10
<212> TYPE: PRT
<213> ORGANISM: Mus musculus
<220> FEATURE:
<223> OTHER INFORMATION: VHCDR1 6A7F1

<400> SEQUENCE: 31

Gly Phe Thr Phe Ser Thr Tyr Gly Met Ser
1               5                   10

<210> SEQ ID NO 32
<211> LENGTH: 14
<212> TYPE: PRT
<213> ORGANISM: Mus musculus
<220> FEATURE:
<223> OTHER INFORMATION: VHCDR2 6A7F1

<400> SEQUENCE: 32

Ser Val Thr Arg Gly Gly Asn Thr Tyr Tyr Pro Asp Ser Met
1               5                   10

<210> SEQ ID NO 33
<211> LENGTH: 9
<212> TYPE: PRT
<213> ORGANISM: Mus musculus
<220> FEATURE:
<223> OTHER INFORMATION: VHCDR3 6A7F1

<400> SEQUENCE: 33

Asp Tyr Ser Gly Trp Tyr Phe Asp Val
1               5

<210> SEQ ID NO 34
<211> LENGTH: 16
<212> TYPE: PRT
<213> ORGANISM: Mus musculus
<220> FEATURE:
<223> OTHER INFORMATION: VKCDR1 6A7F1

<400> SEQUENCE: 34

Arg Ser Ser Gln Ser Ile Val His Ser Asn Gly Asp Thr Phe Leu Glu
1               5                   10                  15

<210> SEQ ID NO 35
<211> LENGTH: 7
<212> TYPE: PRT
<213> ORGANISM: Mus musculus
<220> FEATURE:
<223> OTHER INFORMATION: VKCDR2 6A7F1

<400> SEQUENCE: 35

Lys Val Ser Asn Arg Phe Ser
1               5

<210> SEQ ID NO 36
<211> LENGTH: 9
<212> TYPE: PRT
<213> ORGANISM: Mus musculus
<220> FEATURE:
<223> OTHER INFORMATION: VKCDR3 6A7F1

<400> SEQUENCE: 36

Phe Gln Gly Ser Arg Ile Pro Tyr Thr
1               5

<210> SEQ ID NO 37
```

```
<211> LENGTH: 10
<212> TYPE: PRT
<213> ORGANISM: Mus musculus
<220> FEATURE:
<223> OTHER INFORMATION: VHCDR1 2F1E5

<400> SEQUENCE: 37

Gly Phe Thr Leu Thr Asn Tyr Gly Met Asn
1               5                   10

<210> SEQ ID NO 38
<211> LENGTH: 17
<212> TYPE: PRT
<213> ORGANISM: Mus musculus
<220> FEATURE:
<223> OTHER INFORMATION: VHCDR2 2F1E5

<400> SEQUENCE: 38

Trp Ile Asn Thr Tyr Thr Gly Glu Pro Thr Tyr Ala Asp Asp Phe Lys
1               5                   10                  15

Gly

<210> SEQ ID NO 39
<211> LENGTH: 9
<212> TYPE: PRT
<213> ORGANISM: Mus musculus
<220> FEATURE:
<223> OTHER INFORMATION: VHCDR3 2F1E5

<400> SEQUENCE: 39

Ser Ala Gly Thr Asp Tyr Phe Asp Tyr
1               5

<210> SEQ ID NO 40
<211> LENGTH: 15
<212> TYPE: PRT
<213> ORGANISM: Mus musculus
<220> FEATURE:
<223> OTHER INFORMATION: VKCDR1 2F1E5

<400> SEQUENCE: 40

Arg Ala Ser Glu Ser Val Asp Ser Tyr Gly Asn Ser Phe Met His
1               5                   10                  15

<210> SEQ ID NO 41
<211> LENGTH: 7
<212> TYPE: PRT
<213> ORGANISM: Mus musculus
<220> FEATURE:
<223> OTHER INFORMATION: VKCDR2 2F1E5

<400> SEQUENCE: 41

Leu Ala Ser Asn Leu Glu Ser
1               5

<210> SEQ ID NO 42
<211> LENGTH: 9
<212> TYPE: PRT
<213> ORGANISM: Mus musculus
<220> FEATURE:
<223> OTHER INFORMATION: VKCDR3 2F1E5

<400> SEQUENCE: 42

Gln Gln Asn Asn Glu Asp Pro Trp Thr
1               5
```

```
<210> SEQ ID NO 43
<211> LENGTH: 10
<212> TYPE: PRT
<213> ORGANISM: Mus musculus
<220> FEATURE:
<223> OTHER INFORMATION: VHCDR1 3B4E7

<400> SEQUENCE: 43

Gly Tyr Thr Phe Thr Tyr Tyr Thr Ile His
1               5                   10

<210> SEQ ID NO 44
<211> LENGTH: 17
<212> TYPE: PRT
<213> ORGANISM: Mus musculus
<220> FEATURE:
<223> OTHER INFORMATION: VHCDR2 3B4E7

<400> SEQUENCE: 44

Tyr Ile Asn Pro Ala Ser Ser Tyr Thr Asn Tyr Ile Gln Lys Phe Lys
1               5                   10                  15

Asp

<210> SEQ ID NO 45
<211> LENGTH: 9
<212> TYPE: PRT
<213> ORGANISM: Mus musculus
<220> FEATURE:
<223> OTHER INFORMATION: VHCDR3 3B4E7

<400> SEQUENCE: 45

Gly Ala Asn Trp Asp Tyr Phe Asp Tyr
1               5

<210> SEQ ID NO 46
<211> LENGTH: 16
<212> TYPE: PRT
<213> ORGANISM: Mus musculus
<220> FEATURE:
<223> OTHER INFORMATION: VKCDR1 3B4E7

<400> SEQUENCE: 46

Arg Ser Ser Gln Asn Ile Ile Gln Ser Asn Gly Asn Thr Tyr Leu Glu
1               5                   10                  15

<210> SEQ ID NO 47
<211> LENGTH: 7
<212> TYPE: PRT
<213> ORGANISM: Mus musculus
<220> FEATURE:
<223> OTHER INFORMATION: VKCDR2 3B4E7

<400> SEQUENCE: 47

Lys Val Ser Asn Arg Phe Ser
1               5

<210> SEQ ID NO 48
<211> LENGTH: 9
<212> TYPE: PRT
<213> ORGANISM: Mus musculus
<220> FEATURE:
<223> OTHER INFORMATION: VKCDR3 3B4E7

<400> SEQUENCE: 48

Phe Gln Gly Ser His Val Pro Tyr Thr
1               5
```

```
<210> SEQ ID NO 49
<211> LENGTH: 10
<212> TYPE: PRT
<213> ORGANISM: Mus musculus
<220> FEATURE:
<223> OTHER INFORMATION: VHCDR1 1F6G8

<400> SEQUENCE: 49

Gly Tyr Thr Phe Thr Ser Tyr Thr Ile His
1               5                   10

<210> SEQ ID NO 50
<211> LENGTH: 17
<212> TYPE: PRT
<213> ORGANISM: Mus musculus
<220> FEATURE:
<223> OTHER INFORMATION: VHCDR2 1F6G8

<400> SEQUENCE: 50

Tyr Ile Asn Pro Ser Ser Gly Tyr Thr Tyr Tyr Ile Gln Asn Phe Lys
1               5                   10                  15

Asp

<210> SEQ ID NO 51
<211> LENGTH: 9
<212> TYPE: PRT
<213> ORGANISM: Mus musculus
<220> FEATURE:
<223> OTHER INFORMATION: VHCDR3 1F6G8

<400> SEQUENCE: 51

Gly Ala Asn Trp Asp Tyr Phe Asp Tyr
1               5

<210> SEQ ID NO 52
<211> LENGTH: 16
<212> TYPE: PRT
<213> ORGANISM: Mus musculus
<220> FEATURE:
<223> OTHER INFORMATION: VKCDR1 1F6G8

<400> SEQUENCE: 52

Arg Ser Ser Gln Asn Ile Val Gln Thr Asn Gly Asn Thr Tyr Leu Glu
1               5                   10                  15

<210> SEQ ID NO 53
<211> LENGTH: 7
<212> TYPE: PRT
<213> ORGANISM: Mus musculus
<220> FEATURE:
<223> OTHER INFORMATION: VKCDR2 1F6G8

<400> SEQUENCE: 53

Lys Val Ser Ser Arg Phe Ser
1               5

<210> SEQ ID NO 54
<211> LENGTH: 9
<212> TYPE: PRT
<213> ORGANISM: Mus musculus
<220> FEATURE:
<223> OTHER INFORMATION: VKCDR3 1F6G8

<400> SEQUENCE: 54

Phe Gln Gly Ser His Val Pro Phe Thr
1               5
```

<210> SEQ ID NO 55
<211> LENGTH: 10
<212> TYPE: PRT
<213> ORGANISM: Mus musculus
<220> FEATURE:
<223> OTHER INFORMATION: VHCDR1 2D2E3

<400> SEQUENCE: 55

Gly Tyr Thr Phe Thr His Ser Gly Met Asn
1               5                   10

<210> SEQ ID NO 56
<211> LENGTH: 18
<212> TYPE: PRT
<213> ORGANISM: Mus musculus
<220> FEATURE:
<223> OTHER INFORMATION: VHCDR2 2D2E3

<400> SEQUENCE: 56

Trp Ile Asn Thr Asn Thr Gly Glu Pro Thr Tyr Ala Glu Glu Phe Asn
1               5                   10                  15

Gly Arg

<210> SEQ ID NO 57
<211> LENGTH: 9
<212> TYPE: PRT
<213> ORGANISM: Mus musculus
<220> FEATURE:
<223> OTHER INFORMATION: VHCDR3 2D2E3

<400> SEQUENCE: 57

Ser Trp Trp Thr Asp Tyr Phe Asp Tyr
1               5

<210> SEQ ID NO 58
<211> LENGTH: 16
<212> TYPE: PRT
<213> ORGANISM: Mus musculus
<220> FEATURE:
<223> OTHER INFORMATION: VKCDR1 2D2F8

<400> SEQUENCE: 58

Arg Ser Ser Gln Ser Ile Val His Ser Asn Gly Asn Thr Tyr Leu Glu
1               5                   10                  15

<210> SEQ ID NO 59
<211> LENGTH: 7
<212> TYPE: PRT
<213> ORGANISM: Mus musculus
<220> FEATURE:
<223> OTHER INFORMATION: VKCDR2 2D2E3

<400> SEQUENCE: 59

Lys Val Ser Asn Arg Phe Ser
1               5

<210> SEQ ID NO 60
<211> LENGTH: 9
<212> TYPE: PRT
<213> ORGANISM: Mus musculus
<220> FEATURE:
<223> OTHER INFORMATION: VKCDR3 2D2E3

<400> SEQUENCE: 60

Phe Gln Gly Ser His Phe Pro Tyr Thr

```
1               5

<210> SEQ ID NO 61
<211> LENGTH: 10
<212> TYPE: PRT
<213> ORGANISM: Mus musculus
<220> FEATURE:
<223> OTHER INFORMATION: VHCDR1 27A9

<400> SEQUENCE: 61

Gly Tyr Thr Phe Thr Asn Cys Tyr Met His
1               5                   10

<210> SEQ ID NO 62
<211> LENGTH: 17
<212> TYPE: PRT
<213> ORGANISM: Mus musculus
<220> FEATURE:
<223> OTHER INFORMATION: VHCDR2 27A9

<400> SEQUENCE: 62

Glu Thr Asn Pro Arg Asn Gly Gly Thr Asn Tyr Asn Glu Lys Phe Lys
1               5                   10                  15

Arg

<210> SEQ ID NO 63
<211> LENGTH: 10
<212> TYPE: PRT
<213> ORGANISM: Mus musculus
<220> FEATURE:
<223> OTHER INFORMATION: VHCDR3 27A9

<400> SEQUENCE: 63

Gly Thr Ser Gly Tyr Glu Tyr Phe Asp Tyr
1               5                   10

<210> SEQ ID NO 64
<211> LENGTH: 16
<212> TYPE: PRT
<213> ORGANISM: Mus musculus
<220> FEATURE:
<223> OTHER INFORMATION: VKCDR1 27A9

<400> SEQUENCE: 64

Arg Ser Ser Gln Ser Ile Val His Ser Asp Gly Asn Ile Tyr Leu Glu
1               5                   10                  15

<210> SEQ ID NO 65
<211> LENGTH: 7
<212> TYPE: PRT
<213> ORGANISM: Mus musculus
<220> FEATURE:
<223> OTHER INFORMATION: VKCDR2 27A9

<400> SEQUENCE: 65

Lys Val Ser Tyr Arg Phe Ser
1               5

<210> SEQ ID NO 66
<211> LENGTH: 9
<212> TYPE: PRT
<213> ORGANISM: Mus musculus
<220> FEATURE:
<223> OTHER INFORMATION: VKCDR3 27A9

<400> SEQUENCE: 66
```

Phe Gln Gly Ser His Val Pro Tyr Thr
1               5

<210> SEQ ID NO 67
<211> LENGTH: 10
<212> TYPE: PRT
<213> ORGANISM: Mus musculus
<220> FEATURE:
<223> OTHER INFORMATION: VHCDR1 5C

<400> SEQUENCE: 67

Gly Tyr Thr Phe Thr Asp Tyr Tyr Met His
1               5                   10

<210> SEQ ID NO 68
<211> LENGTH: 17
<212> TYPE: PRT
<213> ORGANISM: Mus musculus
<220> FEATURE:
<223> OTHER INFORMATION: VHCDR2 5C

<400> SEQUENCE: 68

Glu Thr Asn Pro Arg Asn Gly Gly Thr Thr Tyr Asn Glu Lys Phe Lys
1               5                   10                  15

Gly

<210> SEQ ID NO 69
<211> LENGTH: 9
<212> TYPE: PRT
<213> ORGANISM: Mus musculus
<220> FEATURE:
<223> OTHER INFORMATION: VKCDR3 18

<400> SEQUENCE: 69

Phe Gln Ala Ser His Val Pro Tyr Thr
1               5

<210> SEQ ID NO 70
<211> LENGTH: 122
<212> TYPE: PRT
<213> ORGANISM: Mus musculus
<220> FEATURE:
<223> OTHER INFORMATION: DBG22VH

<400> SEQUENCE: 70

Gln Val Gln Leu Glu Gln Ser Gly Pro Gly Leu Val Ala Pro Ser Gln
1               5                   10                  15

Arg Leu Ser Ile Thr Cys Thr Val Ser Gly Phe Ser Leu Thr Ser Tyr
            20                  25                  30

Ile Val Asp Trp Val Arg Gln Ser Pro Gly Lys Gly Leu Glu Trp Leu
        35                  40                  45

Gly Val Ile Trp Ala Gly Gly Ser Thr Asn Tyr Asn Ser Ala Leu Arg
    50                  55                  60

Ser Arg Leu Ser Ile Thr Lys Ser Asn Ser Lys Ser Gln Val Phe Leu
65                  70                  75                  80

Gln Met Asn Ser Leu Gln Thr Asp Asp Thr Ala Ile Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ala
        115                 120

```
<210> SEQ ID NO 71
<211> LENGTH: 112
<212> TYPE: PRT
<213> ORGANISM: Mus musculus
<220> FEATURE:
<223> OTHER INFORMATION: DBG22VK

<400> SEQUENCE: 71

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Tyr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Leu Gln Ser
                85                  90                  95

Thr His Phe Pro His Thr Phe Gly Gly Gly Thr Lys Leu Glu Ile Lys
            100                 105                 110

<210> SEQ ID NO 72
<211> LENGTH: 119
<212> TYPE: PRT
<213> ORGANISM: Mus musculus
<220> FEATURE:
<223> OTHER INFORMATION: 35E6VH

<400> SEQUENCE: 72

Gln Val Gln Leu Gln Gln Pro Gly Ala Glu Leu Val Lys Pro Gly Ala
1               5                   10                  15

Ser Val Lys Leu Ser Cys Lys Thr Ser Gly Tyr Thr Phe Thr Asn Tyr
            20                  25                  30

Trp Met His Trp Val Arg Gln Arg Pro Gly Gln Gly Leu Glu Trp Ile
        35                  40                  45

Gly Glu Thr Asn Pro Arg Asn Gly Gly Thr Asn Tyr Asn Glu Lys Phe
    50                  55                  60

Lys Arg Lys Ala Thr Leu Thr Val Asp Lys Ser Ser Asn Thr Ala Tyr
65                  70                  75                  80

Met Gln Leu Ser Ser Leu Thr Phe Gly Asp Ser Ala Val Tyr Tyr Cys
                85                  90                  95

Thr Ile Gly Thr Ser Gly Tyr Asp Tyr Phe Asp Tyr Trp Gly Gln Gly
            100                 105                 110

Thr Thr Leu Thr Val Ser Ser
        115

<210> SEQ ID NO 73
<211> LENGTH: 112
<212> TYPE: PRT
<213> ORGANISM: Mus musculus
<220> FEATURE:
<223> OTHER INFORMATION: 35E6VK

<400> SEQUENCE: 73

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30
```

```
Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Gly Phe Thr Leu Lys Ile
 65                  70                  75                  80

Ser Arg Val Glu Ala Glu Asp Leu Gly Val Tyr Phe Cys Phe Gln Ala
                 85                  90                  95

Ser His Phe Pro Tyr Thr Phe Gly Gly Gly Thr Lys Leu Glu Ile Lys
             100                 105                 110
```

<210> SEQ ID NO 74
<211> LENGTH: 118
<212> TYPE: PRT
<213> ORGANISM: Mus musculus
<220> FEATURE:
<223> OTHER INFORMATION: 45B9VH

<400> SEQUENCE: 74

```
Gln Val Gln Leu Lys Gln Ser Gly Pro Gly Leu Val Ala Pro Ser Gln
 1               5                  10                  15

Ser Leu Ser Ile Thr Cys Thr Val Ser Gly Val Ser Leu Phe Thr Tyr
                 20                  25                  30

Asp Val Asp Trp Val Arg Gln Ser Pro Gly Lys Asp Leu Glu Trp Leu
             35                  40                  45

Gly Val Met Trp Ser Gly Gly Thr Thr Asn Tyr Asn Ser Ala Leu Lys
         50                  55                  60

Ser Arg Leu Asn Ile Met Lys Asp Ser Ser Lys Ser Gln Val Phe Leu
 65                  70                  75                  80

Lys Met Ser Gly Leu Gln Thr Asp Asp Thr Gly Ile Tyr Tyr Cys Ala
                 85                  90                  95

Thr Asp Arg Trp Ser Pro Gly Gly Phe Ala Tyr Trp Gly Gln Gly Thr
             100                 105                 110

Leu Val Thr Val Ser Ala
         115
```

<210> SEQ ID NO 75
<211> LENGTH: 112
<212> TYPE: PRT
<213> ORGANISM: Mus musculus
<220> FEATURE:
<223> OTHER INFORMATION: 45B9VK

<400> SEQUENCE: 75

```
Asp Val Val Met Thr Gln Thr Pro Leu Thr Leu Ser Val Leu Ile Gly
 1               5                  10                  15

Gln Pro Ala Ser Ile Ser Cys Gln Ser Ser Gln Ser Leu Leu Tyr Thr
                 20                  25                  30

Asn Gly Lys Thr Tyr Leu His Trp Leu Leu Gln Arg Pro Gly Gln Ser
             35                  40                  45

Pro Lys Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Leu Gln Ser
                 85                  90                  95

Thr His Phe Pro His Thr Phe Gly Gly Gly Thr Lys Leu Glu Ile Arg
```

100             105             110

<210> SEQ ID NO 76
<211> LENGTH: 118
<212> TYPE: PRT
<213> ORGANISM: Mus musculus
<220> FEATURE:
<223> OTHER INFORMATION: 48E1VH

<400> SEQUENCE: 76

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Val Asp Trp Val Arg Gln Ser Pro Gly Lys Gly Leu Glu Trp Leu
        35                  40                  45

Gly Val Ile Trp Ala Gly Gly Ser Thr Asn Tyr Asn Ser Ala Leu Lys
    50                  55                  60

Ser Arg Leu Ile Ile Ser Lys Asp Asn Ser Lys Asn Gln Val Phe Leu
65                  70                  75                  80

Arg Met Asn Ser Leu Gln Thr Asp Asp Thr Ala Met Tyr Tyr Cys Ala
                85                  90                  95

Ser Asp Arg Trp Ser Pro Gly Gly Phe Ala Tyr Trp Gly Gln Gly Thr
            100                 105                 110

Leu Val Thr Val Ser Ala
        115

<210> SEQ ID NO 77
<211> LENGTH: 112
<212> TYPE: PRT
<213> ORGANISM: Mus musculus
<220> FEATURE:
<223> OTHER INFORMATION: 48E1VK

<400> SEQUENCE: 77

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Ile Trp Leu Leu Gln Arg Pro Gly Gln Ser
        35                  40                  45

Pro Lys Arg Leu Ile His Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Tyr Cys Leu Gln Thr
                85                  90                  95

Thr His Phe Pro His Thr Phe Gly Gly Gly Thr Lys Leu Glu Ile Arg
            100                 105                 110

<210> SEQ ID NO 78
<211> LENGTH: 118
<212> TYPE: PRT
<213> ORGANISM: Mus musculus
<220> FEATURE:
<223> OTHER INFORMATION: 49F8VH

<400> SEQUENCE: 78

Gln Val Gln Leu Lys Gln Ser Gly Pro Gly Leu Val Ala Pro Ser Gln
1               5                   10                  15

```
Ser Leu Ser Ile Thr Cys Thr Val Ser Gly Phe Ser Leu Ser Thr Tyr
            20                  25                  30

Gly Val Asp Trp Val Arg Gln Ser Pro Lys Lys Gly Leu Glu Trp Leu
        35                  40                  45

Gly Leu Ile Trp Ala Gly Gly Ser Thr Thr Tyr Asn Ser Ala Phe Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Ser Glu Arg Ser Gly Asp Ser Pro Phe Gly Tyr Trp Gly Gln Gly Thr
            100                 105                 110

Leu Val Thr Val Ser Ala
        115

<210> SEQ ID NO 79
<211> LENGTH: 112
<212> TYPE: PRT
<213> ORGANISM: Mus musculus
<220> FEATURE:
<223> OTHER INFORMATION: 49F8VK

<400> SEQUENCE: 79

Asp Val Val Met Thr Gln Ser Pro Leu Ile Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Asn Trp Leu Leu Gln Arg Pro Gly Gln Ser
        35                  40                  45

Pro Glu Arg Leu Ile His Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Asn
                85                  90                  95

Ser His Phe Pro His Thr Phe Gly Ser Gly Thr Lys Leu Glu Ile Lys
            100                 105                 110

<210> SEQ ID NO 80
<211> LENGTH: 117
<212> TYPE: PRT
<213> ORGANISM: Mus musculus
<220> FEATURE:
<223> OTHER INFORMATION: 6A7F1VH

<400> SEQUENCE: 80

Glu Val Lys Leu Val Glu Ser Gly Gly Asp Leu Val Arg Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Ser Pro Glu Lys Arg Leu Glu Trp Val
        35                  40                  45

Ala Ser Val Thr Arg Gly Gly Asn Thr Tyr Tyr Pro Asp Ser Met Arg
    50                  55                  60

Gly Arg Phe Thr Ile Ser Arg Asp Asn Val Gly Asn Ile Leu Tyr Leu
65                  70                  75                  80

His Leu Arg Ser Leu Arg Ser Glu Asp Thr Ala Ile Tyr Phe Cys Ala
```

```
                    85                  90                  95
Arg Asp Tyr Ser Gly Trp Tyr Phe Asp Val Trp Gly Ala Gly Thr Thr
                    100                 105                 110

Val Thr Val Ser Ser
        115

<210> SEQ ID NO 81
<211> LENGTH: 112
<212> TYPE: PRT
<213> ORGANISM: Mus musculus
<220> FEATURE:
<223> OTHER INFORMATION: 6A7F1VK

<400> SEQUENCE: 81

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asp Thr Phe Leu Glu Trp Tyr Leu Gln Lys Ser Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Arg Ile Pro Tyr Thr Phe Gly Gly Gly Thr Lys Leu Glu Ile Lys
                100                 105                 110

<210> SEQ ID NO 82
<211> LENGTH: 118
<212> TYPE: PRT
<213> ORGANISM: Mus musculus
<220> FEATURE:
<223> OTHER INFORMATION: 3B4E7VH

<400> SEQUENCE: 82

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Tyr Tyr
                20                  25                  30

Thr Ile His Trp Val Lys Gln Arg Pro Gly Gln Gly Leu Glu Trp Ile
            35                  40                  45

Gly Tyr Ile Asn Pro Ala Ser Ser Tyr Thr Asn Tyr Ile Gln Lys Phe
        50                  55                  60

Lys Asp Arg Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Phe Tyr Cys
                85                  90                  95

Ala Arg Gly Ala Asn Trp Asp Tyr Phe Asp Tyr Trp Gly Gln Gly Thr
                100                 105                 110

Thr Leu Thr Val Ser Ser
        115

<210> SEQ ID NO 83
<211> LENGTH: 112
<212> TYPE: PRT
<213> ORGANISM: Mus musculus
<220> FEATURE:
```

<223> OTHER INFORMATION: 3B4E7VK

<400> SEQUENCE: 83

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Asn Leu Glu Ile Lys
            100                 105                 110

<210> SEQ ID NO 84
<211> LENGTH: 118
<212> TYPE: PRT
<213> ORGANISM: Mus musculus
<220> FEATURE:
<223> OTHER INFORMATION: 2F1E5VH

<400> SEQUENCE: 84

Gln Ile Gln Leu Val Gln Ser Gly Pro Glu Leu Lys Lys Pro Gly Glu
1               5                   10                  15

Thr Val Lys Ile Ser Cys Lys Ser Ser Gly Phe Thr Leu Thr Asn Tyr
            20                  25                  30

Gly Met Asn Trp Val Lys Gln Val Pro Gly Lys Gly Leu Arg Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Ala Ala Thr Tyr Phe Cys
                85                  90                  95

Ala Arg Ser Ala Gly Thr Asp Tyr Phe Asp Tyr Trp Gly Gln Gly Thr
            100                 105                 110

Thr Leu Thr Val Ser Ser
        115

<210> SEQ ID NO 85
<211> LENGTH: 111
<212> TYPE: PRT
<213> ORGANISM: Mus musculus
<220> FEATURE:
<223> OTHER INFORMATION: 2F1E5VK

<400> SEQUENCE: 85

Asn Phe Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Cys Gln Gln Lys Pro Gly Gln Pro Pro
        35                  40                  45

Lys Leu Leu Ile Tyr Leu Ala Ser Asn Leu Glu Ser Gly Val Pro Ala

```
                    50                  55                  60
Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                     85                  90                  95

Glu Asp Pro Trp Thr Phe Gly Gly Gly Thr Lys Leu Glu Ile Lys
                100                 105                 110
```

<210> SEQ ID NO 86
<211> LENGTH: 118
<212> TYPE: PRT
<213> ORGANISM: Mus musculus
<220> FEATURE:
<223> OTHER INFORMATION: 1F6G8VH

<400> SEQUENCE: 86

```
Gln Ile Gln Leu Val Gln Ser Gly Pro Glu Leu Lys Lys Pro Gly Glu
  1               5                  10                  15

Thr Val Lys Ile Ser Cys Lys Ser Gly Phe Thr Leu Thr Asn Tyr
                 20                  25                  30

Gly Met Asn Trp Val Lys Gln Val Pro Gly Lys Gly Leu Arg Trp Met
                 35                  40                  45

Gly Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Arg Thr Ala Tyr
 65                  70                  75                  80

Leu Gln Ile Asn Asn Leu Lys Asn Glu Asp Ala Ala Thr Tyr Phe Cys
                     85                  90                  95

Ala Arg Ser Ala Gly Thr Asp Tyr Phe Asp Tyr Trp Gly Gln Gly Thr
                100                 105                 110

Thr Leu Thr Val Ser Ser
                115
```

<210> SEQ ID NO 87
<211> LENGTH: 112
<212> TYPE: PRT
<213> ORGANISM: Mus musculus
<220> FEATURE:
<223> OTHER INFORMATION: 1F6G8VK

<400> SEQUENCE: 87

```
Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Asn Ile Val Gln Thr
                 20                  25                  30

Asn Gly Asn Thr Tyr Leu Glu Trp Tyr Leu Gln Lys Pro Gly Gln Ser
                 35                  40                  45

Pro Asn Leu Leu Ile Tyr Lys Val Ser Ser Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                     85                  90                  95

Ser His Val Pro Phe Thr Phe Gly Gly Gly Thr Lys Leu Glu Ile Lys
                100                 105                 110
```

<210> SEQ ID NO 88
<211> LENGTH: 120

```
<212> TYPE: PRT
<213> ORGANISM: Mus musculus
<220> FEATURE:
<223> OTHER INFORMATION: 2D2E3VH

<400> SEQUENCE: 88

Gln Ala Gln Ile His Leu Val Gln Ser Gly Pro Glu Leu Lys Lys Pro
1               5                   10                  15

Gly Glu Thr Val Lys Ile Ser Cys Lys Ala Ser Gly Tyr Thr Phe Thr
                20                  25                  30

His Ser Gly Met Asn Trp Met Lys Gln Thr Pro Gly Lys Asp Leu Lys
            35                  40                  45

Trp Met Gly Trp Ile Asn Thr Asn Thr Gly Glu Pro Thr Tyr Ala Glu
        50                  55                  60

Glu Phe Asn Gly Arg Phe Ala Phe Ser Leu Glu Ala Ser Ala Asn Thr
65                  70                  75                  80

Ala Tyr Leu Gln Ile Asn Asn Leu Lys Asn Glu Asp Thr Ala Thr Tyr
                85                  90                  95

Phe Cys Ala Arg Ser Trp Trp Thr Asp Tyr Phe Asp Tyr Trp Gly Gln
            100                 105                 110

Gly Thr Thr Leu Thr Val Ser Ser
        115                 120

<210> SEQ ID NO 89
<211> LENGTH: 112
<212> TYPE: PRT
<213> ORGANISM: Mus musculus
<220> FEATURE:
<223> OTHER INFORMATION: 2D2E3VK

<400> SEQUENCE: 89

Asp Val Leu Met Thr Gln Thr Pro Leu Ser Leu Pro Val Ser Leu Gly
1               5                   10                  15

Asp Gln Thr Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Glu Leu Leu Ile Tyr Lys Val Ser Asn Arg Phe Ser Gly Val Pro
        50                  55                  60

Asp Arg Ile Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Tyr Thr Phe Gly Gly Gly Thr Lys Leu Glu Ile Thr
            100                 105                 110

<210> SEQ ID NO 90
<211> LENGTH: 119
<212> TYPE: PRT
<213> ORGANISM: Mus musculus
<220> FEATURE:
<223> OTHER INFORMATION: 27A9VH

<400> SEQUENCE: 90

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Cys
                20                  25                  30

Tyr Met His Trp Val Lys Gln Arg Pro Gly Gln Gly Leu Glu Trp Ile
```

```
                35                  40                  45
Gly Glu Thr Asn Pro Arg Asn Gly Gly Thr Asn Tyr Asn Glu Lys Phe
        50                  55                  60

Lys Arg Lys Ala Thr Leu Thr Val Asn Lys Tyr Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile Gly Thr Ser Gly Tyr Glu Tyr Phe Asp Tyr Trp Gly Gln Gly
                100                 105                 110

Thr Thr Leu Thr Val Ser Ser
                115

<210> SEQ ID NO 91
<211> LENGTH: 112
<212> TYPE: PRT
<213> ORGANISM: Mus musculus
<220> FEATURE:
<223> OTHER INFORMATION: 27A9VK

<400> SEQUENCE: 91

Asn Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asp Gly Asn Ile Tyr Leu Glu Trp Tyr Leu Gln Lys Pro Gly Gln Ser
                35                  40                  45

Pro Lys Val Leu Ile Tyr Lys Val Ser Tyr Arg Phe Ser Gly Val Pro
        50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Tyr Thr Phe Gly Gly Gly Thr Lys Leu Glu Ile Lys
                100                 105                 110

<210> SEQ ID NO 92
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH5C

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
                35                  40                  45

Gly Glu Thr Asn Pro Arg Asn Gly Gly Thr Thr Tyr Asn Glu Lys Phe
        50                  55                  60

Lys Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Ile Gly Thr Ser Gly Tyr Asp Tyr Phe Asp Tyr Trp Gly Gln Gly
                100                 105                 110

Thr Leu Val Thr Val Ser Ser
        115

<210> SEQ ID NO 93
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VK18

<400> SEQUENCE: 93

Asp Ile Val Met Thr Gln Thr Pro Leu Ser Leu Ser Val Thr Pro Gly
1               5                   10                  15

Gln Pro Ala Ser Ile Ser Cys Arg Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VK21

<400> SEQUENCE: 94

Asp Ile Val Met Thr Gln Thr Pro Leu Ser Leu Ser Val Thr Pro Gly
1               5                   10                  15

Gln Pro Ala Ser Ile Ser Cys Arg Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Gly Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gly Gly Thr Lys Leu Glu Ile Lys
            100                 105                 110

<210> SEQ ID NO 95
<211> LENGTH: 452
<212> TYPE: PRT
<213> ORGANISM: Artificial Sequence
```

-continued

<220> FEATURE:
<223> OTHER INFORMATION: Description of Artificial Sequence: Synthetic
      polypeptide
<220> FEATURE:
<223> OTHER INFORMATION: Clone 22 chimeric HC

<400> SEQUENCE: 95

```
Gln Val Gln Leu Glu Gln Ser Gly Pro Gly Leu Val Ala Pro Ser Gln
1               5                   10                  15

Arg Leu Ser Ile Thr Cys Thr Val Ser Gly Phe Ser Leu Thr Ser Tyr
            20                  25                  30

Ile Val Asp Trp Val Arg Gln Ser Pro Gly Lys Gly Leu Glu Trp Leu
        35                  40                  45

Gly Val Ile Trp Ala Gly Gly Ser Thr Asn Tyr Asn Ser Ala Leu Arg
    50                  55                  60

Ser Arg Leu Ser Ile Thr Lys Ser Asn Ser Lys Ser Gln Val Phe Leu
65                  70                  75                  80

Gln Met Asn Ser Leu Gln Thr Asp Asp Thr Ala Ile Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 96
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 22 chimeric LC

<400> SEQUENCE: 96

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Tyr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Leu Gln Ser
                85                  90                  95

Thr His Phe Pro His Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 97
<211> LENGTH: 107
<212> TYPE: PRT
<213> ORGANISM: Homo sapiens
<220> FEATURE:
<223> OTHER INFORMATION: hCL Domain
```

-continued

<400> SEQUENCE: 97

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 98
<211> LENGTH: 330
<212> TYPE: PRT
<213> ORGANISM: Homo sapiens
<220> FEATURE:
<223> OTHER INFORMATION: hCH Domain

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr

```
                    245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 99
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HCVH5C

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Glu Thr Asn Pro Arg Asn Gly Thr Thr Tyr Asn Glu Lys Phe
    50                  55                  60

Lys Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ile Gly Thr Ser Gly Tyr Asp Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 100
<211> LENGTH: 219
<212> TYPE: PRT
<213> ORGANISM: Artificial Sequence
<220> FEATURE:
<223> OTHER INFORMATION: Description of Artificial Sequence: Synthetic
```

```
                polypeptide
<220> FEATURE:
<223> OTHER INFORMATION: LCVK18

<400> SEQUENCE: 100

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 101
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LCVK21

<400> SEQUENCE: 101

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Gly Phe Thr Leu Lys Ile
65                  70                  75                  80

Ser Arg Val Glu Ala Glu Asp Val Gly Val Tyr Tyr Cys Phe Gln Ala
                85                  90                  95
```

-continued

```
Ser His Val Pro Tyr Thr Phe Gly Gly Thr Lys Leu Glu Ile Lys
        100                 105             110

Arg Thr Val Ala Ala Pro Ser Val Phe Ile Phe Pro Pro Ser Asp Glu
        115                 120             125

Gln Leu Lys Ser Gly Thr Ala Ser Val Val Cys Leu Leu Asn Asn Phe
        130                 135             140

Tyr Pro Arg Glu Ala Lys Val Gln Trp Lys Val Asp Asn Ala Leu Gln
145                 150                 155             160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

ANTICOAGULANT ANTIDOTES COMPRISING ANTIBODIES THAT BIND DABIGATRAN AND/OR RELATED COMPOUNDS AND METHODS OF USE THEREOF

SEQUENCE LISTING

The instant application contains a Sequence Listing which has been submitted in ASCII format via EFS-Web and is hereby incorporated by reference in its entirety. Said ASCII copy, created on May 1, 2012, is named BIC-2713.txt and is 56,830 bytes in size.

TECHNICAL FIELD

The present invention pertains to the field of medicine, in particular to the field of anticoagulant therapy.

BACKGROUND INFORMATION

Anticoagulants are substances that prevent coagulation; that is, they stop blood from clotting. Anticoagulants are widely used in human therapy as a medication for thrombotic disorders, for example primary and secondary prevention of deep vein thrombosis, pulmonary embolism, myocardial infarctions and strokes in those who are predisposed.

An important class of oral anticoagulants acts by antagonizing the effects of vitamin K, for example the coumarins which include warfarin. A second class of compounds inhibit coagulation indirectly via a cofactor such as antithrombin III or heparin cofactor II. This includes several low molecular weight heparin products which catalyse the inhibition of predominantly factor Xa (and to a lesser degree thrombin) via antithrombin III (bemiparin, certoparin, dalteparin, enoxaparin, nadroparin, parnaparin, reviparin, tinzaparin), Smaller chain oligosaccharides (fondaparinux, idraparinux) inhibit only factor Xa via antithrombin III. Heparinoids (danaparoid, sulodexide, dermatan sulfate) act via both cofactors and inhibit both factor Xa and thrombin. A third class represents the direct inhibitors of coagulation. Direct factor Xa inhibitors include apixaban, edoxaban, otamixaban, rivaroxaban, and direct thrombin inhibitors include the bivalent hirudins (bivalirudin, lepirudin, desirudin), and the monovalent compounds argatroban and dabigatran.

As blood clotting is a biological mechanism to stop bleeding, a side effect of anticoagulant therapy may be unwanted bleeding events. It is therefore desirable to provide an antidote to be able to stop such anticoagulant-related bleeding events when they occur (Zikria and Ansell, Current Opinion in Hematology 2009, 16(5): 347-356). One way to achieve this is by neutralizing the activity of the anticoagulant compound present in the patient after administration.

Currently available anticoagulant antidotes are protamine (for neutralization of heparin) and vitamin K for neutralization of vitamin K antagonists like warfarin. Fresh frozen plasma and recombinant factor VIIa have also been used as non-specific antidotes in patients under low molecular weight heparin treatment, suffering from major trauma or severe hemorrhage (Lauritzen, B. et al, Blood, 2005, 607A-608A.). Also reported are protamine fragments (U.S. Pat. No. 6,624, 141) and small synthetic peptides (U.S. Pat. No. 6,200,955) as heparin or low molecular weight heparin antidotes; and thrombin muteins (U.S. Pat. No. 6,060,300) as antidotes for thrombin inhibitor. Prothrombin intermediates and derivatives have been reported as antidotes to hirudin and synthetic thrombin inhibitors (U.S. Pat. Nos. 5,817,309 and 6,086, 871). For direct factor Xa inhibitors, inactive factor Xa analogs have been proposed as antidotes (WO2009042962). Furthermore, recombinant factor VIIa has been used to reverse the effect of indirect antithrombin III dependent factor Xa inhibitors such as fondaparinux and idraparinux (Bijsterveld, N R et al, Circulation, 2002, 106: 2550-2554; Bijsterveld, N R et al, British J. of Haematology, 2004 (124): 653-658). A review of methods of anticoagulant reversal is provided in Schulman and Bijsterveld, Transfusion Medicine Reviews 2007, 21(1): 37-48.

International patent application WO2011089183 discloses antibodies that can bind and neutralize the activity of dabigatran.

There is a need to provide improved antidotes for anticoagulant therapy, and in particular to provide antidotes for direct thrombin inhibitors like dabigatran for which no specific antidotes have been disclosed so far.

BRIEF SUMMARY OF THE INVENTION

In one aspect, the present invention relates to an antibody molecule capable of neutralizing the activity of an anticoagulant.

In a further aspect, the antibody molecule has binding specificity for the anticoagulant.

In a further aspect, the anticoagulant is a direct thrombin inhibitor, a Factor Xa inhibitor, or a vitamin K antagonist.

In a further aspect, the anticoagulant is dabigatran, argatroban, melagatran, ximelagatran, hirudin, bivalirudin, lepirudin, desirudin, apixaban, otamixaban, edoxaban, rivaroxaban, defibrotide, ramatroban, antithrombin III, or drotrecogin alpha.

In another aspect, the present invention relates to an antibody molecule against dabigatran, dabigatran exetilate, and/or an O-acylglucuronide of dabigatran.

In a further aspect, the present invention relates to an antibody molecule against dabigatran, dabigatran exetilate, and/or an O-acylglucuronide of dabigatran with reduced immunogenicity in man.

In a further aspect, the present invention relates to an antibody molecule against dabigatran, dabigatran exetilate, and/or an O-acylglucuronide of dabigatran with improved physicochemical properties, in particular improved solubility in aqueous solvents.

In a further aspect, the present invention relates to an antibody molecule against dabigatran, dabigatran exetilate, and/or an O-acylglucuronide of dabigatran with improved produceability in host cells, in particular resulting in improved production yields.

In a further aspect, the antibody molecule is a polyclonal antibody, a monoclonal antibody, a human antibody, a humanized antibody, a chimeric antibody, a fragment of an antibody, in particular a Fab, Fab', or F(ab')$_2$ fragment, a single chain antibody, in particular a single chain variable fragment (scFv), a domain antibody, a nanobody, a diabody, or a DARPin.

In a further aspect, the present invention relates to an antibody molecule as described above for use in medicine.

In a further aspect, the present invention relates to an antibody molecule as described above for use in the therapy or prevention of side effects of anticoagulant therapy.

In a further aspect, the side effect is a bleeding event.

In a further aspect, the present invention relates to a method of treatment or prevention of side effects of anticoagulant therapy, comprising administering an effective amount of an antibody molecule as described above to a patient in need thereof.

In another aspect, the present invention relates to a kit comprising an antibody molecule as described, together with a container and a label.

DETAILED DESCRIPTION OF THE INVENTION

Figure 1:
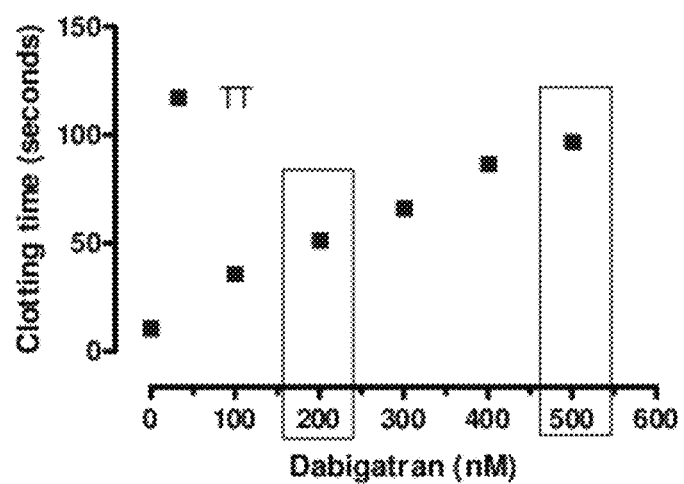
FIG. 1: Increased time to clotting seen with increased concentrations of dabigatran using the thrombin clotting time assay. The 200 nM concentration resulted in an ~5-fold elevation in clotting time over baseline and was used in the first and second set of experiments. The 500 nM concentration (supratherapeutic) was used in the last set of experiments.

In one aspect, the present invention relates to an antibody molecule capable of neutralizing the activity of an anticoagulant.

Antibodies (also known as immunoglobulins, abbreviated Ig) are gamma globulin proteins that can be found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies can bind, by non-covalent interaction, to other molecules or structures known as antigens. This binding is specific in the sense that an antibody will only bind to a specific structure with high affinity. The unique part of the antigen recognized by an antibody is called an epitope, or antigenic determinant.

The part of the antibody binding to the epitope is sometimes called paratope and resides in the so-called variable domain, or variable region (Fv) of the antibody. The variable domain comprises three so-called complementary-determining region (CDR's) spaced apart by framework regions (FR's).

Within the context of this invention, reference to CDR's is based on the definition of Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

The art has further developed antibodies and made them versatile tools in medicine and technology. Thus, in the context of the present invention the terms "antibody molecule" or "antibody" (used synonymously herein) do not only include antibodies as they may be found in nature, comprising e.g. two light chains and two heavy chains, or just two heavy chains as in camelid species, but furthermore encompasses all molecules comprising at least one paratope with binding specificity to an antigen and structural similarity to a variable domain of an immunoglobulin.

Thus, an antibody molecule according to the invention may be a polyclonal antibody, a monoclonal antibody, a human antibody, a humanized antibody, a chimeric antibody, a fragment of an antibody, in particular a Fv, Fab, Fab', or F(ab')$_2$ fragment, a single chain antibody, in particular a single chain variable fragment (scFv), a Small Modular Immunopharmaceutical (SMIP), a domain antibody, a nanobody, a diabody.

Polyclonal antibodies represent a collection of antibody molecules with different amino acid sequences and may be obtained from the blood of vertebrates after immunization with the antigen by processes well-known in the art.

Monoclonal antibodies (mAb or moAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells.". J Immunol Methods 204 (1): 77-87; see also below).

For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to resemble the overall sequence of that variable domain more closely to a sequence of a human variable domain. Methods of chimerisation and -humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". *Nature:* 332:323.).

Furthermore, technologies have been developed for creating antibodies based on sequences derived from the human genome, for example by phage display or using transgenic animals (WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93.; Brüggemann M, Taussig M J. "Production of human antibody repertoires in transgenic mice". Curr Opin Biotechnol. 1997 August; 8(4): 455-8.). Such antibodies are "human antibodies" in the context of the present invention.

Antibody molecules according to the present invention also include fragments of immunoglobulins which retain antigen binding properties, like Fab, Fab', or F(ab')$_2$ fragments. Such fragments may be obtained by fragmentation of immunoglobulins e.g. by proteolytic digestion, or by recombinant expression of such fragments. For example, immunoglobulin digestion can be accomplished by means of routine techniques, e.g. using papain or pepsin (WO 94/29348), or endoproteinase Lys-C (Kleemann, et al, Anal. Chem. 80, 2001-2009, 2008). Papain or Lys-C digestion of antibodies typically produces two identical antigen binding fragments, so-called Fab fragments, each with a single antigen binding site, and a residual Fc fragment. Pepsin treatment yields an F(ab')$_2$. Methods of producing Fab molecules by recombinant expression in host cells are outlined in more detail below.

A number of technologies have been developed for placing variable domains of immunoglobulins, or molecules derived from such variable domains, in a different molecular context. Those should be also considered as "antibody molecules" in accordance with the present invention. In general, these antibody molecules are smaller in size compared to immunoglobulins, and may comprise a single amino acid chain or be composed of several amino acid chains. For example, a single-chain variable fragment (scFv) is a fusion of the variable regions of the heavy and light chains of immunoglobulins, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1): 111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples for antibody-like molecules are immunoglobulin super family antibodies (IgSF; Srinivasan and Roeske, Current Protein Pept. Sci. 2005, 6(2): 185-96). A different concept leads to the so-called Small Modular Immunopharmaceutical (SMIP) which comprises a Fv domain linked to single-chain hinge and effector domains devoid of the constant domain CH1 (WO 02/056910).

In a further aspect, an antibody molecule of the invention may even only have remote structural relatedness to an immunoglobulin variable domain, or no such relation at all, as long as it has a certain binding specificity and affinity comparable to an immunoglobulin variable domain. Such non-immunoglobulin "antibody mimics", sometimes called "scaffold proteins", may be based on the genes of protein A, the lipocalins, a fibronectin domain, an ankyrin consensus repeat domain, and thioredoxin (Skerra, Current Opinion in Biotechnology 2007, 18(4): 295-304). A preferred embodiment in the context of the present invention are designed ankyrin repeat proteins (DARPin's; Steiner et al., J Mol Biol. 2008 Oct. 24; 382(5): 1211-27; Stumpp M T, Amstutz P. Curr Opin Drug Discov Devel. 2007 March; 10(2):153-9).

The antibody molecule may be fused (as a fusion protein) or otherwise linked (by covalent or non-covalent bonds) to other molecular entities having a desired impact on the properties of the antibody molecule. For example, it may be desirable to improve pharmacokinetic properties of antibody molecules, stability e.g. in body fluids such as blood, in particular in the case of single chain antibodies or domain antibodies. A number of technologies have been developed in this regard, in particular to prolong half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258).

In a further aspect, the antibody molecule has binding specificity for the anticoagulant. "Binding specificity" means that the antibody molecule has a significantly higher binding affinity to the anticoagulant than to structurally unrelated molecules.

Affinity is the interaction between a single antigen-binding site on an antibody molecule and a single epitope. It is expressed by the association constant $K_A = k_{ass}/k_{diss}$, or the dissociation constant $K_D = k_{diss}/k_{ass}$.

In one aspect of the invention, the antibody binds to the anticoagulant with an affinity, as determined e.g. by surface plasmon resonance analysis (Malmqvist M., "Surface plasmon resonance for detection and measurement of antibody-antigen affinity and kinetics.", Curr Opin Immunol. 1993 April; 5(2):282-6.), with a $K_D$ value ranging from 0.1 µM to 100 µM, preferably 1 µM to 100 µM, preferably 1 µM to 1 µM. Antibody affinity can also be measured using kinetic exclusion assay (KinExA) technology (Darling, R. J., and Brault P-A., "Kinetic exclusion assay technology: Characterization of Molecular Interactions." ASSAY and Drug Development Technologies. 2004, December 2(6): 647-657).

The binding affinity of an antibody molecule may be enhanced by a process known as affinity maturation (Marks et al., 1992, Biotechnology 10:779-783; Barbas, et al., 1994, Proc. Nat. Acad. Sci, USA 91:3809-3813; Shier et al., 1995, Gene 169:147-155). Affinity matured antibodies are therefore also embraced in the present invention.

In a further aspect of the invention, the antibody molecule is capable of neutralizing the activity of the anticoagulant. That is, upon binding to the antibody molecule, the anticoagulant is no longer able to exert its anticoagulant activity, or exerts this activity at a significantly decreased magnitude. Preferably, the anticoagulant activity is decreased at least 2fold, 5fold, 10fold, or 100fold upon antibody binding, as determined in an activity assay which is appropriate for the anticoagulant at issue, particularly a clotting assay that is sensitive to thrombin, such as the ecarin clotting time or the thrombin clotting time (H. Bounameaux, Marbet G A, Lammle B, et al. "Monitoring of heparin treatment. Comparison of thrombin time, activated partial thromboplastin time, and plasma heparin concentration, and analysis of the behaviour of antithrombin III". American Journal of Clinical Pathology 1980 74(1): 68-72).

For manufacturing the antibody molecules of the invention, the skilled artisan may choose from a variety of methods well known in the art (Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39).

Anticoagulants are well-known in the art, as outlined above. In a further aspect of the invention, the anticoagulant is a direct thrombin inhibitor, a Factor Xa inhibitor, or a vitamin K antagonist. Examples of vitamin K antagonists are the coumarins, which include warfarin. Examples of indirect predominantly factor Xa inhibitors are the heparin group of substances acting through activation of antithrombin III including several low molecular weight heparin products (bemiparin, certoparin, dalteparin, enoxaparin, nadroparin, parnaparin, reviparin, tinzaparin), certain oligosaccharides (fondaparinux, idraparinux), heparinoids (danaparoid, sulodexide, dermatan sulfate), and the direct factor Xa inhibitors (apixaban, otamixaban, rivaroxaban). Examples of thrombin inhibitors include the bivalent hirudins (bivalirudin, lepirudin, desirudin), and the monovalent compounds argatroban and dabigatran.

Thus, in a further aspect, the anticoagulant is dabigatran, argatroban, melagatran, ximelagatran, hirudin, bivalirudin, lepirudin, desirudin, apixaban, edoxaban, otamixaban, rivaroxaban, defibrotide, ramatroban, antithrombin III, or drotrecogin alpha.

A preferred anticoagulant in the context of the present invention is dabigatran (CAS 211914-51-1, N-[2-(4-Amidinophenylaminomethyl)-1-methyl-1H-benzimidazol-5-ylcarbonyl]-N-(2-pyridyl)-beta-alanine) having the chemical formula (II):

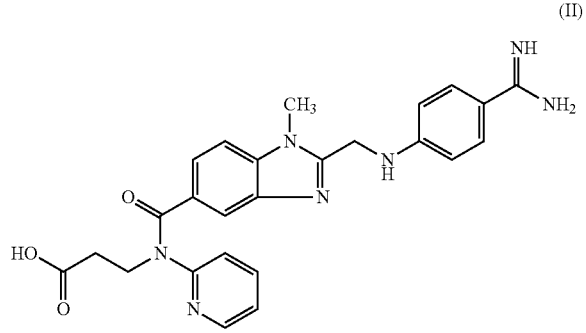 [SMILES: Cn1c(CNc2ccc(C(=N)N)cc2)nc2cc(C(=O)N(CCC(=O)O)c3ccccn3)ccc21]

Dabigatran is known from WO 98/37075, which discloses compounds with a thrombin-inhibiting effect and the effect of prolonging the thrombin time, under the name 1-Methyl-2-[N-(4-amidinophenyl)-aminomethyl]-benzimidazol-5-yl-carboxylic acid-N-(2-pyridyl)-N-(2-hydroxycarbonylethyl)-amide. See also Hauel et al. J Med Chem 2002, 45 (9): 1757-66.

Dabigatran is applied as a prodrug of formula (III):

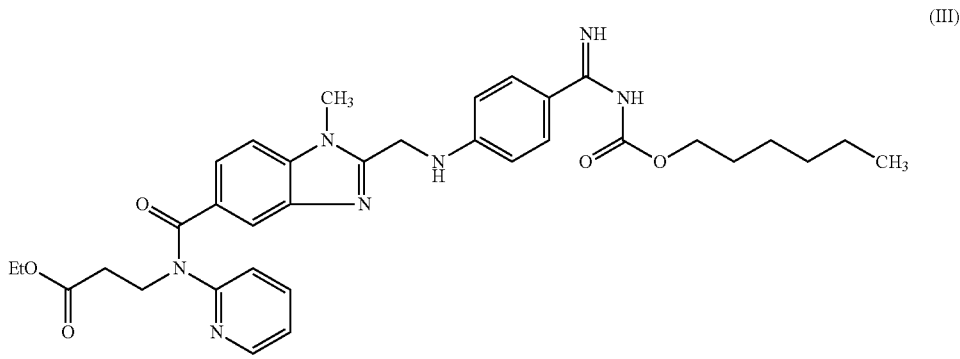 [SMILES: CCCCCCOC(=O)NC(=N)c1ccc(NCc2nc3cc(C(=O)N(CCC(=O)OCC)c4ccccn4)ccc3n2C)cc1]

The compound of formula III (named dabigatran etexilate, CAS 211915-06-9; ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate) is converted into the active compound (II) after entering the body. A preferred polymorph of dabigatran etexilate is dabigatran etexilate mesylate.

The main indications for dabigatran are the post-operative prevention of deep-vein thrombosis, the treatment of established deep vein thrombosis and the prevention of strokes in patients with atrial fibrillation (Eriksson et al., Lancet 2007, 370 (9591): 949-56; Schulman S et al, N Engl J Med 2009, 361 (24): 2342-52; Connolly S et al., N Engl J Med 2009, 361 (12): 1139-51; Wallentin et al., Lancet 2010, 376 (9745): 975-983).

In the human body, glucuronidation of the carboxylate moiety is the major human metabolic pathway of dabigatran (Ebner et al., Drug Metab. Dispos. 2010, 38(9):1567-75). It results in the formation of the 1-O-acylglucuronide (beta anomer). The 1-O-acylglucuronide, in addition to minor hydrolysis to the aglycon, may undergo nonenzymatic acyl migration in aqueous solution, resulting in the formation of the 2-O—, 3-O—, and 4-O-acylglucuronides. Experiments with the purified 1-O-acylglucuronide and its isomeric rearrangement products revealed equipotent prolongation of the activated partial thromboplastin time compared with dabigatran.

In another aspect of the invention, the antibody molecule binds both to dabigatran and dabigatran etexilate.

In another aspect of the invention, the antibody molecule binds both to dabigatran and O-acylglucuronides of dabigatran, in particular the 1-O-acylglucuronide of dabigatran.

In another aspect of the invention, the antibody molecule binds furthermore to the 2-O—, 3-O—, and 4-O-acylglucuronides of dabigatran.

In another aspect of the invention, the antibody molecule is capable of neutralizing the activity of dabigatran and O-acylglucuronides of dabigatran, in particular the 1-O-acylglucuronide of dabigatran.

In the following, references to SEQ ID NOs. refer to the sequences of Table 1 and the sequence listing which is part of this application, unless indicated otherwise.

In another aspect of the invention, the antibody molecule has binding specificity for dabigatran and comprises a heavy chain variable domain with a CDR1 selected from the group consisting of SEQ ID NO: 1, 7, 13, 19, 25, 31, 37, 43, 49, 55, 61, and 67, a CDR2 selected from the group consisting of SEQ ID NO: 2, 8, 14, 20, 26, 32, 38, 44, 50, 56, 62, and 68, and a CDR3 selected from the group consisting of SEQ ID NO: 3, 9, 15, 21, 27, 33, 39, 45, 51, 57, and 63, and a light chain variable domain with a CDR1 selected from the group consisting of SEQ ID NO: 4, 10, 16, 22, 28, 34, 40, 46, 52, 58, and 64, a CDR2 selected from the group consisting of SEQ ID NO: 5, 11, 17, 23, 29, 35, 41, 47, 53, 59, and 65, and a CDR3 selected from the group consisting of SEQ ID NO: 6, 12, 18, 24, 30, 36, 42, 48, 54, 60, 66, and 69.

In another aspect of the invention, the antibody molecule has binding specificity for dabigatran and comprises a heavy chain variable domain with a CDR1 of SEQ ID NO: 1, a CDR2 of SEQ ID NO: 2, and a CDR3 of SEQ ID NO: 3, and a light chain variable domain with a CDR1 of SEQ ID NO: 4, a CDR2 of SEQ ID NO: 5, and a CDR3 of SEQ ID NO: 6.

In another aspect of the invention, the antibody molecule has binding specificity for dabigatran and comprises a heavy chain variable domain with a CDR1 of SEQ ID NO: 7, a CDR2 of SEQ ID NO: 8, and a CDR3 of SEQ ID NO: 9, and a light chain variable domain with a CDR1 of SEQ ID NO: 10, a CDR2 of SEQ ID NO: 11, and a CDR3 of SEQ ID NO: 12.

In another aspect of the invention, the antibody molecule has binding specificity for dabigatran and comprises a heavy chain variable domain with a CDR1 of SEQ ID NO: 13, a CDR2 of SEQ ID NO: 14, and a CDR3 of SEQ ID NO: 15, and a light chain variable domain with a CDR1 of SEQ ID NO: 16, a CDR2 of SEQ ID NO: 17, and a CDR3 of SEQ ID NO: 18.

In another aspect of the invention, the antibody molecule has binding specificity for dabigatran and comprises a heavy chain variable domain with a CDR1 of SEQ ID NO: 19, a CDR2 of SEQ ID NO: 20, and a CDR3 of SEQ ID NO: 21, and a light chain variable domain with a CDR1 of SEQ ID NO: 22, a CDR2 of SEQ ID NO: 23, and a CDR3 of SEQ ID NO: 24.

In another aspect of the invention, the antibody molecule has binding specificity for dabigatran and comprises a heavy chain variable domain with a CDR1 of SEQ ID NO: 25, a CDR2 of SEQ ID NO: 26, and a CDR3 of SEQ ID NO: 27, and a light chain variable domain with a CDR1 of SEQ ID NO: 28, a CDR2 of SEQ ID NO: 29, and a CDR3 of SEQ ID NO: 30.

In another aspect of the invention, the antibody molecule has binding specificity for dabigatran and comprises a heavy chain variable domain with a CDR1 of SEQ ID NO: 31, a CDR2 of SEQ ID NO: 32, and a CDR3 of SEQ ID NO: 33, and a light chain variable domain with a CDR1 of SEQ ID NO: 34, a CDR2 of SEQ ID NO: 35, and a CDR3 of SEQ ID NO: 36.

In another aspect of the invention, the antibody molecule has binding specificity for dabigatran and comprises a heavy chain variable domain with a CDR1 of SEQ ID NO: 37, a CDR2 of SEQ ID NO: 38, and a CDR3 of SEQ ID NO: 39, and a light chain variable domain with a CDR1 of SEQ ID NO: 40, a CDR2 of SEQ ID NO: 41, and a CDR3 of SEQ ID NO: 42.

In another aspect of the invention, the antibody molecule has binding specificity for dabigatran and comprises a heavy chain variable domain with a CDR1 of SEQ ID NO: 43, a CDR2 of SEQ ID NO: 44, and a CDR3 of SEQ ID NO: 45, and a light chain variable domain with a CDR1 of SEQ ID NO: 46, a CDR2 of SEQ ID NO: 47, and a CDR3 of SEQ ID NO: 48.

In another aspect of the invention, the antibody molecule has binding specificity for dabigatran and comprises a heavy chain variable domain with a CDR1 of SEQ ID NO: 49, a CDR2 of SEQ ID NO: 50, and a CDR3 of SEQ ID NO: 51, and a light chain variable domain with a CDR1 of SEQ ID NO: 52, a CDR2 of SEQ ID NO: 53, and a CDR3 of SEQ ID NO: 54.

In another aspect of the invention, the antibody molecule has binding specificity for dabigatran and comprises a heavy chain variable domain with a CDR1 of SEQ ID NO: 55, a CDR2 of SEQ ID NO: 56, and a CDR3 of SEQ ID NO: 57, and a light chain variable domain with a CDR1 of SEQ ID NO: 58, a CDR2 of SEQ ID NO: 59, and a CDR3 of SEQ ID NO: 60.

In another aspect of the invention, the antibody molecule has binding specificity for dabigatran and comprises a heavy chain variable domain with a CDR1 of SEQ ID NO: 61, a CDR2 of SEQ ID NO: 62, and a CDR3 of SEQ ID NO: 63, and a light chain variable domain with a CDR1 of SEQ ID NO: 64, a CDR2 of SEQ ID NO: 65, and a CDR3 of SEQ ID NO: 66.

In another aspect of the invention, the antibody molecule has binding specificity for dabigatran and comprises a heavy chain variable domain with a CDR1 of SEQ ID NO: 67, a CDR2 of SEQ ID NO: 68, and a CDR3 of SEQ ID NO: 9, and a light chain variable domain with a CDR1 of SEQ ID NO: 64, a CDR2 of SEQ ID NO: 65, and a CDR3 of SEQ ID NO: 69.

In another aspect of the invention, the antibody molecule comprises a heavy chain variable domain of SEQ ID NO: 70, and a light chain variable domain of SEQ ID No: 71.

In another aspect of the invention, the antibody molecule comprises a heavy chain variable domain of SEQ ID NO: 72, and a light chain variable domain of SEQ ID No: 73.

In another aspect of the invention, the antibody molecule comprises a heavy chain variable domain of SEQ ID NO: 74, and a light chain variable domain of SEQ ID No: 75.

In another aspect of the invention, the antibody molecule comprises a heavy chain variable domain of SEQ ID NO: 76, and a light chain variable domain of SEQ ID No: 77.

In another aspect of the invention, the antibody molecule comprises a heavy chain variable domain of SEQ ID NO: 78, and a light chain variable domain of SEQ ID No: 79.

In another aspect of the invention, the antibody molecule comprises a heavy chain variable domain of SEQ ID NO: 80, and a light chain variable domain of SEQ ID No: 81.

In another aspect of the invention, the antibody molecule comprises a heavy chain variable domain of SEQ ID NO: 82, and a light chain variable domain of SEQ ID No: 83.

In another aspect of the invention, the antibody molecule comprises a heavy chain variable domain of SEQ ID NO: 84, and a light chain variable domain of SEQ ID No: 85.

In another aspect of the invention, the antibody molecule comprises a heavy chain variable domain of SEQ ID NO: 86, and a light chain variable domain of SEQ ID No: 87.

In another aspect of the invention, the antibody molecule comprises a heavy chain variable domain of SEQ ID NO: 88, and a light chain variable domain of SEQ ID No: 89.

In another aspect of the invention, the antibody molecule comprises a heavy chain variable domain of SEQ ID NO: 90, and a light chain variable domain of SEQ ID No: 91.

In another aspect of the invention, the antibody molecule comprises a heavy chain variable domain of SEQ ID NO: 92, and a light chain variable domain of SEQ ID No: 93.

In another aspect of the invention, the antibody molecule comprises a heavy chain variable domain of SEQ ID NO: 92, and a light chain variable domain of SEQ ID No: 94.

In another aspect of the invention, any one of the aforementioned light chain variable domains is fused to a constant domain of SEQ ID NO: 97.

In another aspect of the invention, any one of the aforementioned heavy chain variable domains is fused to a constant domain of SEQ ID NO: 98.

In another aspect of the invention, the antibody molecule comprises a heavy chain of SEQ ID NO: 95, and a light chain of SEQ ID No: 96.

In certain aspects, the invention concerns antibodies against dabigatran which have a high solubility in aqeous media and a low tendency of aggregation.

In another aspect of the invention, the antibody molecule is a scFv molecule. In this format, the variable domains disclosed herein may be fused to each other with a suitable linker peptide. The construct may comprise these elements in the order, from N terminus to C terminus, (heavy chain variable domain)-(linker peptide)-(light chain variable domain), or (light chain variable domain)-(linker peptide)-(heavy chain variable domain).

Processes are known in the art which allow recombinant expression of nucleic acids encoding sFv constructs in host cells (like *E. coli, Pichia pastoris*, or mammalian cell lines, e.g. CHO or NSO), yielding functional scFv molecules (see e.g. Rippmann et al., Applied and Environmental Microbiology 1998, 64(12): 4862-4869; Yamawaki et al., J. Biosci. Bioeng. 2007, 104(5): 403-407; Sonoda et al., Protein Expr. Purif. 2010, 70(2): 248-253).

In particular, the scFv antibody molecules of the invention can be produced as follows. The constructs can be expressed in different *E. coli* strains like W3110, TG1, BL21, BL21 (DE3), HMS174, HMS174(DE3), MM294 under control of an inducible promoter. This promoter can be chosen from lacUV5, tac, T7, trp, trc, T5, araB. The cultivation media are preferably fully defined according to Wilms et al., 2001 (Wilms et al., Biotechnology and Bioengineering 2001, 73(2): 95-103), DeLisa et al., 1999 (DeLisa et al., Biotechnology and Bioengineering 1999, 65(1): 54-64) or equivalent. However, supplementation of the batch medium and/or feed medium with amino acids such as isoleucine, leucine, lysine, methionine, phenylalanine, threonine, tryptophan and valin or complex media components such as soy peptone or yeast extract may be beneficial. The process for fermentation is performed in a fed-batch mode. Conditions: Temperature 20-40° C., pH 5.5-7.5, DO is kept above 20%. After consumption of the initial carbon source the culture is fed with the feed media stated above (or equivalent). When a dry cell weight of 40 to 100 g/L is reached in the fermenter the culture is induced with an appropriate inducer corresponding to the used promoter system (e.g. IPTG, lactose, arabinose). The induction can either be performed as a pulsed full induction or as a partial induction by feeding the respective inducer into the fermenter over a prolonged time or a combination thereof. The production phase should last 4 hours at least. The cells are recovered by centrifugation in bowl centrifuges, tubular bowl centrifuges or disc stack centrifuges, the culture supernatant is discarded.

The E. coli cell mass is resuspended in 4- to 8-fold amount of lysis buffer (phosphate or Tris buffer, pH 7-8.5). Cell lysis. is preferably performed by high pressure homogenization followed by recovery of the pellet by centrifugation in bowl, tubular bowl or disc stack centrifuges. Pellet containing scFv inclusion bodies is washed 2-3 times with 20 mM Tris, 150 mM NaCl, 5 mM EDTA, 2 M Urea, 0.5% Triton X-100, pH 8.0 followed by two wash steps using 20 mM Tris, 150 mM NaCl, 5 mM EDTA, pH 8.0. scFv inclusion bodies are finally recovered by centrifugation in bowl, tubular bowl or disc stack centrifuges. Solubilisation of scFv inclusion bodies can be performed in 100 mM Glycine/NaOH, 5 mM EDTA, 20 mM dithiothreitol, pH 9.5-10.5 containing chaotropic agents such as 6 M Guanidine-HCl or 8-10 mM Urea. After incubation for 30-60 minutes solution is centrifuged and supernatant containing the target protein recovered for subsequent refolding. Refolding is preferably performed in fed batch mode by diluting the protein solution 1:10-1:50 in refolding buffer to a final protein concentration of 0.1-0.5 mg/ml. Refolding buffer can contain 50-100 mM Tris and/or 50-100 mM Glycine, 50-150 mM NaCl, 1-3 M urea, 0.5-1 M arginine, 2-6 mM of redox system such as e.g. cytein/cystine or oxidized/reduced glutathione, pH 9.5-10.5. After incubation for 24-72 h at 4° C. refolding solution is optionally filtrated using a 0.22 μm filter, diluted and pH adjusted to pH 7.0-8.0. Protein is separated via cation exchange chromatography in binding mode (e.g. Toyopearl GigaCap S-650M, SP Sepharose FF or S HyperCel™) at pH 7.0-8.5. Elution is performed by a linear increasing NaCl gradient. Fractions containing the target protein are pooled and subsequently separated on anion exchange column in non-binding mode (e.g. Toyopearl GigaCap Q-650M, Q-Sepharose FF, Q HyperCel™) followed by a cation exchange polishing step (eg. SP Sepharose HP). Fractions containing the target protein with a purity level of minimally 90% are pooled and formulated by diafiltration or size exclusion chromatography in PBS. Identity and product quality of the produced scFv molecule are analysed by reducing SDS-PAGE where the scFv can be detected in one major band of approx. 26 kDa. Further assays for characterization of the scFv include mass spectrometry, RP-HPLC and SE-HPLC.

In another aspect of the invention, the antibody molecule is a Fab molecule. In that format, the variable domains disclosed above may each be fused to an immunoglobulin constant domain, preferably of human origin. Thus, the heavy chain variable domain may be fused to a $CH_1$ domain (a so-called Fd fragment), and the light chain variable domain may be fused to a CL domain.

In another aspect of the invention, the antibody molecule comprises a heavy chain of SEQ ID NO: 99, and a light chain of SEQ ID No: 100. Preferably, the antibody molecule is a Fab molecule.

In another aspect of the invention, the antibody molecule comprises a heavy chain of SEQ. ID NO: 99, and a light chain of SEQ ID No: 101. Preferably, the antibody molecule is a Fab molecule.

In another aspect of the invention, the antibody molecule is a Fab molecule which consists of a heavy chain of SEQ ID NO: 99, and a light chain of SEQ ID No: 100.

In another aspect of the invention, the antibody molecule is a Fab molecule which consists of a heavy chain of SEQ ID NO: 99, and a light chain of SEQ ID No: 101.

Nucleic acids encoding Fab constructs may be used to express such heavy and light chains in host cells, like E. coli, Pichia pastoris, or mammalian cell lines (e.g. CHO, or NS0). Processes are known in the art which allow proper folding, association, and disulfide bonding of these chains into functional Fab molecules comprising a Fd fragment and a light chain (Burtet et al., J. Biochem. 2007, 142(6), 665-669; Ning et al., Biochem. Mol. Biol. 2005, 38: 204-299; Quintero-Hernandez et al., Mol. Immunol. 2007, 44: 1307-1315; Willems et al. J. Chromatogr. B. Analyt. Technol. Biomed. Life Sci. 2003; 786:161-176.).

In particular, Fab molecules of the invention can be produced in CHO cells as follows. CHO-DG44 cells (Urlaub, G., Kas, E., Carothers, A. M., and Chasin, L. A. (1983). Deletion of the diploid dihydrofolate reductase locus from cultured mammalian cells. Cell 33, 405-412.) growing in suspension in serum-free medium are transfected with expression constructs encoding heavy and light chain of the Fab molecule using Lipofectamine™ and Plus™ reagent (Invitrogen) according to the manufacturer's instructions. After 48 hours, the cells are subjected to selection in medium containing 200 μg/mL of the antibiotic G418 and without hypoxanthine and thymidine to generate stably transfected cell populations. These stable transfectants are subsequently subjected to gene amplification by adding methotrexate (MTX) in increasing concentrations (up to 100 or 400 nM) into the culture medium. Once the cells have adapted, they are subjected to fed-batch fermentations over 10 to 11 days to produce Fab protein material.

Suspension cultures of CHO-DG44 cells and stable transfectants thereof are incubated in chemically defined, serum-free cultivation media. Seed stock cultures are sub-cultivated every 2-3 days with seeding densities of $3 \times 10^5$-$2 \times 10^5$ cells/mL respectively. Cells are grown in shake flasks in Multitron HT incubators (Infors) at 5% $CO_2$, 37° C. and 120 rpm. For fed-batch experiments, cells are seeded at $3 \times 10^5$ cells/mL into shake flasks in BI-proprietary production medium without antibiotics or MTX. The cultures are agitated at 120 rpm in 37° C. and 5% $CO_2$ which is later reduced to 2% as cell numbers increase. Culture parameters including cell count, viability, pH, glucose and lactate concentrations are determined daily and pH is adjusted to pH 7.0 using carbonate as needed. BI-proprietary feed solution is added every 24 hrs. Samples from the supernatant are taken at different time points to determine the Fab product concentration by ELISA. After 10 to 11 days, the cell culture fluid is harvested by centrifugation and transferred to the purification labs.

The Fab molecule is purified from the supernatant of the fed-batch cultures by means of chromatography and filtration. As primary capture step affinity chromatography, e.g. Protein G or Protein L, are applied. Alternatively, in case of low binding affinities and capacities, the Fab is captured by cation exchange chromatography (CEX) exploiting the pI of the molecule. Host cell proteins and contaminants, e.g. DNA or viruses, are removed by additional orthogonal purification steps.

Identity and product quality of the produced Fab molecule are analysed by electrophoretic methods, e.g. SDS-PAGE, by which Fab can be detected as one major band of approx. 50 kDa. Further assays for characterization of the Fab product include mass spectrometry, isoelectric focusing and size exclusion chromatography. Binding activity is followed by BIAcore analysis.

Quantification of Fab or full-length IgG molecules in the supernatant of the cell cultures is performed via sandwich enzyme linked immunosorbent assay (ELISA). The full-length IgG can be detected using antibodies raised against human-Fc fragment (Jackson Immuno Research Laboratories) and human kappa light chain (peroxidase-conjugated, Sigma). The Fab fragment is immobilized by goat polyclonal anti-Human IgG (H and L, Novus) and detected by sheep polyclonal antibodies raised against human IgG. (peroxidase-conjugated, The Binding Site).

Fab molecules can also be generated from full-length antibody molecules by enzymatic cleavage. The advantage of this approach is that platform processes for robust and efficient fermentation and purification are applicable which are amenable for up-scaling and high yields at the desired product quality. For purification affinity chromatography using a recombinant Protein A resin can be used as primary capture step which usually results in high purities.

For this purpose, the heavy chain encoding Fab sequences are fused to the Fc-region of a human IgG antibody molecule. The resulting expression constructs are then transfected into CHO-DG44 cells growing in suspension in serum-free medium using lipofection. After 48 hours, the cells are subjected to selection in medium containing 200 µg/mL of the antibiotic G418 and without hypoxanthine and thymidine to generate stably transfected cell populations. These stable transfectants are subsequently subjected to gene amplification by adding methotrexate (MTX) in increasing concentrations (up to 100 or 400 nM) into the culture medium. Once the cells have adapted, they are subjected to fed-batch fermentations over 10 to 11 days to produce IgG protein material.

The IgG protein is purified from the culture supernatant by using recombinant Protein A-affinity chromatography. To obtain the desired neutralizing Fab fragment the full-length IgG is then incubated in the presence of papain which cleaves the IgG within the hinge region, thereby releasing two Fab fragments and the Fc-moiety.

The Fab molecule is isolated by affinity chromatography, e.g. Protein G or Protein L. Alternatively, in case of low binding affinities and capacities, the Fab is captured by cation exchange chromatography (CEX) exploiting the pI of the molecule. Host cell proteins and contaminants, e.g. Papain, DNA or viruses, are removed by additional orthogonal purification steps.

In another aspect of the invention, the antibody molecule is an amino acid sequence variant of an antibody molecule as described herein.

Amino acid sequence variants of antibodies can be prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletions, insertions, and substitutions is made to arrive at the final construct, provided that the final construct possesses the desired characteristics. The amino acid changes also may alter post-translational processes of the humanized or variant antibody, such as changing the number or position of glycosylation sites.

A useful method for identification of certain residues or regions of the antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody fused to an epitope tag. Other insertional variants of the antibody molecule include a fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the Table below under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human Dabigatran. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an antibody molecule as described herein. As outlined above, the antigen of the antibody molecule of the invention is an anticoagulant. The antigen is used to generate the antibody molecule, either by immunization of an animal, or by selecting antibody sequences from sequence libraries, as with phage display methods.

Immunization protocols for animals are well-known in the art. To achieve a proper immune response, it may be necessary to combine the antigen with an adjuvant, like aluminium phosphate, aluminium hydroxide, squalene, or Freund's complete/incomplete adjuvant. The antigens in the context of the present invention, like dabigatran, are mostly comparably small organic molecules, which sometimes do not stimulate antibody formation upon administration to an animal. It may therefore be necessary to attach the antigen to a macromolecule, as a hapten.

In a further aspect, the present invention relates to an antibody molecule as described above for use in medicine.

In a further aspect, the present invention relates to a pharmaceutical composition comprising an antibody molecule as described before, and a pharmaceutical carrier.

To be used in therapy, the antibody molecule is included into pharmaceutical compositions appropriate to facilitate administration to animals or humans. Typical formulations of the antibody molecule can be prepared by mixing the antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function.

In one aspect, the pharmaceutical composition comprises the antibody molecule in an aqueous, buffered solution at a concentration of 10-20 mg/ml, or a lyophilisate made from such a solution.

The preferred mode of application is parenteral, by infusion or injection (intraveneous, intramuscular, subcutaneous, intraperitoneal, intradermal), but other modes of application such as by inhalation, transdermal, intranasal, buccal, oral, may also be applicable.

In a further aspect, the present invention relates to an antibody molecule as described above for use in the therapy or prevention of side effects of anticoagulant therapy, in particular bleeding events.

In a further aspect, the present invention relates to the use of an antibody molecule as described herein for the manufacture of a medicament for the treatment or prevention of a disease or disorder as described herein, in particular the side effects of anticoagulant therapy.

In a further aspect, the present invention relates to an antibody molecule as described above for use in the reversal of an overdosing of an anticoagulant, in particular dabigatran or dabigatran exetilate.

In a further aspect, the present invention relates to an antibody molecule as described above for use as an antidote of an anticoagulant, in particular dabigatran or dabigatran exetilate.

In a further aspect, the present invention relates to a method of treatment or prevention of side effects of anticoagulant therapy, comprising administering an effective amount of an antibody molecule as described above to a patient in need thereof.

In a further aspect, the present invention relates to a method of treatment of an overdosing event in anticoagulant therapy, comprising administering an effective amount of an antibody molecule as described above to a patient in need thereof.

In a further aspect, the present invention relates to a method for reducing the concentration of dabigatran or 1-O-acylglucuronide of dabigatran in plasma of a patient being treated with dabigatran, dabigatran etexilate, a prodrug of dabigatran or a pharmaceutically acceptable salt thereof, comprising the step of administering a reversal agent that neutralizes the activity of dabigatran or 1-O-acylglucuronide in the patient.

In a further aspect, the present invention relates to a reversal agent that neutralizes the activity of dabigatran or 1-O-acylglucuronide for use in a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures.

In a further aspect, the present invention relates to a method for reducing the concentration of dabigatran or 1-O-acylglucuronide of dabigatran in plasma of a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures, comprising the step of administering a reversal agent that neutralizes the activity of dabigatran or 1-O-acylglucuronide in the patient.

In a further aspect, the present invention relates to a method of reversal of the anticoagulant effect of dabigatran or 1-O-acylglucuronide of dabigatran in a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures, comprising the step of administering a reversal agent that neutralizes the activity of dabigatran or 1-O-acylglucuronide in the patient.

In a preferred embodiment, the reversal agent is an antibody molecule against dabigatran which is capable of neutralizing the anticoagulant activity of dabigatran, dabigatran etexilate, and/or 1-O-acylglucuronide. In another preferred embodiment, the reversal agent is an antibody molecule against dabigatran as described herein.

Preferably, the concentration of dabigatran or 1-O-acylglucuronide of dabigatran in plasma is greater than 0 nM but less than 1000 µM and wherein the reversal agent used to neutralize the activity of dabigatran or 1-O-acylglucuronide is present in a stoichiometric amount of dabigatran or 1-O-acylglucuronide of dabigatran to reversal agent.

In a further aspect, the concentration of dabigatran or 1-O-acylglucuronide of dabigatran in plasma is greater than 0 nM but less than 1000 µM, and wherein the reversal agent used to neutralize the activity of dabigatran or 1-O-acylglucuronide is present in a molar ratio of between 1:1 and 1:100 of dabigatran or 1-O-acylglucuronide of dabigatran to reversal agent.

In a further aspect, the concentration of dabigatran or 1-O-acylglucuronide of dabigatran in plasma is between 30 nM and 1000 µM, and wherein the reversal agent used to neutralize the activity of dabigatran or 1-O-acylglucuronide is present in a ratio of between 30 nM and 1000 µM of dabigatran or 1-O-acylglucuronide of dabigatran to reversal agent.

In another aspect, the present invention relates to a method for reversing or reducing the activity of dabigatran or 1-O-acylglucuronide of dabigatran in a patient experiencing bleeding or at risk for bleeding due to an impaired clotting ability or trauma, comprising the steps of:
  (a) determining the amount of dabigatran or 1-O-acylglucuronide of dabigatran present in the patient;
  (b) administering an effective amount of an agent to reverse or reduce the activity of dabigatran or 1-O-acylglucuronide of dabigatran determined in the patient; and
  (c) monitoring a thrombin clotting time of the patient to ensure a reversal or reduction in activity of dabigatran or 1-O-acylglucuronide of dabigatran has been reached.

In a preferred aspect, the reversal of activity of dabigatran or 1-O-acylglucuronide of dabigatran is 100%. In a further preferred aspect, the reduction of activity of dabigatran or 1-O-acylglucuronide of dabigatran is between 10 and 99% of dabigatran or 1-O-acylglucuronide of dabigatran in the patient.

The "therapeutically effective amount" of the antibody to be administered is the minimum amount necessary to prevent, ameliorate, or treat the side effects of anticoagulant therapy, in particular the minimum amount which is effective to stop bleeding. This can be achieved with stoichiometric amounts of antibody molecule.

Dabigatran, for example, may achieve a plasma concentration in the magnitude of 200 nM when given at the recommended dose. When a monovalent antibody molecule with a molecular weight of ca. 50 kD is used, neutralization may be achieved for example at a dose of about 1 mg/kg, when given intravenously as a bolus. In another embodiment, the dose of a Fab molecule applied to a human patient may be 50-1000 mg per application, for example 100, 200, 500, 750, or 1000 mg. Depending on the situation, e.g. when dabigatran has been overdosed in a patient, it may be adequate to apply an even higher dose, e.g. 1250, 1500, 1750 or 2000 mg per application. The appropriate dose may be different, depending on the type and dose of anticoagulant administered; the time elapsed since such administration, the nature of the antigen molecule, the condition of the patient, and other factors. The skilled expert knows methods to establish doses which are both therapeutically effective and safe.

In a further aspect, the present invention relates to an antibody molecule with binding affinity to dabigatran and/or dabigatran etexilate. Preferably, the antibody molecule binds to the dabigatran and/or dabigatran etexilate with an affinity, as determined e.g. by surface plasmon resonance analysis (Malmqvist M., "Surface plasmon resonance for detection and measurement of antibody-antigen affinity and kinetics." Curr Opin Immunol. 1993 April; 5(2):282-6.) or kinetic exclusion assay (KinExA) technology (Darling, R. J., and Brault P-A., "Kinetic exclusion assay technology: Characterization of Molecular Interactions." ASSAY and Drug Development Technologies. 2004, December 2(6): 647-657), with a $K_D$ value ranging from 0.1 µM to 100 µM, preferably 1 µM to 100 µM, more preferably 1 µM to 1 µM.

The antibody molecules of the invention can also be used for analytical and diagnostic procedures, for example to determine antigen concentration in samples such as plasma, serum, or other body fluids. For example, the antigen molecules may be used in an enzyme-linked immunoadsorbent assay (ELISA), like those described in the examples. Thus, in a further aspect, the present invention relates to analytical and diagnostic kits comprising antibody molecules a described herein, and to respective analytical and diagnostic methods.

In a further aspect, the present invention relates to a method of manufacturing an antibody molecule of any one of the preceding claims, comprising
  (a) providing a host cell comprising one or more nucleic acids encoding said antibody molecule in functional association with an expression control sequence,
  (b) cultivating said host cell, and
  (c) recovering the antibody molecule from the cell culture.

The invention further provides an article of manufacture and kit containing materials useful for neutralization of oral anticoagulants, particularly direct thrombin inhibitors. The article of manufacture comprises a container with a label. Suitable containers include, for example, bottles, vials, and test tubes. The containers may be formed from a variety of materials such as glass, metal, plastic or combinations thereof. The container holds a pharmaceutical composition comprising the antibody described herein or dabigatran, dabigatran etexilate, a prodrug of dabigatran or a pharmaceutically acceptable salt thereof. The active agent in the pharmaceutical composition is the particular antibody or dabigatran, dabigatran etexilate, a prodrug of dabigatran or a pharmaceutically acceptable salt thereof. The label on the container of the antibody indicates that the pharmaceutical composition is used for neutralizing or partially neutralizing dabigatran, dabigatran etexilate, a prodrug of dabigatran or a pharmaceutically acceptable salt thereof in vivo.

The kit of the invention comprises one or more of the containers described above. It may further include other materials desirable from a commercial and user standpoint, including other buffers, diluents, filters, needles, syringes, and package inserts with instructions for use.

In one embodiment of the invention, the kit comprises an antibody of any one the antibodies described herein or a pharmaceutical composition thereof. For example, the kit may comprise (1) any one the antibodies described herein or a pharmaceutical composition thereof, (2) a container and (3) a label.

In another embodiment, the kit comprises an antibody of any one the antibodies described herein or a pharmaceutical composition thereof, and dabigatran, dabigatran etexilate, a prodrug of dabigatran or a pharmaceutically acceptable salt thereof. The form of dabigatran, dabigatran etexilate, a prodrug of dabigatran or a pharmaceutically acceptable salt thereof may be in the form of a solid, liquid or gel. In a preferred embodiment, the pharmaceutically acceptable salt of dabigatran etexilate is a mesylate salt. In yet another preferred embodiment, the strength per dosage unit of the dabigatran, dabigatran etexilate, prodrug of dabigatran or pharmaceutically acceptable salt thereof is between about 50 mg and about 400 mg, about 75 mg and about 300 mg, about 75 mg and 150 mg, or about 110 mg and about 150 mg, given once-a-day (OD) or twice-a-day (BID). For example, the kit may comprise (1) any one the antibodies described herein or a pharmaceutical composition thereof, (2) a pharmaceutical composition of dabigatran, dabigatran etexilate, a prodrug of dabigatran or a pharmaceutically acceptable salt thereof, (3) a container and (4) a label.

In an alternate embodiment, the kit comprises (1) a first pharmaceutical composition comprising dabigatran, dabigatran etexilate, a prodrug of dabigatran or a pharmaceutically acceptable salt thereof, (2) a second pharmaceutical composition comprising any one the antibodies described herein or combination thereof, (3) instructions for separate administration of said first and second pharmaceutical compositions to a patient, wherein said first and second pharmaceutical compositions are contained in separate containers and said second pharmaceutical composition is administered to a patient requiring neutralization or partial neutralization of dabigatran or 1-O-acylglucuronide of dabigatran.

The invention also provides a diagnostic method to neutralize or partially neutralize dabigatran or 1-O-acylglucuronide of dabigatran in a patient being treated with dabigatran, dabigatran etexilate, a prodrug of dabigatran or a pharmaceutically acceptable salt thereof, comprising administering any one of the antibodies described herein, a combination thereof or a pharmaceutical composition thereof. Specifically, the invention provides a method for neutralizing or partially neutralizing dabigatran or 1-O-acylglucuronide of dabigatran in a patient comprising the steps of (a) confirming that a patient was being treated with dabigatran, dabigatran etexilate, a prodrug of dabigatran or a pharmaceutically acceptable salt thereof, and the amount that was taken by the patient; (b) neutralizing dabigatran or 1-O-acylglucuronide with any one of the antibodies described herein or combination thereof prior to performing a clotting or coagulation test or assay wherein dabigatran or the 1-O-acylglucuronide of dabigatran would interfere with the accurate read out of the test or assay results; (c) performing the clotting or coagulation test or assay on a sample taken from the patient to determine the level of clot formation without dabigatran or 1-O-acylglucuronide of dabigatran present; and (d) adjusting an amount of dabigatran, dabigatran etexilate, a prodrug of dabigatran or a pharmaceutically acceptable salt thereof administered to the patient in order to achieve the appropriate balance between clot formation and degradation in a patient. The molar ratio of antibody to dabigatran or 1-O-acylglucuronide of dabigatran is in the molar ratio of between 0.1 and 100, preferably between 0.1 and 10. The accurate read out of the test or assay result may be an accurate read out of fibrinogen levels, activated protein C resistance or related tests.

EXAMPLES

I. Production of Polyclonal Anti-Dabigatran Antibodies

For the production of polyclonal anti-dabigatran antibodies, 3 different immunogens were produced with two different haptens and different molar input ratios of the hapten and the carrier protein (BSA).

For the screening, an enzyme horseradish peroxidase (HRP)-conjugate was produced and an enzyme-immunosorbent assay (ELISA) developed.

Further purification of the polyclonal antibodies was performed by affinity chromatography on protein A sepharose FF.

1. Materials and Methods

Test Compound (Dabigatran)

Code: dabigatran, zwitter ion

Structural formula:

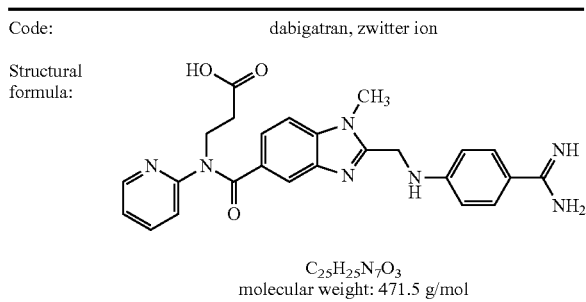

$C_{25}H_{25}N_7O_3$
molecular weight: 471.5 g/mol

1.1 Hapten Used for Synthesis of Immunogen and Tracer

Code: Hapten1

Structural formula of ligand:

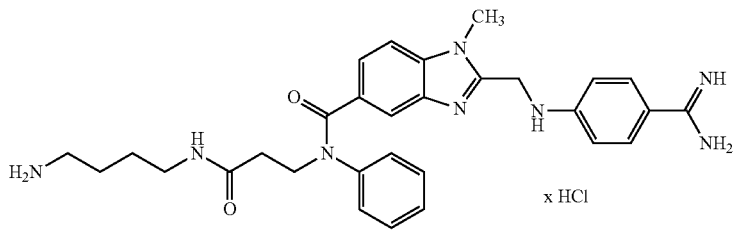 [SMILES: Cn1c(CNc2ccc(C(=N)N)cc2)nc2cc(C(=O)N(CCC(=O)NCCCCN)c3ccccc3)ccc21 ; "x HCl"]

$C_{30}H_{36}N_8O_2$ * HCl
molecular weight: 577.13 g/mol

Code: Hapten2

Structural formula of ligand:

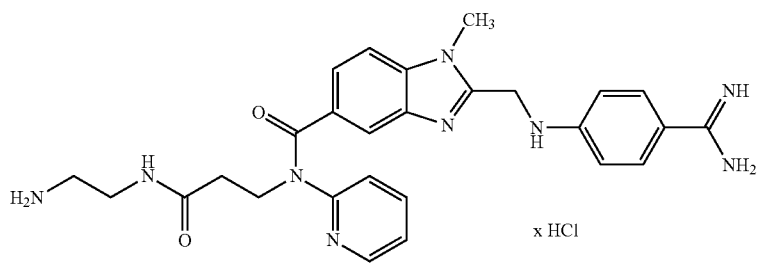 [SMILES: Cn1c(CNc2ccc(C(=N)N)cc2)nc2cc(C(=O)N(CCC(=O)NCCN)c3ccccn3)ccc21 ; "x HCl"]

$C_{27}H_{31}N_9O_2$ * HCl
molecular weight: 550.07 g/mol

1.2 Synthesis of Haptens

The haptens Hapten1 and Hapten2 were synthesized as follows:

Hapten1 2-[(4-Carbamimidoyl-phenylamino)-methyl]-1-methyl-1H-benzoimidazole-5-carboxylic acid [2-(4-amino-butylcarbamoyl)-ethyl]-phenyl-amide

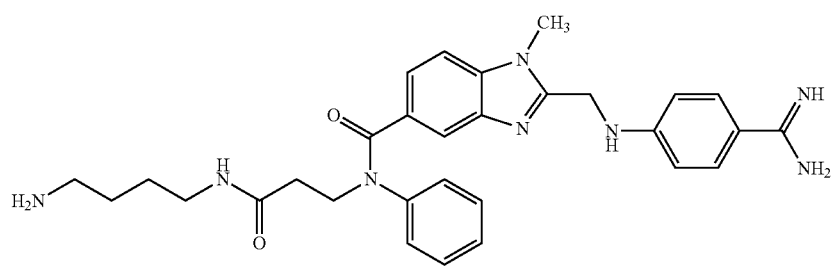 [SMILES: Cn1c(CNc2ccc(C(=N)N)cc2)nc2cc(C(=O)N(CCC(=O)NCCCCN)c3ccccc3)ccc21]

1a 3-[(4-Methylamino-3-nitro-benzoyl)-phenyl-amino]-propionic acid methyl ester

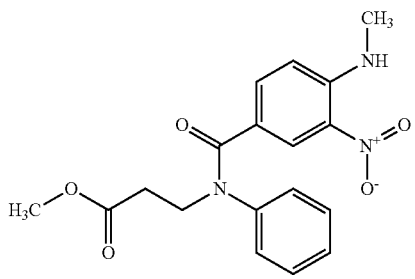 [SMILES: CNc1ccc(C(=O)N(CCC(=O)OC)c2ccccc2)cc1[N+](=O)[O-]]

To a solution of 4-methylamino-3-nitro-benzoic acid chloride (23.3 mmol) and 3-phenyl-amino-propionic acid methyl ester (23.3 mmol) in 80 mL dry tetrahydrofuran (THF) triethylamine (50.2 mmol) was added dropwise under stirring at room temperature. After three hours the reaction mixture was evaporated to dryness, the remaining solid triturated with water and the solid product isolated through filtration.

Yield: 99%
$C_{18}H_{19}N_3O_5$ (357.36)
TLC (silica gel; Dichloromethane/ethanol 19:1): $R_f$=0.48

1b 3-[(3-Amino-4-methylamino-benzoyl)-phenyl-amino]-propionic acid methyl ester

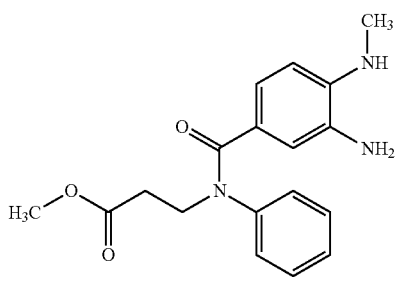 [SMILES: CNc1ccc(C(=O)N(CCC(=O)OC)c2ccccc2)cc1N]

The nitro group of product 1a was reduced by hydrogenation at room temperature in ethanol with Pd (10% on charcoal) as catalyst.

Yield: 99%
$C_{18}H_{21}N_3O_3$ (327.38)
TLC (silica gel; Dichloromethane/ethanol 9:1): $R_f$=0.23
Mass spectrum (ESI): [M+H]$^+$=328

1c 3-({3-[2-(4-Cyano-phenylamino)-acetylamino]-4-methylamino-benzoyl}-phenyl-amino)-propionic acid methyl ester

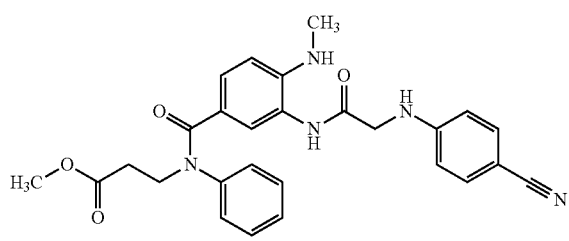 [SMILES: CNc1ccc(C(=O)N(CCC(=O)OC)c2ccccc2)cc1NC(=O)CNc1ccc(C#N)cc1]

The product of 1b (23.2 mmol) and N-(4-cyano-phenyl)-glycine (23.2 mmol) were coupled with CDI (23.2 mmol) in dry THF at room temperature. After completion of the reaction the mixture was evaporated to dryness and the crude product was used without further purification.

Yield: 97%
$C_{27}H_{27}N_5O_4$ (485.54)
Mass spectrum (ESI): [M+H]$^+$=486

1d 3-({2-[(4-Cyano-phenylamino)-methyl]-1-methyl-1H-benzoimidazole-5-carbonyl}-phenyl-amino)-propionic acid methyl ester

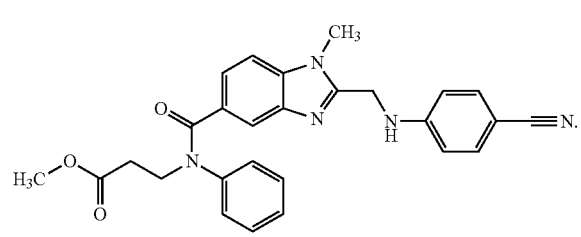 [SMILES: COC(=O)CCN(C(=O)c1ccc2c(c1)nc(CNc1ccc(C#N)cc1)n2C)c1ccccc1]

A solution of the product of 1c (22.6 mmol) in 100 mL concentrated acetic acid was heated to reflux for one hour. The solution was then evaporated to dryness, the remaining solid triturated with water and under stirring the pH was adjusted to about 8-9. The crude product was isolated through extraction with ethyl acetate and purified by chromatography on silica gel (eluent: dichloromethane/ethanol 1:1).

Yield: 58%
$C_{27}H_{25}N_5O_3$ (467.52)
TLC (silica gel; Dichloromethane/ethanol 9:1): $R_f$=0.71
Mass spectrum (ESI): [M+H]$^+$=468

1e 3-({2-[(4-Cyano-phenylamino)-methyl]-1-methyl-1H-benzoimidazole-5-carbonyl}-phenyl-amino)-propionic acid

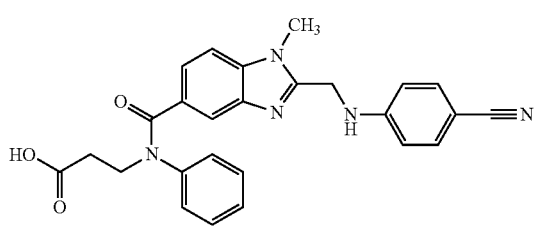 [SMILES: Cn1c(CNc2ccc(C#N)cc2)nc2cc(C(=O)N(CCC(=O)O)c3ccccc3)ccc21]

To a solution of the product of 1d (13.0 mmol) in 100 mL methanol sodium hydroxide (20.0 mmol) was added. The mixture was stirred for 2.5 hours at 40° C. and then evaporated to dryness. The remaining solid was stirred with 100 mL water and the pH was adjusted to about 6 with concentrated acetic acid. The precipitated product was isolated by filtration, washed with water and dried at 60° C.

Yield: 88%
$C_{26}H_{23}N_5O_3$ (453.49)
TLC (silica gel; Dichloromethane/ethanol 9:1): $R_f$=0.33
Mass spectrum (ESI): [M+H]$^+$=454

1f {4-[3-({2-[(4-Cyano-phenylamino)-methyl]-1-methyl-1H-benzoimidazole-5-carbonyl}-phenyl-amino)-propionylamino]-butyl}-carbamic acid tert-butyl ester

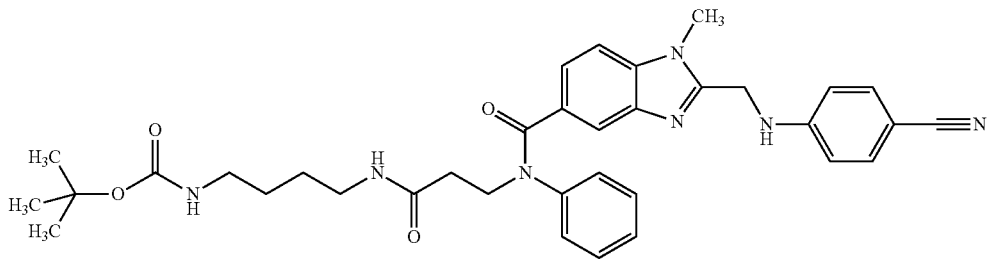 [SMILES: Cn1c(CNc2ccc(C#N)cc2)nc2cc(C(=O)N(CCC(=O)NCCCCNC(=O)OC(C)(C)C)c3ccccc3)ccc21]

A solution of the product of 1e (5.23 mmol), 2-(1H-benzotriazole-1-yl)-1,1,3,3-tetramethyluronium tetrafluoroborate (TBTU, 5.23 mmol) and N-methyl-morpholin (5.23 mmol) in 20 mL DMF was stirred at room temperature for 30 minutes. Then (4-amino-butyl)-carbamic acid tert-butyl ester (5.23 mmol) was added and the mixture stirred at room temperature for another 24 hours. The mixture was then diluted with water (100 mL) and the product was isolated through extraction with ethyl acetate.
Yield: 92%
$C_{35}H_{41}N_7O_4$ (623.75)
TLC (silica gel; Dichloromethane/ethanol 9:1): $R_f$=0.51

1g 2-[(4-Carbamimidoyl-phenylamino)-methyl]-1-methyl-1H-benzoimidazole-5-carboxylic acid[2-(4-amino-butylcarbamoyl)-ethyl]-phenyl-amide

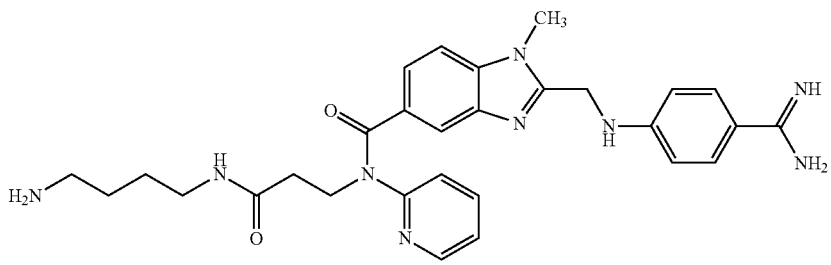

The product of 1f (4.81 mmol) was dissolved in a saturated solution of HCl in ethanol (250 mL), the mixture stirred at room temperature over night and then evaporated to dryness at 30° C. The remaining raw material was dissolved in 200 mL dry ethanol, then ammonium carbonate (48.1 mmol) was added and the mixture stirred at room temperature over night. After evaporation of the solvent the remaining raw material was triturated with ca. 5 mL ethanol, the undissolved material separated by filtration and the solvent evaporated at 30° C. The product was then dissolved in 30 mL water, the solution stirred with ca. 2 g charcoal, filtered and evaporated to dryness.
Yield: 90%
$C_{30}H_{36}N_8O_2$ (540.67)
TLC (reversed phase RP-8; methanol/5% aqueous NaCl solution 9:1): $R_f$=0.79
Mass spectrum (ESI): $[M+H]^+$=541
$[M+Cl]^-$=575/7

Hapten2 2-[(4-Carbamimidoyl-phenylamino)-methyl]-1-methyl-1H-benzoimidazole-5-carboxylic acid [2-(2-amino-ethylcarbamoyl)-ethyl]-pyridin-2-yl-amide 2a 3-({2-[(4-Cyano-phenylamino)-methyl]-1-methyl-1H-benzoimidazole-5-carbonyl}-pyridin-2-yl-amino)-propionic acid

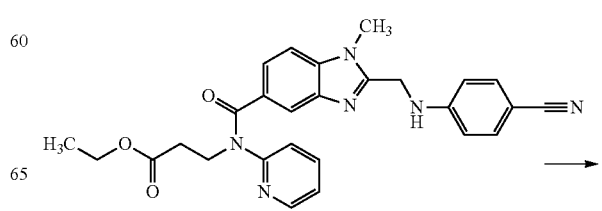

-continued

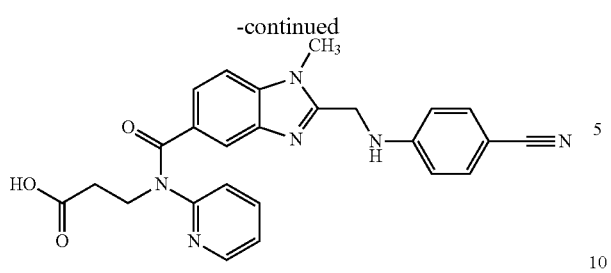

To a solution of sodium hydroxide (50.0 mmol) in 500 mL ethanol and 50 mL water was added 3-({2-[(4-Cyano-phenylamino)-methyl]-1-methyl-1H-benzoimidazole-5-carbonyl}-pyridin-2-yl-amino)-propionic acid ethyl ester (41.4 mmol). The mixture was stirred at room temperature for three hours, then ca. 350 mL ethanol were distilled off, ca. 100 mL water was added and the pH was adjusted to 6. Then diethyl-ether (50 mL) was added and the mixture stirred over night. The product was isolated by filtration and used without further purification.

Yield: 78%
$C_{25}H_{22}N_6O_3$ (454.48)

2b {2-[3-({2-[(4-Cyano-phenylamino)-methyl]-1-methyl-1H-benzoimidazole-5-carbonyl}-pyridin-2-yl-amino)-propionylamino]-ethyl}-carbamic acid tert-butyl ester

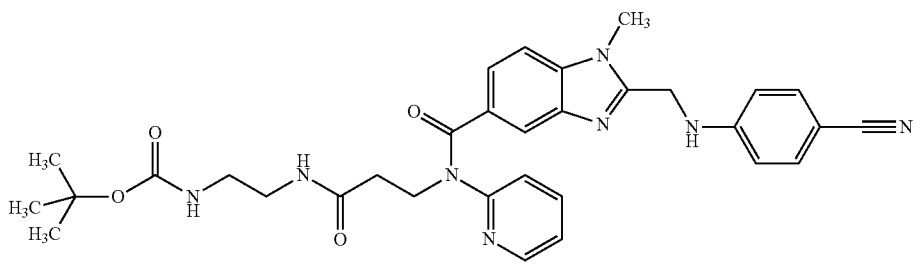 [SMILES: Cn1c(CNc2ccc(C#N)cc2)nc2cc(C(=O)N(CCC(=O)NCCNC(=O)OC(C)(C)C)c3ccccn3)ccc21]

A solution of the product of 2a (2.20 mmol), 2-(1H-benzotriazole-1-yl)-1,1,3,3-tetramethyluronium tetrafluoroborate (TBTU, 2.20 mmol) and N-methyl-morpholin (2.20 mmol) in dry tetrahydrofuran (100 mL) was stirred at room temperature for 15 minutes. Then (2-amino-ethyl)-carbamic acid tert-butyl ester (2.20 mmol) was added and the mixture stirred at room temperature for another 24 hours. The mixture was then diluted with 40 mL water, the product was isolated through extraction with ethyl acetate and purified by chromatography (silica gel; dichloromethane/methanol 15:1).

Yield: 61%
$C_{32}H_{36}N_8O_4$ (596.68)

Mass spectrum (ESI): $[M+H]^+=597$
$[M+H]^-=595$ 2c 2-[(4-Carbamimidoyl-phenylamino)-methyl]-1-methyl-1H-benzoimidazole-5-carboxylic acid [2-(2-amino-ethylcarbamoyl)-ethyl]-pyridin-2-yl-amide

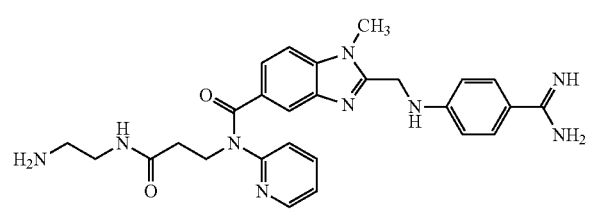 [SMILES: Cn1c(CNc2ccc(C(=N)N)cc2)nc2cc(C(=O)N(CCC(=O)NCCN)c3ccccn3)ccc21]

The product of 2b (1.34 mmol) was added to a saturated HCl solution in dry ethanol (30 mL). The solution was stirred at room temperature for 5 hours, then evaporated to dryness at 30° C. Ethanol (30 mL) and ammonium carbonate (13.0 mmol) were added and the mixture stirred at room temperature over night. The solvent was then evaporated, the residual material was triturated 5 times with ca. 4 mL of a mixture of dichloromethane/methanol (30:1), filtered and evaporated in order to separate the product from inorganic salts.

Yield: 27%
$C_{27}H_{31}N_9O_2$ (513.61)
Mass spectrum (ESI): $[M+Cl]^-=548/50$
$[M+HCl+Cl]^-=584/6$
$[M+H]^+=514$ 2. Chemicals 2.1 Chemicals for Reagent Synthesis

| name | specification | supplier | catalogue no. |
|---|---|---|---|
| 1,4-Benzoquinone | | Fluka | 12309 |
| Bovines Serum Albumin (BSA) | | Serva | 11920 |
| 1,1'-Carbonyl-di-(1,2,4-triazol) | | Fluka | 21861 |
| Citric acid | analytical grade | Riedel-De Haën | 33114 |

| name | specification | supplier | catalogue no. |
|---|---|---|---|
| N,N-dimethylformamide (DMF) | for synthesis | Merck | 822275 |
| Ethanol | analytical grade | Baker | 8006 |
| Freund's adjuvant (CFA) | Complete | Sigma | F-5881 |
| Freund's adjuvant (IFA) | Incomplete | Sigma | F-5506 |
| Glycerine | Pure | Merck | 104093 |
| horseradish peroxidase HRP | 25000 U/100 mg | Boehringer Mannheim | 108090 |
| $H_2SO_4$ | analytical grade | Riedel-De Haën | 30743 |
| $KH_2PO_4$ | analytical grade | Merck | 4873 |
| $NaHCO_3$ | analytical grade | Merck | 106329 |
| $Na_2CO_3$ | analytical grade | Merck | 106392 |
| $(NH_4)_2SO_4$ | analytical grade | Merck | 101217 |
| o-phenylene diamine | 30 mg tablet | Sigma | P8412 |
| Sodium perborate | Pure | Riedel-De Haën | 11621 |
| Thymol | Pure | Merck | 8167 |

2.2 Chemicals for ELISA

| Name | Specification | supplier | catalogue no. |
|---|---|---|---|
| Citric acid | analytical grade | Riedel-De Haën | 33114 |
| $H_2SO_4$ | analytical grade | Riedel-De Haën | 30743 |
| $KH_2PO_4$ | analytical grade | Merck | 4873 |
| $Na_2HPO_4 \cdot 2\, H_2O$ | analytical grade | Merck | 6580 |
| NaCl | analytical grade | Merck | 6404 |
| NaOH | analytical grade | Merck | 6498 |
| o-phenylene diamine | 30 mg tablet | Sigma | P8412 |
| Sodium perborate | Pure | Riedel-De Haën | 11621 |
| Tween 20 | Pure | Serva | 37470 |

2.3 Buffers for ELISA

| Name | Ingredients | use |
|---|---|---|
| buffer 1 | 0.05M $Na_2HPO_4$/$KH_2PO_4$ 0.15M NaCl, pH = 7.4 | coating |
| stability: | 4 weeks at approximately +4° C. | |
| buffer 2 | as buffer 1, with 5 g/l BSA | assay buffer |
| stability: | 10 days at approximately +4° C. | |
| buffer 3 | as buffer 1, with 5 g/l BSA and 0.1 g/L thimerosal | microplate blocking; storage |
| stability: | 4 weeks at approximately +4° C. | |
| buffer 4 | 0.1M citric acid, adjusted to pH 5.0 with NaOH, 6.5 mmol/L sodium perborate | substrate buffer for o-phenylene diamine |
| stability: | citric acid: 6 months at approximately +4° C. with perborate: 10 days at approximately +4° C. | |
| wash solution | water, 0.5 g/L Tween 20 | microplate washing |
| stability: | 10 days at ambient temperature | |
| stop reagent | 2.25M $H_2SO_4$ | arrests o-phenylene diamine colour development |
| stability: | 5 years at ambient temperature | |

Water from an Elgastat Maxima-HPLC ultra pure water processing system was used to prepare buffer solutions.

3. Synthesis of Immunogens

In order to stimulate the immune system of rabbits to produce polyclonal antibodies against dabigatran, three immunogens (lot. nos. GL256, GL258, and GL262,) were synthesized by coupling the haptens HAPTEN1 and HAPTEN2 to the carrier protein bovine serum albumin (BSA) using 1,4-benzoquinone or 1,1'-carbonyl-di-(1,2,4-triazol) as coupling reagent.

For the synthesis of GL256, 1,4-benzoquinone was used as a homobifunctional compound with two reactive sites. First it reacts at an acidic pH with amino groups at only one of the two sites and at an alkaline pH at the other site with minimal polymerization. GL258 and GL262 were synthesized using 1,1'-carbonyl-di-(1,2,4-triazol) as coupling reagent with different input ratios of the hapten to the carrier protein.

3.1 Synthesis of GL256

To the solution of 0.75 μMol BSA in 8.5 mL 0.1 M $KH_2PO_4$-buffer (pH=4.5), 0.416 mMol 1,4-benzoquinone (in 1.5 mL ethanol) was added and incubated for 1.5 h in the dark at room temperature. Afterwards the solution passed a sephadex G25 column equilibrated in 0.15 M NaCl to eliminate the excess of 1,4-benzoquinone (final volume 12.5 mL).

2.5 mL (0.15 μMol) of the purified BSA-solution were added slowly under stirring to a solution of the 525 μMol hapten HAPTEN1 dissolved in 2 mL 0.1 M $NaHCO_3$/$Na_2CO_3$-buffer (pH=8.5). During addition of the BSA solution the pH was adjusted to approximately 8.0. The molar input ratio of the hapten and the carrier protein was 3500:1.

After incubation at room temperature over night the immunogen was dialysed 6 times against 1 litre of aqua. dest. Thin-layer chromatography showed that no spots of unbound hapten remained in the hapten-carrier conjugates.

The immunogen was stored frozen in aliquots at −20° C. The degree of substitution of BSA with hapten in the supernatant of the immunogen was about 1:18 as determined by UV absorption spectrometry at 302 nm. The content of immunogen in the final solution was 0.75 mg GL256/mL 3.2 Synthesis of GL258

A solution of 158 μMol HAPTEN2 in 6.3 mL N,N-dimethylformamide (DMF) was prepared at room temperature. 158 μMol 1,1'-carbonyl-di-(1,2,4-triazol) was added and incubated first for 4 hours at 10° C. and afterwards for 30 min at room temperature. The chemical reaction was checked with thin-layer chromatography and was about 20-25%.

Then 0.75 μMol BSA were dissolved in 2 mL 0.13 M $NaHCO_3$ and 1 mL N,N-dimethylformamide (DMF) was added dropwise under stirring. The pH was adjusted to approximately 8.3. Afterwards the hapten solution (6.3 mL) and 4 mL 0.13 M $NaHCO_3$ were added dropwise to the BSA solution under stirring and the pH was adjusted to 8.4. The molar input ratio of the hapten and the carrier protein was 210:1 for the immunogen GL258.

After incubation at room temperature over night under stirring conditions, the immunogen was dialysed 6 times against 1 litre of aqua. dest. Thin-layer chromatography showed that no spots of unbound hapten remained in the hapten-carrier conjugates.

The immunogen was stored frozen in aliquots at −20° C. The degree of substitution of BSA with hapten in the supernatant of the immunogen was about 1:5 as determined by UV absorption spectrometry at 302 nm. The content of immunogen in the final solution was 0.28 mg GL258/mL.

3.3 Synthesis of GL262

A solution of 225 μMol HAPTEN2 in 8.75 mL N,N-dimethylformamide (DMF) was prepared at room temperature. 225 μMol 1,1'-carbonyl-di-(1,2,4-triazol) was added and incubated for 4 hours at 10° C. The chemical reaction was checked with thin-layer chromatography and was about 20-25%.

Then 0.49 μMol BSA were dissolved in 2 mL 0.13 M NaHCO$_3$ and 1 mL N,N-dimethylformamide (DMF) was added dropwise under stirring. The pH was adjusted to approximately 8.2. Afterwards the hapten solution (8.75 mL) and 6 mL 0.13 M NaHCO$_3$ were added dropwise to the BSA solution under stirring and the pH was adjusted to 8.3. The molar input ratio of the hapten and the carrier protein was 460:1 for the immunogen GL262.

After incubation at room temperature over night under stirring conditions, the immunogen was dialysed 6 times against 1 litre of aqua. dest. Thin-layer chromatography showed that no spots of unbound hapten remained in the hapten-carrier conjugates.

The immunogen was stored frozen in aliquots at −20° C. The degree of substitution of BSA with hapten in the supernatant of the immunogen was about 1:32 as determined by UV absorption spectrometry at 302 nm. The content of immunogen in the final solution was 0.71 mg GL262/mL 4. Synthesis of Conjugate 4.1 Synthesis of GL261

A solution of 37.4 μMol HAPTEN2 in 1.5 mL N,N-dimethylformamide (DMF) was prepared at room temperature. 37.5 μMol 1,1'-carbonyl-di-(1,2,4-triazol) was added and incubated first for 4 hours at 10° C. and afterwards for 30 min at room temperature. The chemical reaction was checked with thin-layer chromatography and was about 20-25%.

Then 1.125 μMol enzyme horseradish peroxidase (HRP) were dissolved in 0.4 mL 0.13 M NaHCO$_3$ and 0.267 mL N,N-dimethylformamide (DMF) was added dropwise under stirring. The pH was adjusted to approximately 8.2. Afterwards 0.9 mL of the hapten solution (22.5 μMol) and 0.57 mL 0.13 M NaHCO$_3$ were added dropwise to the HRP solution under stirring and the pH was adjusted to 8.4. The molar input ratio of the hapten and the HRP was 20:1 for the HRP conjugate GL261.

After incubation at room temperature over night under stirring conditions, the HRP conjugate was separated from organic solvents and the excess of hapten by gel chromatography. The solution passed a sephadex G25 column equilibrated with 0.1 M phosphate buffer pH 7.0.

The final concentration of hapten-HRP conjugate (tracer, 5.64 mg/mL) was spiked with BSA yielding a concentration of about 10 mg/mL, an equal volume of glycerine to prevent freezing and a thymol crystal to prevent bacterial growth. The tracer solution was labelled as lot no. GL261 and stored in aliquots at −20° C.

The degree of substitution of HRP with hapten was 1:0.2 as determined by UV spectroscopy at 302 nm.

The specific activity of the tracer was measured in BSA-blocked microtiter plates using o-phenylene-diamine (OPD) as substrate and native HRP as reference material. The mixture of diluted HRP standards or the hapten-HRP conjugate and substrate solution were incubated for 30 min in the dark, stopped with sulphuric acid and absorption measured at 490 nm. The remaining activity was 94% of the native HRP and the specific activity of the conjugate formulation in glycerine was 611 U/mL.

Summary of Tracer Specifications:

| type: | HAPTEN2 - horseradish peroxidase (lot no. GL 261) |
|---|---|
| protein content: | 5.64 mg/mL |
| specific activity: | 108 U/mg 611 U/ml (substrate Guajacol and H$_2$O$_2$, 25° C.) |
| storage: | at approximately −20° C. |
| working dilution: | 1:40000 |

5. Immunization and Production of Antibodies 5.1 Immunization of Rabbits

Twelve female chinchilla rabbits, 3 months old, were immunized with an emulsion of 100 μg immunogen GL256, GL258 and GL262 in 0.5 mL 0.9% NaCl solution and 0.5 mL of complete Freund's adjuvant (CFA). Several booster immunizations followed in the next month. For the third immunization 0.5 mL of incomplete Freund's adjuvant (IFA) was used. Each immunization was performed at four subcutaneous and four intramuscular sites.

| Group A - immunogen GL256 |
|---|
| Rabbit 1 #50 |
| Rabbit 2 #51 |
| Rabbit 3 #52 |
| Rabbit 4 #53 |
| Group B - immunogen GL258 |
| Rabbit 5 #54 |
| Rabbit 6 #55 |
| Rabbit 7 #56 |
| Rabbit 8 #57 |
| Group C - immunogen GL262 |
| Rabbit 9 #46 |
| Rabbit 10 #47 |
| Rabbit 11 #48 |
| Rabbit 12 #49 |

Immunization Scheme

| Day 1 | First immunization with 100 μg immunogen/mL per animal in CFA |
|---|---|
| Day 29 | Second immunization with 100 μg immunogen/mL per animal in CFA |
| Day 57 | Third immunization with 100 μg immunogen/ml per animal in IFA the rabbit's state of the healthy might change for the worse by the use of immunogens GL256 and GL258 rabbit 7 #56 was not treated |
| Day 67 | First bleeding (2 mL per animal) |
| Day 81 | Fourth immunization with 100 μg immunogen/mL per animal in CFA |
| Day 91 | Second bleeding (25 mL per animal) |
| Day 112 | Fifth immunization with 100 μg immunogen/mL per animal in CFA |
| Day 122 | Assignment of the animal numbers was mislaid Third final bleeding (Exsanguination)* |

*Rabbit no. 1-12 were exsanguinated completely 10 days after the fifth immunization. Exsanguination was performed via a carotid artery under anesthesia with xylazin (Rompun ®, Bayer, Leverkusen, Germany) and ketamine hydrochloride (Ketavet ®, Parke-Davis, Freiburg, Germany).

5.2 Analysis of Rabbit Sera

Serum was prepared by centrifugation of the coagulated rabbit blood. A protein fraction was obtained by ammonium sulphate precipitation and desalting through a Sephadex G25 column.

The individual protein fractions from the rabbit sera were screened for anti-dabigatran titer by a standard ELISA procedure.

Screening-ELISA:

| Step | Procedure |
|---|---|
| A | protein fractions from each bleeding were adsorbed overnight at ambient temperature onto microtiter plates (100 μL/well; 1, 2 or 4 μg/mL) in buffer 1. wash microplates 4 times, 450 μL each block with 250 μL buffer 3 for at least 1 hour |
| B | wash microplates 4 times, 450 μL each |
| C | add to each well of microtiter plate in triplicate: +50 μL buffer 2 +50 μL calibration standards in buffer 2 +25 μL dabigatran-horseradish peroxidase (HRP) conjugate GL 261 (tracer) (1/40000) |
| D | seal microplates with adhesive foil, complete sample distribution for all microplates incubate for 4 h on a shaker at ambient temperature |
| E | wash microplates 4 times, 450 μL each |
| F | add to each well of microtiter plate 100 μL o-phenylene diamine HCl, 2.7 mg/mL (one 30 mg tablet in 11 ml buffer 4) incubate for 30 min in the dark at ambient temperature |
| G | add to each well of microtiter plate 100 μL $H_2SO_4$ (2.25M) shake for 5 minutes |
| H | read absorbance; test-wavelength: 490 nm, reference-wavelength: 650 nm |

5.3 Detection of Anti-Dabigatran Antibodies in Rabbit Sera

Last three columns: values are for dabigatran bleeding 2

| rabbit | immunogene | coating conc [μg/ml] | conc. [Mol] | [Ext] | [%] |
|---|---|---|---|---|---|
| 1 | #50 | GL256 | 2 | 0 | 1.812 | 100% |
| | | | | 2.E-12 | 1.574 | 87% |
| | | | | 2.E-11 | 0.461 | 25% |
| | | | | 2.E-10 | 0.059 | 3% |
| 2 | #51 | GL256 | 1 | 0 | 2.193 | 100% |
| | | | | 2.E-12 | 2.086 | 95% |
| | | | | 2.E-11 | 1.515 | 69% |
| | | | | 2.E-10 | 0.207 | 9% |
| 3 | #52 | GL256 | 2 | 0 | 1.513 | 100% |
| | | | | 2.E-12 | 1.419 | 94% |
| | | | | 2.E-11 | 0.728 | 48% |
| | | | | 2.E-10 | 0.107 | 7% |
| 4 | #53 | GL256 | 2 | 0 | 1.474 | 100% |
| | | | | 2.E-12 | 1.388 | 94% |
| | | | | 2.E-11 | 0.848 | 58% |
| | | | | 2.E-10 | 0.142 | 10% |
| 5 | #54 | GL258 | 1 | 0 | 2.114 | 100% |
| | | | | 2.E-12 | 1.892 | 89% |
| | | | | 2.E-11 | 0.646 | 31% |
| | | | | 2.E-10 | 0.159 | 8% |
| 6 | #55 | GL258 | 1 | 0 | 1.295 | 100% |
| | | | | 2.E-12 | 0.937 | 72% |
| | | | | 2.E-11 | 0.265 | 20% |
| | | | | 2.E-10 | 0.140 | 11% |
| 7 | #56 | GL258 | 2 | 0 | 1.611 | 100% |
| | | | | 2.E-12 | 1.372 | 85% |
| | | | | 2.E-11 | 0.424 | 26% |
| | | | | 2.E-10 | 0.145 | 9% |
| 8 | #46 | GL258 | 1 | 0 | 1.640 | 100% |
| | | | | 2.E-12 | 1.290 | 79% |
| | | | | 2.E-11 | 0.425 | 26% |
| | | | | 2.E-10 | 0.196 | 12% |
| 9 | #47 | GL262 | 2 | 0 | 1.854 | 100% |
| | | | | 2.E-12 | 1.534 | 83% |
| | | | | 2.E-11 | 0.530 | 29% |
| | | | | 2.E-10 | 0.254 | 14% |
| 10 | #48 | GL262 | 2 | 0 | 1.458 | 100% |
| | | | | 2.E-12 | 1.142 | 78% |
| | | | | 2.E-11 | 0.300 | 21% |
| | | | | 2.E-10 | 0.131 | 9% |
| 11 | #49 | GL262 | 4 | 0 | 1.646 | 100% |
| | | | | 2.E-12 | 1.393 | 85% |
| | | | | 2.E-11 | 0.460 | 28% |
| | | | | 2.E-10 | 0.257 | 16% |
| 12 | #50 | GL262 | 2 | 0 | 1.605 | 100% |
| | | | | 2.E-12 | 1.400 | 87% |
| | | | | 2.E-11 | 0.389 | 24% |
| | | | | 2.E-10 | 0.109 | 7% |

Final Bleeding

| rabbit | immunogene | coating conc [μg/ml] | conc. [Mol] | [Ext] | [%] |
|---|---|---|---|---|---|
| 1 | ? | | 1 | 0 | 1.589 | 100% |
| | | | | 2.E-12 | 1.442 | 91% |
| | | | | 2.E-11 | 0.491 | 31% |
| | | | | 2.E-10 | 0.130 | 8% |
| 2 | ? | | 1 | 0 | 1.375 | 100% |
| | | | | 2.E-12 | 1.041 | 76% |
| | | | | 2.E-11 | 0.293 | 21% |
| | | | | 2.E-10 | 0.101 | 7% |
| 3 | ? | | 1 | 0 | 1.400 | 100% |
| | | | | 2.E-12 | 1.081 | 77% |
| | | | | 2.E-11 | 0.288 | 21% |
| | | | | 2.E-10 | 0.097 | 7% |
| 4 | ? | | 1 | 0 | 1.183 | 100% |
| | | | | 2.E-12 | 0.882 | 75% |
| | | | | 2.E-11 | 0.396 | 33% |
| | | | | 2.E-10 | 0.183 | 15% |
| 5 | ? | | 1 | 0 | 1.335 | 100% |
| | | | | 2.E-12 | 1.066 | 80% |
| | | | | 2.E-11 | 0.183 | 14% |
| | | | | 2.E-10 | 0.057 | 4% |
| 6 | ? | | 1 | 0 | 1.214 | 100% |
| | | | | 2.E-12 | 0.976 | 80% |
| | | | | 2.E-11 | 0.250 | 21% |
| | | | | 2.E-10 | 0.123 | 10% |
| 7 | ? | | 2 | 0 | 1.822 | 100% |
| | | | | 2.E-12 | 1.702 | 93% |
| | | | | 2.E-11 | 0.661 | 36% |
| | | | | 2.E-10 | 0.189 | 10% |

-continued

| rabbit | immunogene | coating conc [µg/ml] | conc. [Mol] | [Ext] | [%] |
|---|---|---|---|---|---|
| 8 | ? | 2 | 0 | 1.234 | 100% |
|  |  |  | 2.E-12 | 1.085 | 88% |
|  |  |  | 2.E-11 | 0.671 | 54% |
|  |  |  | 2.E-10 | 0.147 | 12% |
| 9 | ? | 1 | 0 | 1.911 | 100% |
|  |  |  | 2.E-12 | 1.862 | 97% |
|  |  |  | 2.E-11 | 0.980 | 51% |
|  |  |  | 2.E-10 | 0.292 | 15% |
| 10 | ? | 1 | 0 | 1.933 | 100% |
|  |  |  | 2.E-12 | 1.891 | 98% |
|  |  |  | 2.E-11 | 1.055 | 55% |
|  |  |  | 2.E-10 | 0.076 | 4% |
| 11 | ? | 1 | 0 | 1.874 | 100% |
|  |  |  | 2.E-12 | 1.817 | 97% |
|  |  |  | 2.E-11 | 1.539 | 82% |
|  |  |  | 2.E-10 | 0.181 | 10% |
| 12 | ? | 2 | 0 | 1.599 | 100% |
|  |  |  | 2.E-12 | 1.425 | 89% |
|  |  |  | 2.E-11 | 0.475 | 30% |
|  |  |  | 2.E-10 | 0.050 | 3% |

After screening of the protein fractions of all rabbits from bleeding 2, it was obvious that rabbit no. 5 (#54) had the highest titre of anti-dabigatran antibodies with the preferred hapten HAPTEN2. Furthermore, it was possible to displace the tracer from the antibody binding sites with only low concentrations of analyte (dabigatran).

For the screening of the final bleeding 3, the displacement of the tracer from the antibody binding site with low concentrations of analyte (dabigatran) was used as main decision criteria, because of the missing information about the immunogen used. Therefore rabbits no. 2, 3 and 5 were used for the further purification.

5.4 Purification of Polyclonal Antibodies

The anti-serum of rabbit no. 5 (#54) bleeding no. 2 and rabbits no. 2, 3 and 5 bleeding no. 3 (final bleeding) was precipitated with ammonium sulphate. The precipitate was centrifuged for 30 min at 10° C. at 4500 U/min, separated from the solution and re-dissolved in Tris buffer. This procedure was repeated. Further purification was performed by affinity chromatography on protein A sepharose FF. The column buffer was 0.01 M Tris pH=7.5 and 0.1 M glycine pH=3.0 was used for elution. Fractions containing the rabbit IgG were combined. Protein concentration was determined by UV spectroscopy at 280 nm.

Summary of Antibody Specifications:

| | |
|---|---|
| immunogen: | HAPTEN2 - BSA (lot no. GL258) |
| rabbit: | no. 5 (#54) serum (bleeding no. 2) |
| protein content: | 1.85 mg/mL |
| storage: | at approximately −20° C. |
| immunogen: | HAPTEN1 - BSA (GL256) or |
|  | HAPTEN2 - BSA (lot no. GL258) or |
|  | HAPTEN2 - BSA (lot no. GL262) |
| rabbit: | no. 2 serum collected (final bleeding) |
| protein content: | 3.9 mg/mL |
| storage: | at approximately −20° C. |
| immunogen: | HAPTEN1 - BSA (GL256) or |
|  | HAPTEN2 - BSA (lot no. GL258) or |
|  | HAPTEN2 - BSA (lot no. GL262) |
| rabbit: | no. 3 serum (final bleeding) |
| protein content: | 9.96 mg/mL |
| storage: | at approximately −20° C. |
| immunogen: | HAPTEN1 - BSA (GL256) or |
|  | HAPTEN2 - BSA (lot no. GL258) or |
|  | HAPTEN2 - BSA (lot no. GL262) |
| rabbit: | no. 5 serum (final bleeding) |
| protein content: | 5.72 mg/mL |
| storage: | at approximately −20° C. |

II. Neutralization of Dabigatran

Two series of experiments were performed to show the effect of the antibodies against dabigatran anticoagulant activity in vitro. The four polyclonal antibodies were received in the laboratory and further tested in human plasma. This was tested in the functional assay, the thrombin clotting time.

Assay Description:

Briefly human plasma is obtained by taking whole blood into 3.13% sodium citrate. This is then centrifuged to obtain platelet free plasma and transferred to a separate tube and frozen until required on the day of the assay. Plasma is thawed at 37° C. on the day of the assay.

The thrombin clotting time is performed as follows. First thrombin is diluted to manufacturer's specification (3 IU/mL thrombin) in the buffer provided (Dade Behring Test kit) and prewarmed to 37° C. It is used within 2 hrs of being prepared. All assays were performed on a commercially available CL4 clotting machine (Behnk Electronics, Norderstadt, Germany). Fifty µL of plasma is pipetted into provided cuvettes with a magnetic stirrer and allowed to stir for 2 min in the well preheated to 37° C. in the CL4 machine. At this point 100 µL of the thrombin solution is added and the time required for the plasma sample to clot is recorded automatically by the CL4. Dabigatran is preincubated for 5 min in plasma in the provided cuvettes, before adding thrombin and starting the measurement. If antibody is also tested (up 50 µL of stock solution), there is a further 5 minute incubation at 37° C. before beginning clotting (i.e. 10 min total incubation with dabigatran, 5 min total incubation with antibody and then clotting is initiated with thrombin).

Initially a dabigatran standard curve was performed by adding increasing concentrations of dabigatran to human plasma and measuring the time to clotting after addition of thrombin (FIG. 1). There was a concentration-dependent increase in the thrombin clotting time with increasing concentrations of dabigatran.

Figure 2:
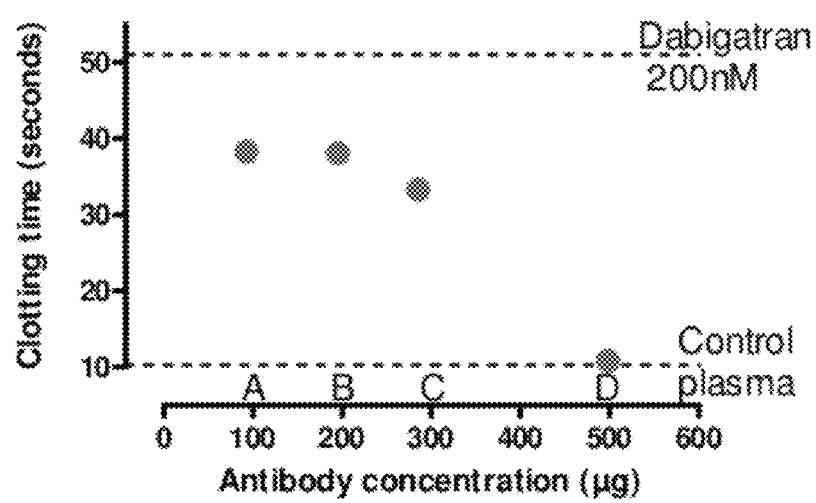
FIG. 2: Four different antibodies to dabigatran (A-D) all neutralized the prolonged clotting time of dabigatran in human plasma. Baseline clotting in human plasma was 10.9 seconds, when 200 nM dabigatran was preincubated with plasma, clotting was prolonged to 51 seconds. Each antibody was added to plasma preincubated with 200 nM of dabigatran and further incubated for 5 min. The thrombin clotting time was then initiated by addition of thrombin. Each antibody could reverse the clotting time of dabigatran to different degrees. The most concentrated solution resulted in the largest reversal of anticoagulant activity.
Figure 3:
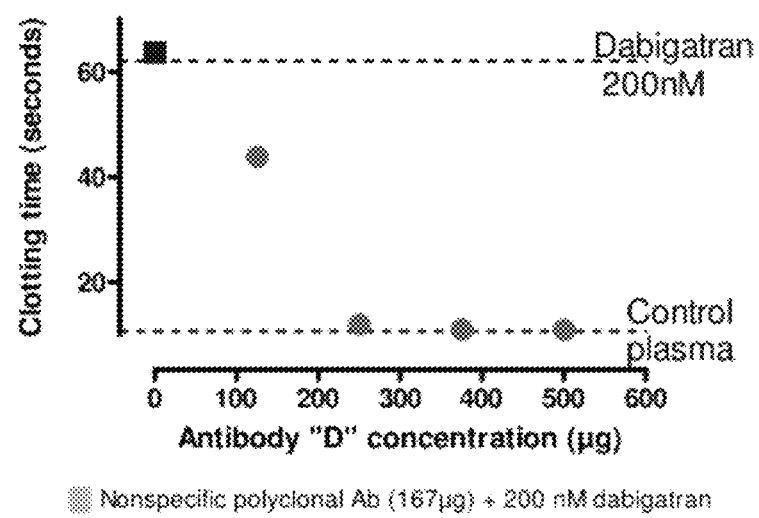
FIG. 3: The effect of increasing concentrations of polyclonal antibody (antibody D) added to human plasma that had been preincubated with 200 nM dabigatran was measured. Baseline clotting time was 11 seconds, addition of dabigatran prolonged clotting to 63.7 seconds. The effect of increasing dilutions of antibody on reversing the prolonged thrombin clotting time with dabigatran was then tested. The lowest concentration reduced the thrombin clotting time to 43.9 seconds. Higher concentrations completely reduced the thrombin clotting time to baseline levels and resulted in complete neutralization of the anticoagulant effect of dabigatran. Addition of a non specific rabbit polyclonal antibody (square) had no effect on reversing the anticoagulant effect of dabigatran.

For the first set of neutralization experiments, a clinically relevant concentration of 200 nM of dabigatran was added to all plasma samples for neutralization. All 4 antibody preparations were able to shorten the time to clotting in plasma containing dabigatran (FIG. 2). The extent of neutralization was related to the concentration of protein in each antibody preparation. The antibody solution with the highest concentration (D) was then serially diluted and tested for the ability to neutralize 200 nM dabigatran anticoagulant activity in a separate set of experiments. It can be seen in FIG. 3, there was a concentration dependent inhibition of dabigatran-induced anticoagulant activity with increasing concentrations of antibody. In addition when a non-specific rabbit polyclonal antibody (blue square) was added to plasma containing dabigatran, it had no ability to neutralise the anticoagulant activity. The concentration dependency and the lack of neutralization of a non specific antibody indicate the reversal of anticoagulation by the antibody is specific for dabigatran.

Figure 4:
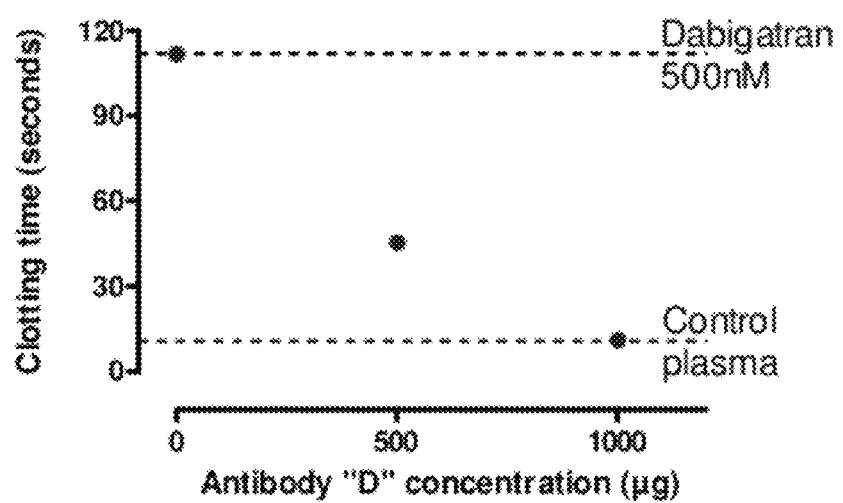
FIG. 4: The effect of increasing concentrations of polyclonal antibody (antibody D) added to human plasma that had been preincubated with 500 nM dabigatran was measured. Baseline clotting time was 10.9 seconds, addition of this higher concentration of dabigatran prolonged clotting to 111.7 seconds (~10-fold increase). The effect of a 1:2 dilution of antibody or stock solution reversed the prolonged thrombin clotting time with dabigatran in a concentration dependent manner. The highest concentration also completely reversed the thrombin clotting time to baseline levels and resulted in complete neutralization of the anticoagulant effect of even supratherapeutic concentrations of dabigatran.

However, these concentrations of dabigatran are clinically relevant, and bleeding or overdoses will probably occur with higher concentrations. Thus the ability of an antibody to inhibit the anticoagulant activity of the highest concentration of dabigatran (500 nM) in the standard curve in FIG. 1 was also tested. FIG. 4 illustrates that antibody D could also inhibit high concentrations of dabigatran.

III. Production and Characterization of Monoclonal Anti-Dabigatran Antibodies

1. Production of Monoclonal Anti-Dabigatran Antibodies and Fabs

Mice were immunized with Hapten1 (see Example 1.1) conjugated to carrier proteins such as hemocyanin and immunoglobulin and hybridomas were generated according to standard procedures. Monoclonal antibodies purified from the culture supernatants bound to dabigatran-protein conjugates and this binding could be competed with dabigatran in solution with half-maximal inhibition at concentrations in the range of 1 to 10 nM. Fabs were generated by papain cleavage of the monoclonal antibodies with subsequent elimination of the Fc domain via Protein A.

The variable regions from the heavy and light chains of the mouse antibodies were cloned and sequenced using standard methods. The sequences were confirmed by protein analysis by mass spectrometry and N-terminal sequencing of the antibodies. DNA constructs encoding chimeric antibodies comprising the specific mouse variable regions and human IgG constant regions were generated and protein was expressed in HEK293 cells and purified.

In order to reduce potential immunogenicity, sequences of mouse monoclonal antibody clones 35E6 and 27A9 were humanized by standard methods described above. Humanized Fabs were produced by transient transfection in mammalian cells (e.g. HEK293; CHO cells) and purified by affinity chromatography with benzamidine sepharose followed by size exclusion chromatography.

2. Characterization of Monoclonal Anti-Dabigatran Antibodies and Fabs

The sequences of the variable domains of 9 monoclonal antibody clones DBG22 (clone 22), 35E6, 45B9, 48E1, 49F8, 6A7F1, 2F1E5, 3B4E7, 1F6G8, 2D2E3, and 27A9 are depicted in Table 1. SEQ ID NO's 67, 68, 69, 92, 93, 94, 99, 100 and 101 represent optimized and/or humanized sequences. The Fab compound VH5C/VK18 comprises HCVH5C (SEQ ID NO: 99) as heavy chain, and LCVK18 (SEQ ID NO: 100) as light chain. The Fab compound VH5C/VK21 comprises HCVH5C (SEQ ID NO: 99) as heavy chain, and LCVK21 (SEQ ID NO: 101) as light chain. Thus, both VH5C/VK18 and VH5C/VK21 comprise a heavy chain variable domain with a CDR1 of SEQ ID NO: 67, a CDR2 of SEQ ID NO: 68, and a CDR3 of SEQ ID NO: 9, and a light chain variable domain with a CDR1 of SEQ ID NO: 64, a CDR2 of SEQ ID NO: 65, and a CDR3 of SEQ ID NO: 69. Both Fabs share a variable region of the heavy chain of SEQ ID NO: 92 (VH5C). VH5C/VK18 comprises a variable region of the light chain of SEQ ID NO: 93 (VK18), and VH5C/VK21 comprises a variable region of the light chain of SEQ ID NO: 94 (VK21).

In Table 1, the letters "CDR" denote a complementarity determining region, "VH" denotes the variable region of a heavy chain, "VK" denotes the variable region of a kappa light chain, "CL" denotes the constant region of a light chain, and "CH" denotes the constant region of a heavy chain, "LC" denotes the light chain of an antibody molecule, and "HC" denotes the heavy chain of an antibody molecule. For example, "VHCDR1 DBG22" denotes the first CDR (CDR1) of the variable domain of the heavy chain of clone DBG22, and "DBG22VH" denotes the variable region of the heavy chain of clone DBG22.

TABLE 1

| SEQ ID NO | Designation | Sequence |
|---|---|---|
| 1 | VHCDR1 DBG22 | GFSLTSYIVD |
| 2 | VHCDR2 DBG22 | VIWAGGSTNYNSALRS |
| 3 | VHCDR3 DBG22 | AAYYSYNYDGFAY |
| 4 | VKCDR1 DBG22 | KSSQSLLYTNGKTYLY |
| 5 | VKCDR2 DBG22 | LVSKLDS |
| 6 | VKCDR3 DBG22 | LQSTHFPHT |
| 7 | VHCDR1 35E6 | GYTFTNYWMH |
| 8 | VHCDR2 35E6 | ETNPRNGGTNYNEKFKR |
| 9 | VHCDR3 35E6 | GTSGYDYFDY |
| 10 | VKCDR1 35E6 | RSSQTIVHSNGNTYLE |
| 11 | VKCDR2 35E6 | KVSNRFS |
| 12 | VKCDR3 35E6 | FQASHFPYT |

TABLE 1-continued

| SEQ ID NO | Designation | Sequence |
|---|---|---|
| 13 | VHCDR1 45B9 | GVSLFTYDVD |
| 14 | VHCDR2 45B9 | VMWSGGTTNYNSALKS |
| 15 | VHCDR3 45B9 | DRWSPGGFAY |
| 16 | VKCDR1 45B9 | QSSQSLLYTNGKTYLH |
| 17 | VKCDR2 45B9 | LVSKLDS |
| 18 | VKCDR3 45B9 | LQSTHFPHT |
| 19 | VHCDR1 48E1 | GFSLTSYDVD |
| 20 | VHCDR2 48E1 | VIWAGGSTNYNSALKS |
| 21 | VHCDR3 48E1 | DRWSPGGFAY |
| 22 | VKCDR1 48E1 | KSSQSLLYTNGKTYLI |
| 23 | VKCDR2 48E1 | LVSKLDS |
| 24 | VKCDR3 48E1 | LQTTHFPHT |
| 25 | VHCDR1 49F8 | GFSLSTYGVD |
| 26 | VHCDR2 49F8 | LIWAGGSTTYNSAFKS |
| 27 | VHCDR3 49F8 | ERSGDSPFGY |
| 28 | VKCDR1 49F8 | KSSQSLLYTNGKTYLN |
| 29 | VKCDR2 49F8 | LVSKLDS |
| 30 | VKCDR3 49F8 | LQNSHFPHT |
| 31 | VHCDR1 6A7F1 | GFTFSTYGMS |
| 32 | VHCDR2 6A7F1 | SVTRGGNTYYPDSM |
| 33 | VHCDR3 6A7F1 | DYSGWYFDV |
| 34 | VKCDR1 6A7F1 | RSSQSIVHSNGDTFLE |
| 35 | VKCDR2 6A7F1 | KVSNRFS |
| 36 | VKCDR3 6A7F1 | FQGSRIPYT |
| 37 | VHCDR1 2F1E5 | GFTLTNYGMN |
| 38 | VHCDR2 2F1E5 | WINTYTGEPTYADDFKG |

TABLE 1-continued

| SEQ ID NO | Designation | Sequence |
|---|---|---|
| 39 | VHCDR3 2F1E5 | SAGTDYFDY |
| 40 | VKCDR1 2F1E5 | RASESVDSYGNSFMH |
| 41 | VKCDR2 2F1E5 | LASNLES |
| 42 | VKCDR3 2F1E5 | QQNNEDPWT |
| 43 | VHCDR1 3B4E7 | GYTFTYYTIH |
| 44 | VHCDR2 3B4E7 | YINPASSYTNYIQKFKD |
| 45 | VHCDR3 3B4E7 | GANWDYFDY |
| 46 | VKCDR1 3B4E7 | RSSQNIIQSNGNTYLE |
| 47 | VKCDR2 3B4E7 | KVSNRFS |
| 48 | VKCDR3 3B4E7 | FQGSHVPYT |
| 49 | VHCDR1 1F6G8 | GYTFTSYTTH |
| 50 | VHCDR2 1F6G8 | YINPSSGYTYYIQNFKD |
| 51 | VHCDR3 1F6G8 | GANWDYFDY |
| 52 | VKCDR1 1F6G8 | RSSQNIVQTNGNTYLE |
| 53 | VKCDR2 1F6G8 | KVSSRFS |
| 54 | VKCDR3 1F6G8 | FQGSHVPFT |
| 55 | VHCDR1 2D2E3 | GYTFTHSGMN |
| 56 | VHCDR2 2D2E3 | WINTNTGEPTYAEEFNGR |
| 57 | VHCDR3 2D2E3 | SWWTDYFDY |
| 58 | VKCDR1 2D2F8 | RSSQSIVHSNGNTYLE |
| 59 | VKCDR2 2D2E3 | KVSNRFS |
| 60 | VKCDR3 2D2E3 | FQGSHFPYT |
| 61 | VHCDR1 27A9 | GYTFTNCYMH |
| 62 | VHCDR2 27A9 | ETNPRNGGTNYNEKFKR |
| 63 | VHCDR3 27A9 | GTSGYEYFDY |

TABLE 1-continued

| SEQ ID NO | Designation | Sequence |
|---|---|---|
| 64 | VKCDR1 27A9 | RSSQSIVHSDGNIYLE |
| 65 | VKCDR2 27A9 | KVSYRFS |
| 66 | VKCDR3 27A9 | FQGSHVPYT |
| 67 | VHCDR1 5C | GYTFTDYYMH |
| 68 | VHCDR2 5C | ETNPRNGGTTYNEKFKG |
| 69 | VKCDR3 18 | FQASHVPYT |
| 70 | DBG22VH | QVQLEQSGPG LVAPSQRLSI TCTVSGFSLT SYIVDWVRQS PGKGLEWLGV IWAGGSTNYN SALRSRLSIT KSNSKSQVFL QMNSLQTDDT AIYYCASAAY YSYYNYDGFA YWGQGTLVTV SA |
| 71 | DBG22VK | DVVMTQTPLT LSVTIGQPAS ISCKSSQSLL YTNGKTYLYW LLQRPGQSPK RLIYLVSKLD SGVPDRFSGS GSGTDFTLKI SRVEAEDVGI YYCLQSTHFP HTFGGGTKLE IK |
| 72 | 35E6VH | QVQLQQPGAE LVKPGASVKL SCKTSGYTFT NYWMHWVRQR PGQGLEWIGE TNPRNGGTNY NEKFKRKATL TVDKSSNTAY MQLSSLTFGD SAVYYCTIGT SGYDYFDYWG QGTTLTVSS |
| 73 | 35E6VK | DVLMTQTPLS LPVSLGDQAS ISCRSSQTIV HSNGNTYLEW YLQKPGQSPK LLIYKVSNRF SGVPDRFSGS GSGTGFTLKI SRVEAEDLGV YFCFQASHFP YTFGGGTKLE IK |
| 74 | 45B9VH | QVQLKQSGPG LVAPSQSLSI TCTVSGVSLF TYDVDWVRQS PGKDLEWLGV MWSGGTTNYN SALKSRLNIM KDSSKSQVFL KMSGLQTDDT GIYYCATDRW SPGGFAYWGQ GTLVTVSA |
| 75 | 45B9VK | DVVMTQTPLT LSVLIGQPAS ISCQSSQSLL YTNGKTYLHW LLQRPGQSPK RLIYLVSKLD SGVPDRFSGS GSGTDFTLKI SRVEAEDLGV YYCLQSTHFP HTFGGGTKLE IR |
| 76 | 48E1VH | QVQLKQSGPG LVAPSQSLSI TCTVSGFSLT SYDVDWVRQS PGKGLEWLGV IWAGGSTNYN SALKSRLIIS KDNSKNQVFL RMNSLQTDDT AMYYCASDRW SPGGFAYWGQ GTLVTVSA |
| 77 | 48E1VK | DVVMTQTPLT LSVTIGQPAS ISCKSSQSLL YTNGKTYLIW LLQRPGQSPK RLIHLVSKLD SGVPDRFSGS GSGTDFTLKI SRVEAEDLGV FYCLQTTHFP HTFGGGTKLE IR |
| 78 | 49F8VH | QVQLKQSGPG LVAPSQSLSI TCTVSGFSLS TYGVDWVRQS PKKGLEWLGL IWAGGSTTYN SAFKSRLSIS KDNSKSQVFL KMNSLQTDDT AMYYCASERS GDSPFGYWGQ GTLVTVSA |
| 79 | 49F8VK | DVVMTQSPLI LSVTIGQPAS ISCKSSQSLL YTNGKTYLNW LLQRPGQSPE RLIHLVSKLD SGVPDRFSGS GSGTDFTLKI SRVEAEDLGV YYCLQNSHFP HTFGSGTKLE IK |
| 80 | 6A7F1VH | EVKLVESGGD LVRPGGSLKL SCAASGFTFS TYGMSWVRQS PEKRLEWVAS VTRGGNTYYP DSMRGRFTIS RDNVGNILYL HLRSLRSEDT AIYFCARDYS GWYFDVWGAG TTVTVSS |
| 81 | 6A7F1VK | DVLMTQIPLS LPVSLGDQAS ISCRSSQSIV HSNGDTFLEW YLQKSGQSPK LLIYKVSNRF SGVPDRFSGS GSGTDFTLKI SRVEAEDLGV YYCFQGSRIP YTFGGGTKLE IK |
| 82 | 3B4E7VH | QVQLQQSGAE LARPGASVKM SCKASGYTFT YYTIHWVKQR PGQGLEWIGY INPASSYTNY IQKFKDRATL TADKSSSTAY MQLSSLTSED SAVFYCARGA NWDYFDYWGQ GTTLTVSS |
| 83 | 3B4E7VK | DVLMTQTPLS LPVSLGDQAS ISCRSSQNII QSNGNTYLEW YLQKPGQSPK LLIYKVSNRF SGVPDRFSGS GSGTDFTLKI SRVEAEDLGV YYCFQGSHVP YTFGGGTNLE IK |
| 84 | 2F1E5VH | QIQLVQSGPE LKKPGETVKI SCKSSGFTLT NYGMNWVKQV PGKGLRWMGW INTYTGEPTY ADDFKGRFAF SLETSARTAY LQINNLKNED AATYFCARSA GTDYFDYWGQ GTTLTVSS |

TABLE 1-continued

| SEQ ID NO | Designation | Sequence |
|---|---|---|
| 85 | 2F1E5VK | NFVLTQSPAS LAVSLGQRAT ISCRASESVD SYGNSFMHWC QQKPGQPPKL LIYLASNLES GVPARFSGSG SRTDFTLTID PVEADDAATY YCQQNNEDPW TFGGGTKLEI K |
| 86 | 1F6G8VH | QIQLVQSGPE LKKPGETVKI SCKSSGFTLT NYGMNWVKQV PGKGLRWMGW INTYTGEPTY ADDFKGRFAF SLETSARTAY LQINNLKNED AATYFCARSA GTDYFDYWGQ GTTLTVSS |
| 87 | 1F6G8VK | DVLMTQTPLS LPVSLGDQAS ISCRSSQNIV QTNGNTYLEW YLQKPGQSPN LLIYKVSSRF SGVPDRFSGS GSGTDFTLKI SRVEAEDLGV YYCFQGSHVP FTFGGGTKLE IK |
| 88 | 2D2E3VH | QAQIHLVQSG PELKKPGETV KISCKASGYT FTHSGMNWMK QTPGKDLKWM GWINTNTGEP TYAEEFNGRF AFSLEASANT AYLQINNLKN EDTATYFCAR SWWTDYFDYW GQGTTLTVSS |
| 89 | 2D2E3VK | DVLMTQTPLS LPVSLGDQTS ISCRSSQSIV HSNGNTYLEW YLQKPGQSPE LLIYKVSNRF SGVPDRISGS GSGTDFTLKI SRVEAEDLGV YYCFQGSHFP YTFGGGTKLE IT |
| 90 | 27A9VH | QVQLQQPGAE LVKPGASVKL SCKASGYTFT NCYMHWVKQR PGQGLEWIGE TNPRNGGTNY NEKFKRKATL TVNKYSSTAY MQLSSLTSED SAVYYCTIGT SGYEYFDYWG QGTTLTVSS |
| 91 | 27A9VK | NILMTQTPLS LPVSLGDQAS ISCRSSQSIV HSDGNIYLEW YLQKPGQSPK VLIYKVSYRF SGVPDRFSGS GSGTYFTLKI SRVEAEDLGV YFCFQGSHVP YTFGGGTKLE IK |
| 92 | VH5C | QVQLVQSGAE VKKPGASVKV SCKASGYTFT DYYMHWVRQA PGQGLEWMGE TNPRNGGTTY NEKFKGKATM TRDTSTSTAY MELSSLRSED TAVYYCTIGT SGYDYFDYWG QGTLVTVSS |
| 93 | VK18 | DIVMTQTPLS LSVTPGQPAS ISCRSSQSIV HSDGNIYLEW YLQKPGQSPK LLIYKVSYRF SGVPDRFSGS GSGTDFTLKI SRVEAEDVGV YYCFQASHVP YTFGQGTKLE IK |
| 94 | VK21 | DIVMTQTPLS LSVTPGQPAS ISCRSSQSIV HSDGNIYLEW YLQKPGQSPK LLIYKVSYRF SGVPDRFSGS GSGTGFTLKI SRVEAEDVGV YYCFQASHVP YTFGGGTKLE IK |
| 95 | Clone 22 chimeric HC | QVQLEQSGPG LVAPSQRLSI TCTVSGFSLT SYIVDWVRQS PGKGLEWLGV IWAGGSTNYN SALRSRLSIT KSNSKSQVFL QMNSLQTDDT AIYYCASAAY YSYYNYDGFA YWGQGTLVTV SAASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKRV EPKSCDKTHT CPPCPAPEAA GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 96 | Clone 22 chimeric LC | DVVMTQTPLT LSVTIGQPAS ISCKSSQSLL YTNGKTYLYW LLQRPGQSPK RLIYLVSKLD SGVPDRFSGS GSGTDFTLKI SRVEAEDVGI YYCLQSTHFP HTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 97 | hCL Domain | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 98 | hCH Domain | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

TABLE 1-continued

| SEQ ID NO | Designation | Sequence |
|---|---|---|
| 99 | HCVH5C | QVQLVQSGAE VKKPGASVKV SCKASGYTFT DYYMHWVRQA PGQGLEWMGE TNPRNGGTTY NEKFKGKATM TRDTSTSTAY MELSSLRSED TAVYYCTIGT SGYDYFDYWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SC |
| 100 | LCVK18 | DIVMTQTPLS LSVTPGQPAS ISCRSSQSIV HSDGNIYLEW YLQKPGQSPK LLIYKVSYRF SGVPDRFSGS GSGTDFTLKI SRVEAEDVGV YYCFQASHVP YTFGQGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 101 | LCVK21 | DIVMTQTPLS LSVTPGQPAS ISCRSSQSIV HSDGNIYLEW YLQKPGQSPK LLIYKVSYRF SGVPDRFSGS GSGTGFTLKI SRVEAEDVGV YYCFQASHVP YTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |

Figure 5:
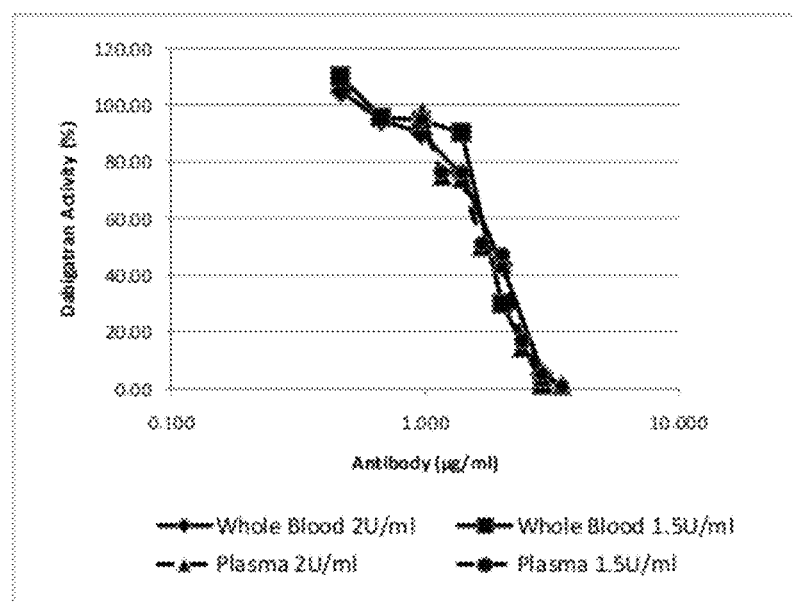
FIG. 5: A mouse monoclonal antibody (Clone 22) reverses the anticoagulant effect of dabigatran in human plasma and in human whole blood. Increasing concentrations of mouse antibody were added to human plasma or whole blood that had been preincubated with 30 nM dabigatran. The assay was initiated by the addition of 1.5-2 U/mL of thrombin and clotting time was measured. 100% dabigatran activity was defined as the difference in clotting time in the presence and absence of compound. The antibody dose dependently inhibited the dabigatran mediated prolongation of clotting time.
Figure 6:
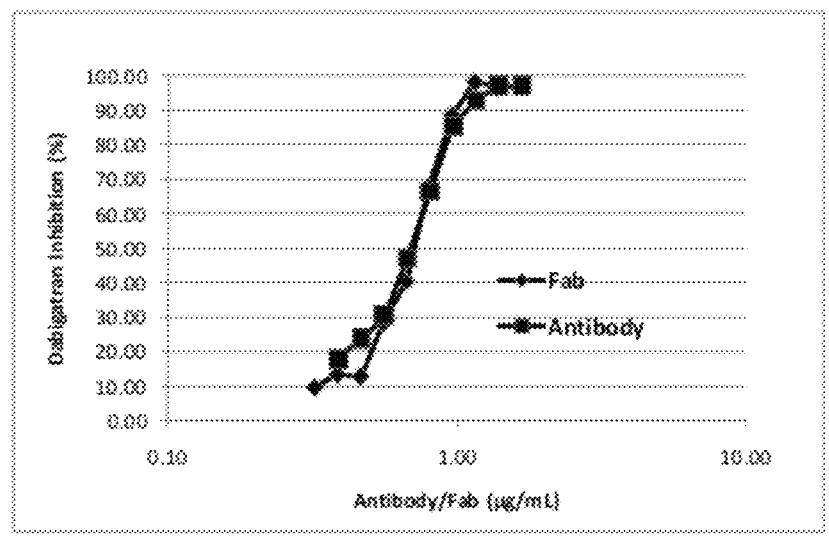
FIG. 6: A mouse Fab generated from the Clone 22 antibody reverses the anticoagulant effect of dabigatran in human plasma. Increasing concentrations of mouse Fab were added to human plasma that had been preincubated with 7 nM dabigatran. The intact antibody was also tested as a positive control. The assay was initiated by the additon of 0.4 U/mL of thrombin and clotting time was measured. 100% inhibition was defined as the complete block of the dabigatran mediated increase in clotting time. The Fab dose dependently inhibited the dabigatran induced prolongation in clotting time in human plasma.

The mouse monoclonal antibody clone 22 was tested for its ability to neutralize dabigatran anticoagulant activity in human plasma in the thrombin clotting time assay outlined in Example II. The antibody completely reversed the dabigatran-mediated prolongation of thrombin dependent clotting in human plasma in a dose dependent manner (FIG. 5). The antibody also effectively inhibited dabigatran function in human whole blood. A Fab generated from this antibody blocked dabigatran activity in human plasma demonstrating that monovalent antigen binding domains can neutralize compound anticoagulant activity. (FIG. 6).

Figure 7:
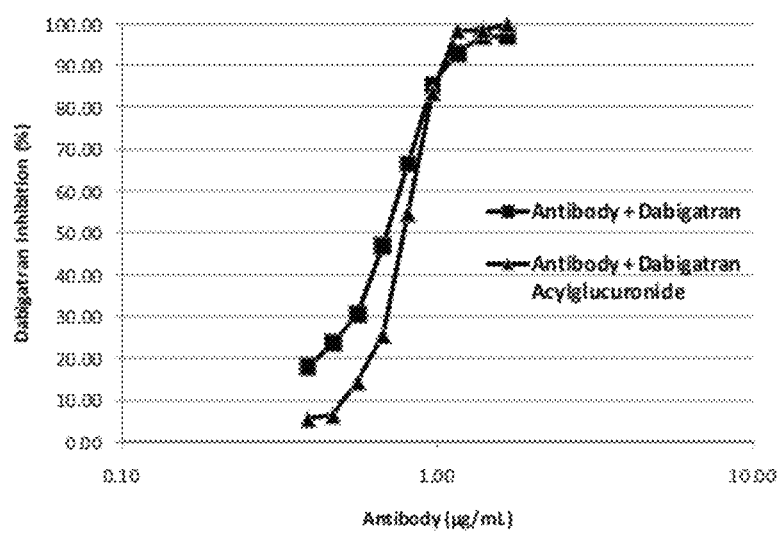
FIG. 7: A mouse monoclonal antibody (Clone 22) reverses the anticoagulant effect of dabigatran acylglucuronide in human plasma. Increasing concentrations of mouse antibody were added to human plasma that had been preincubated with 7 nM of dabigatran acylglucuronide or dabigatran. The assay was initiated by the additon of 0.4 U/mL of thrombin and clotting time was measured. 100% inhibition was defined as the complete block of the compound mediated increase in clotting time. The antibody dose dependently inhibited the dabigatran acylglucuronide induced prolongation in clotting time in human plasma.

The major metabolic pathway of dabigatran in humans is through the glucuronidation of the carboxylate moiety. Dabigatran acylglucuronides have been shown to be pharmacologically active (Ebner et al., Drug Metab. Dispos. 2010, 38(9):1567-75). To test whether the mouse monoclonal antibody clone 22 could neutralize these metabolites, dabigatran acylglucuronides were purified from the urine of rhesus monkeys treated with dabigatran and evaluated in the thrombin clotting time assay. The antibody dose dependently reversed the dabigatran acylglucuronide-mediated prolongation of thrombin dependent clotting in human plasma with similar potency to that seen with dabigatran (FIG. 7). Thus the antibody is effective in blocking the anticoagulant activity of dabigatran metabolites found in humans.

The affinities of the Fab and the mouse-human chimeric antibodies comprising the variable domains of clone 22 were determined using Kinexa technology. A constant concentration of Fab or chimeric antibody was incubated with various concentrations of dabigatran until equilibrium was reached. After this incubation the concentration of free antibody was determined by capturing the antibody on Neutravidin beads coupled with a Biotin-conjugated dabigatran analog. The captured Fab was detected with an anti-Mouse IgG (Fab specific) F(ab')2 fragment labeled with FITC. The captured chimeric antibodies were detected with an anti-human IgG conjugated with Cy5. The dissociation constants were calculated using a 1:1 binding model. The results from these experiments are summarized in the table below.

Affinity of Anti-Dabiaatran Antibodies

| Antibody | Apparent $K_d$ |
|---|---|
| Clone 22 Fab | 48 pM |
| Clone 22 Chimeric Ab | 34 pM |

Both the Fab and the chimeric antibodies bind dabigatran with high affinity.

Thrombin Clotting Time Assay

Briefly human plasma is obtained by taking whole blood into 3.13% sodium citrate. This is then centrifuged to obtain platelet free plasma and transferred to a separate tube and frozen until required on the day of the assay. Plasma is thawed at 37° C. on the day of the assay.

The thrombin clotting time is performed as follows. First thrombin is diluted to manufacturer's specification (3 IU/mL thrombin) in the buffer provided (Dade Behring Test kit) and prewarmed to 37° C. It is used within 2 hrs of being prepared. All assays were performed on a commercially available CL4 clotting machine (Behnk Electronics, Norderstadt, Germany). Fifty µL of plasma is pipetted into provided cuvettes with a magnetic stirrer and allowed to stir for 2 min in the well preheated to 37° C. in the CL4 machine. At this point 100 µL of the thrombin solution is added and the time required for the plasma sample to clot is recorded automatically by the CL4. Dabigatran is preincubated for 5 min in plasma in the provided cuvettes, before adding thrombin and starting the measurement. If antibody is also tested (up 50 µL of stock solution), there is a further 5 minute incubation at 37° C. before beginning clotting (i.e. 10 Min total incubation with dabigatran, 5 min total incubation with antibody and then clotting is initiated with thrombin).

Figure 8:
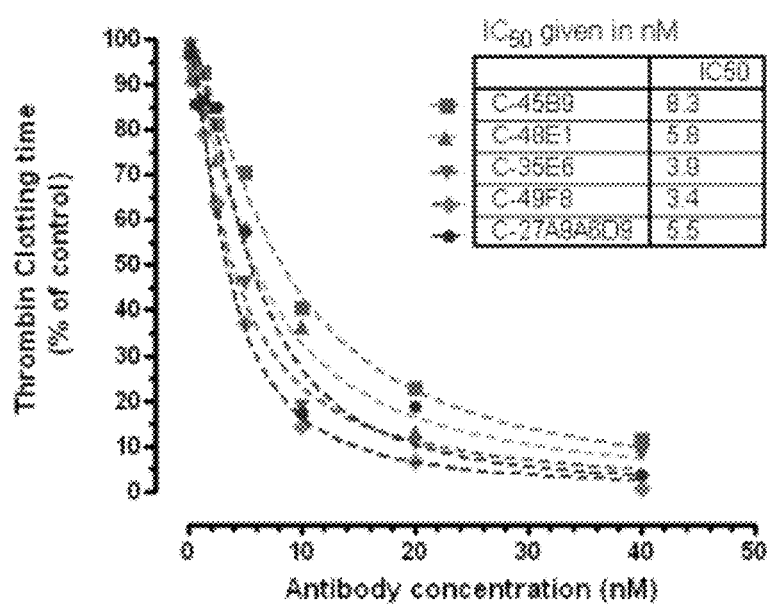
FIG. 8: Selected chimeric antibodies inhibit dabigatran activity in the thrombin clotting time assay. Increasing concentrations of antibody were added to human plasma that had been preincubated with 7 nM dabigatran. The intact antibody was also tested as a positive control. The assay was initiated by the additon of 0.4 U/mL of thrombin and clotting time was measured. 100% inhibition was defined as the complete block of the dabigatran mediated increase in clotting time. The antibodies dose dependently inhibited the dabigatran induced prolongation in clotting time in human plasma.
Figure 9:
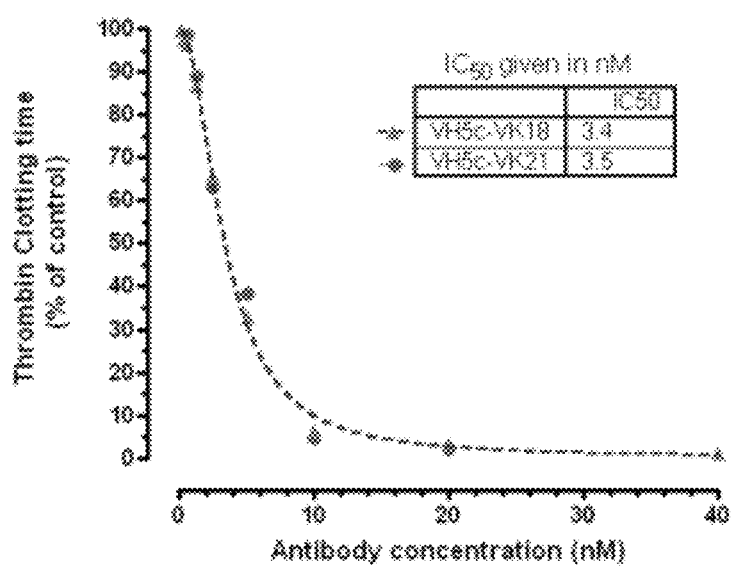
FIG. 9: Fab VH5c/Vk18 (SEQ ID NO: 99 and SEQ ID NO: 100) and VH5c/Vk21 (SEQ ID NO: 99 and SEQ ID NO: 101) inhibit dabigatran activity in the thrombin clotting time plasma assay. The assay was performed as described above.
Figure 10:
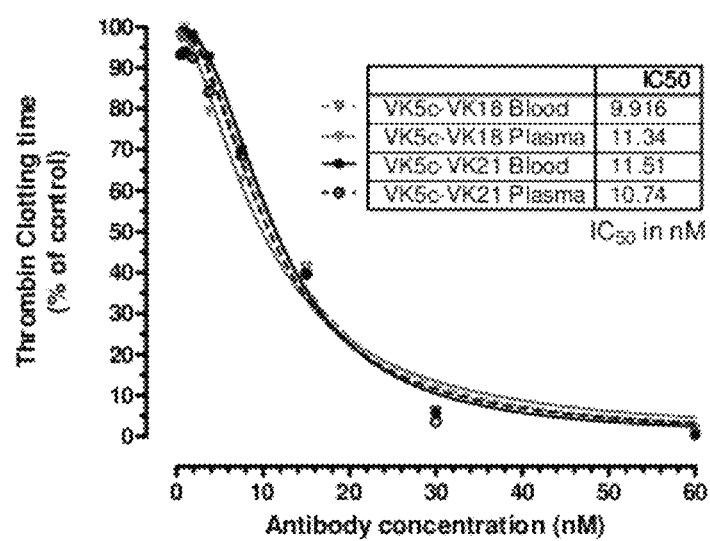
FIG. 10: Fab VH5c/Vk18 (SEQ ID NO: 99 and SEQ ID NO: 100) and VH5c/Vk21 (SEQ ID NO: 99 and SEQ ID NO: 101) inhibit dabigatran activity in the plasma and whole blood thrombin clotting time assay. The assay was performed as described above.

Activity of chimeric antibodies and humanized Fabs in the thrombin time assay is shown in FIGS. 8-10, respectively.

Affinity Determinations (Kinexa Method)

The affinities of Fab and mouse-human chimeric antibodies were determined using KinExA® technology. A constant concentration of Fab or chimeric antibody was incubated with various concentrations of dabigatran until equilibrium was reached. After this incubation the concentration of free antibody was determined by capturing the antibody on Neutravidin beads coupled with a Biotin-conjugated dabigatran analog. The captured Fab was detected with an anti-human IgG (Fab specific) F(ab')2 fragment labeled with FITC. The captured chimeric antibodies were detected with an anti-human IgG conjugated with Cy5. The dissociation constants ($K_D$) were calculated using a 1:1 binding model.

To measure rate constants ($k_{on}$ and $k_{off}$) with the KinExA® instrument, the Kinetics Direct method was used. In this method, the binding partners are mixed in solution, and the concentration of free active binding sites is probed over time as active binding sites are depleted due to the formation of complexes. Data points are collected at specified time intervals and the signals are analyzed. In this way, $k_{on}$ is measured directly and the off-rate $k_{off}$ is calculated as $k_{off}=K_D \times k_{on}$.

TABLE $K_D$ values of chimeric antibodies determined using KinExA ® technology

| Chimeric Ab | $K_D$ (pM) |
|---|---|
| 45B6 | 545 |
| 48E1 | 281 |
| 35E6 | 52 |
| 49F8 | 40 |
| 27A9 | 120 |

Fab-Dabigatran Complex Formation and Crystallization

The Fabs were concentrated to 10 mg/ml, mixed with a 2 molar excess of dabigatran and incubated for 1 h at 4° C. Complex and crystallization solution were mixed 1:1. The complex crystallizes in 25% PEG 1500, 0.1 M SPG buffer (pH7).

Data Collection and Structure Determination

Datasets for all crystals were collected on the Swiss light Source beamline PXI-X06SA of the Paul Scherrer Institut. All datasets were processed with the autoPROC package (Vonrhein, C., Flensburg, C., Keller, P., Shutt A., Smart, O., Paciorek, W., Womack, T. & Bricogne, G. (2011). Data processing and analysis with the autoPROC toolbox. Acta Cryst. D67, 293-302.).

Fab VH5C/VK21:Dabigatran crystals grew in space group P212121 with unit cell dimensions a=59.97 Å, b=78.39 Å, c=87,67 Å and diffract to 2.2 Å resolution. The complex structure was solved by molecular replacement with the program phaser (Collaborative Computational Project, number 4. 1994. "The CCP4 Suite: Programs for Protein Crystallography". Acta Cryst. D50, 760-763. Phaser crystallographic software. McCoy A J, Grosse-Kunstleve R W, Adams P D, Winn M D, Storoni L C, Read R J. J. Appl. Cryst. (2007). 40, 658-674.) using a homologous Fab structure (PDB-ID 1C1E) as the starting search model. Analysis of the electron density map showed clear electron density for dabigatran. The complete structure was improved with multiple rounds of model building with Coot and refinement with autoBUSTER (Coot: model-building tools for molecular graphics" Emsley P, Cowtan K *Acta Crystallographica Section D-Biological Crystallography* 60: 2126-2132 Part 12 Sp. Iss. 1 December 2004. Bricogne G., Blanc E., Brandi M., Flensburg C., Keller P., Paciorek W., Roversi P, Sharff A., Smart O. S., Vonrhein C., Womack T. O. (2011). BUSTER version 2.11.2. Cambridge, United Kingdom: Global Phasing Ltd).

Fab VH5C/VK18:Dabigatran crystals grew in space group P21 and P212121, respectively. Crystals with space group P21 showed unit cell dimensions of a=51.81 Å, b=128.92 Å, c=60.26 Å and diffract to 1.9 Å resolution. Crystals with space group P212121 showed unit cell dimensions of a=48.20 Å, b=59.74 Å, c=127.69 Å and diffract to 2.2 Å resolution. Both complex structures were solved by molecular replacement with the program phaser using the structure of Fab VH5C/VK21 as the starting search model. Analysis of the electron density maps showed clear electron density for dabigatran. The complete structures were improved with multiple rounds of model building with Coot and refinement with autoBUSTER.

In Silico Analysis of Spatial Aggregation Propensity (SAP)

The spatial aggregation propensities (SAP) for each atom and each residue was calculated as described in (1) with the exception that residue hydrophobicity parameters where taken from (2). The Fv SAP is calculated as the sum over all positive residue SAP values in the variable domains of the antibody. The CDR SAP is calculated as the sum over all positive residue SAP values in the complementary determining regions of the antibody. Fv SAP and CDR SAP have been calculated for 850 different antibody structures from the protein data bank (PDB), yielding a mean ($\mu_{Fv}$ and $\mu_{CDR}$) and standard deviation values ($\sigma_{Fv}$ and $\sigma_{CDR}$) for both properties.

Z-scores for the Fv SAP and CDR SAP for the antibodies where then calculated according to $$Z\text{-score(Fv SAP)} = (\text{Fv SAP} - \mu_{Fv})/\sigma_{Fv} \text{ and}$$

$$Z\text{-score(CDR SAP)} = (\text{CDR SAP} - \mu_{CDR})/\sigma_{CDR}.$$

Figure 11:
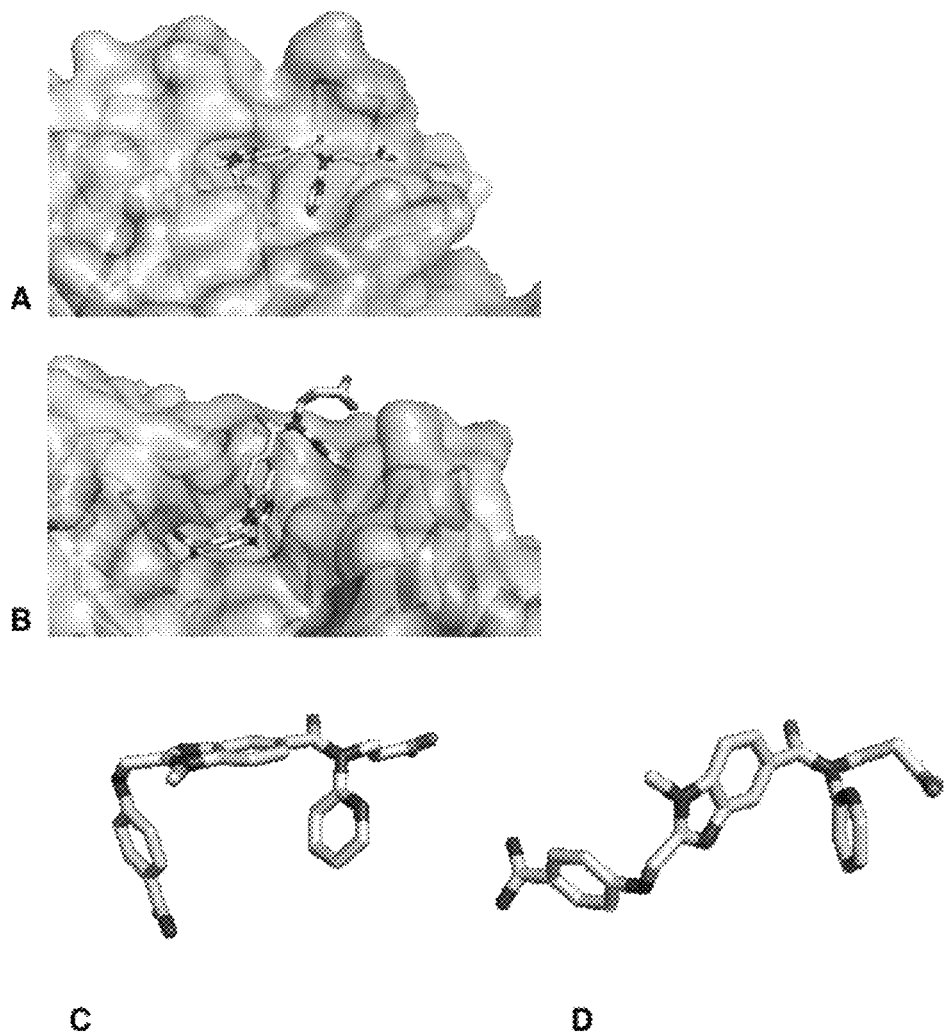
FIG. 11: Crystal structure of the Fab-Dabigatran complexes. A: Crystal structure of Fab 18/15 (WO2011089183) in complex with dabigatran. B: Crystal structure of Fab VH5c/Vk18 (SEQ ID NO: 99 and SEQ ID NO: 100) in complex with dabigatran. C: Conformation of dabigatran as seen in the crystal structure with Fab 18/15. D: Extended conformation of dabigatran as seen in the crystal structure with VH5c/Vk18.
Figure 12:
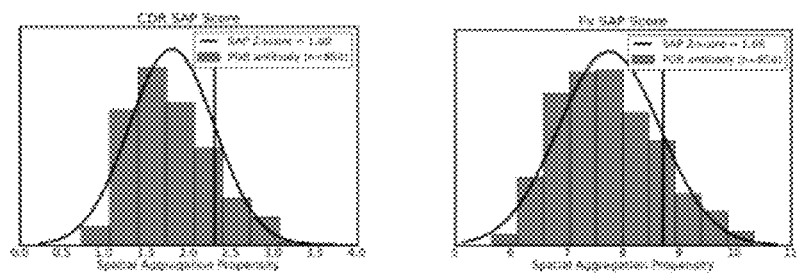
FIG. 12: Spatial aggregation propensities (SAP) calculated for (A) Fab 18/15 (B) Fab VH5c/Vk18 and (C) Fab VH5c/Vk21 comprising the CDRs (left panels) or the whole Fv region (right panels).
Figure 12:
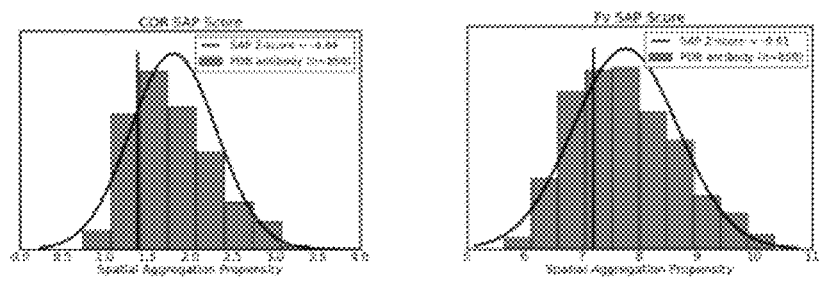
Figure 12:
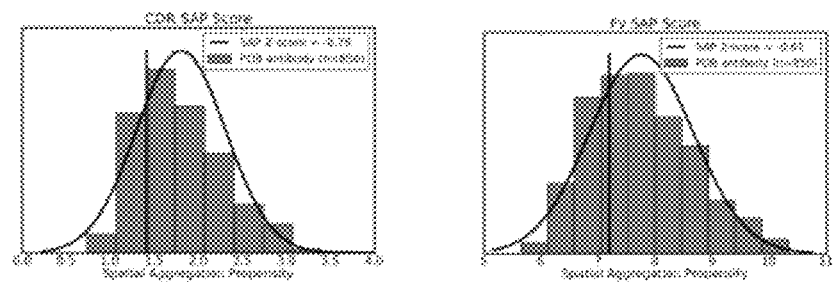

Results (FIG. 11):

Humanized Fab 18/15:

Z-score(Fv SAP)=1.06

Z-score(CDR SAP)=1.00

Humanized Fab VH5C/VK18:

Z-score(Fv SAP)=−0.61

Z-score(CDR SAP)=−0.84

Humanized Fab VH5C/VK21:

Z-score(Fv SAP)=−0.61

Z-score(CDR SAP)=−0.78

Fab 18/15 (see WO2011089183) has more solvent-exposed hydrophobic surface than the average of known antibodies in the protein data bank.

Surprisingly, both VH5C/VK18 (SEQ ID NO: 99/SEQ ID NO: 100) and VH5C/VK21 comprises SEQ ID NO: 99/SEQ ID NO: 101) have less solvent-exposed hydrophobic surface than the average of known antibodies in the protein data bank (negative Z-scores). This means that these compounds have an increased solubility in aqueous media and a lower tendency for aggregation, making them more suitable for stable drug formulations with high antibody concentrations.

(1) Chennamsetty et. al., Proc Natl Acad Sci; 2009, 106 (29), pg 11937-11942

(2) Cowan and Whittaker, Pept Res; 1990, 3(2), pg 75-80

Expression of Fab in CHO Cells

Figure 13:
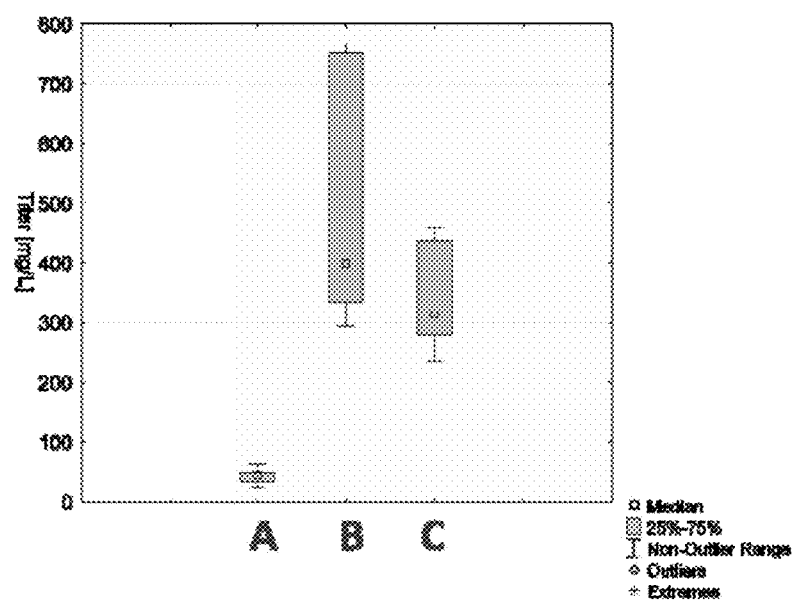
FIG. 13: Titers of (A) Fab 18/15 (B) Fab VH5c/Vk18 and (C) Fab VH5c/Vk21 from fed batch runs of CHO cells transfected with corresponding Fab expression constructs.

Fabs were produced by transient transfection into CHO DG44 cells and subsequent selection and generation of stable cell pools. FIG. 13 shows the titers of fed batch runs with Fab 18/15 (see WO2011089183), Fab VH5c/Vk18 and Fab VH5c/Vk21. Surprisingly, Fabs VH5c/Vk18 and VH5c/Vk21 show 5-10 fold higher titers as compared to Fab 18/15.

What we claim:

1. An antibody molecule against dabigatran comprising a heavy chain variable domain with a CDR1 of SEQ ID NO: 67, a CDR2 of SEQ ID NO: 68, and a CDR3 of SEQ ID NO: 9, and a light chain variable domain with a CDR1 of SEQ ID NO: 64, a CDR2 of SEQ ID NO: 65, and a CDR3 of SEQ ID NO: 69.

2. The antibody molecule of claim 1 comprising a heavy chain variable domain of SEQ ID NO: 92, and a light chain variable domain of SEQ ID NO: 93.

3. The antibody molecule of claim 1 comprising a heavy chain variable domain of SEQ ID NO: 92, and a light chain variable domain of SEQ ID NO: 94.

4. The antibody molecule of claim 1 comprising a heavy chain of SEQ ID NO: 99, and a light chain of SEQ ID No: 100.

5. The antibody molecule of claim 1 comprising a heavy chain of SEQ ID NO: 99, and a light chain of SEQ ID No: 101.

6. The antibody molecule of claim 1, wherein the antibody is a polyclonal antibody, a monoclonal antibody, a human antibody, a humanized antibody, a chimeric antibody, a Fab, Fab', or F(ab')$_2$ fragment of an antibody, a single chain antibody, a single chain variable fragment (scFv), a Small Modular Immunopharmaceutical (SMIP), or a diabody.

7. The antibody molecule of claim 1 for use in medicine.

8. Antibody molecule of claim 1 for use in the therapy or inhibition of side effects of dabigatran, and/or for reversal of an overdosing of dabigatran.

9. Antibody molecule of claim 8, wherein the side effect is a bleeding event.

10. A kit comprising an antibody of claim 1 or 6, or a pharmaceutical composition thereof.

11. A kit comprising:
    (a) an antibody of claim 1 or 6, or a pharmaceutical composition thereof;
    (b) a container; and
    (c) a label.

12. A kit comprising an antibody of claim 1 or 6, and dabigatran, dabigatran etexilate, a prodrug of dabigatran or a pharmaceutically acceptable salt thereof.

13. Method of manufacturing an antibody molecule of claim 1 or 6, comprising
    (a) providing a host cell comprising one or more nucleic acids encoding said antibody molecule in functional association with an expression control sequence,
    (b) cultivating said host cell, and
    (c) recovering the antibody molecule from the cell culture.

14. Method of treatment or prevention of side effects of anticoagulant therapy, or of an overdosing event in anticoagulant therapy, comprising administering an effective amount of an antibody molecule of claim 1 or 6 to a patient in need thereof.

15. A method for neutralizing or partially neutralizing dabigatran or 1-O-acylglucuronide of dabigatran in a patient being treated with dabigatran, dabigatran etexilate, a prodrug of dabigatran or a pharmaceutically acceptable salt thereof, comprising administering an antibody of claim 1 or 6, or a pharmaceutical composition thereof.

16. A method for neutralizing or partially neutralizing dabigatran or 1-O-acylglucuronide of dabigatran in a patient comprising:
    (a) confirming that a patient was being treated with dabigatran, dabigatran etexilate, a prodrug of dabigatran or a pharmaceutically acceptable salt thereof, and the amount that was taken by the patient;
    (b) neutralizing dabigatran or 1-O-acylglucuronide with an antibody of claim 1 or 6 prior to performing a clotting or coagulation test or assay wherein dabigatran or the 1-O-acylglucuronide of dabigatran would interfere with the accurate read out of the test or assay results;
    (c) performing the clotting or coagulation test or assay on a sample taken from the patient to determine the level of clot formation without dabigatran or 1-O-acylglucuronide of dabigatran present; and
    (d) adjusting an amount of dabigatran, dabigatran etexilate, a prodrug of dabigatran or a pharmaceutically acceptable salt thereof administered to the patient in order to achieve the appropriate balance between clot formation and degradation in a patient.

17. A method for reducing the concentration of dabigatran or 1-O-acylglucuronide of dabigatran in plasma of a patient being treated with dabigatran, dabigatran etexilate, a prodrug of dabigatran or a pharmaceutically acceptable salt thereof, comprising the step of administering an antibody of claim 1 or 6, or a pharmaceutical composition thereof that neutralizes the activity of dabigatran or 1-O-acylglucuronide in the patient.

18. A method of reversal of the anticoagulant effect of dabigatran or 1-O-acylglucuronide of dabigatran in a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures, comprising the step of administering an antibody of claim 1 or 6, or a pharmaceutical composition thereof that neutralizes the activity of dabigatran or 1-O-acylglucuronide in the patient.

19. A method for reversing or reducing the activity of dabigatran or 1-O-acylglucuronide of dabigatran in a patient experiencing bleeding or at risk for bleeding due to an impaired clotting ability or trauma, comprising the steps of:
- (d) determining the amount of dabigatran or 1-O-acylglucuronide of dabigatran present in the patient;
- (e) administering an effective amount of an antibody of claim 1 or 6, or a pharmaceutical composition thereof to reverse or reduce the activity of dabigatran or 1-O-acylglucuronide of dabigatran determined in the patient; and
- (f) monitoring a thrombin clotting time of the patient to ensure a reversal or reduction in activity of dabigatran or 1-O-acylglucuronide of dabigatran has been reached.

\* \* \* \* \*